US007160735B2

(12) United States Patent
Dehlinger et al.

(10) Patent No.: US 7,160,735 B2
(45) Date of Patent: Jan. 9, 2007

(54) TAGGED MICROPARTICLE COMPOSITIONS AND METHODS

(75) Inventors: Peter Dehlinger, Palo Alto, CA (US); Sharat Singh, San Jose, CA (US); Hrair Kirakossian, San Jose, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 603 days.

(21) Appl. No.: 10/290,575

(22) Filed: Nov. 8, 2002

(65) Prior Publication Data

US 2003/0134333 A1 Jul. 17, 2003

Related U.S. Application Data

(63) Continuation-in-part of application No. 10/154,042, filed on May 21, 2002, which is a continuation-in-part of application No. 09/698,846, filed on Oct. 27, 2000, now Pat. No. 6,627,400, which is a continuation-in-part of application No. 09/602,586, filed on Jun. 21, 2000, now Pat. No. 6,514,700, and a continuation-in-part of application No. 09/684,386, filed on Oct. 4, 2000, now abandoned, which is a continuation-in-part of application No. 09/561,579, filed on Apr. 28, 2000, now Pat. No. 6,682,887.

(60) Provisional application No. 60/337,768, filed on Nov. 9, 2001.

(51) Int. Cl.
*G01N 33/543* (2006.01)
*G01N 33/552* (2006.01)
*G01N 33/546* (2006.01)
*G01N 33/532* (2006.01)
*G01N 33/533* (2006.01)
*G01N 33/53* (2006.01)

(52) U.S. Cl. ...................... 436/518; 436/527; 436/533; 436/823; 436/824; 436/544; 436/546; 435/7.1; 435/7.92

(58) Field of Classification Search ................ 436/533, 436/823, 824, 544, 546, 518, 527; 435/7.1, 435/7.92, 6
See application file for complete search history.

(56) References Cited

U.S. PATENT DOCUMENTS 4,274,240 A 6/1981 Soum .......................... 52/583

(Continued)

FOREIGN PATENT DOCUMENTS

EP 0 484 027 A1 5/1992

(Continued)

OTHER PUBLICATIONS

Adam et al., "Photooxygenation (Singlet Oxygen) of Tetrathioethylenes", Journal of the American Chemical Society, vol. 94:4, 1972, pp. 1206-1208.

(Continued)

*Primary Examiner*—Christopher L. Chin
*Assistant Examiner*—Shafiqul Haq
(74) *Attorney, Agent, or Firm*—Jones Day

(57) ABSTRACT

Compositions and methods are disclosed for detecting multiple target analytes in a sample using microparticles having molecular tags attached by cleavable linkages. Generally, an assay mixture is formed comprising a sample and a reagent comprising multiple such microparticles under conditions that permit stable complexes to form between binding moieties on the surfaces of the microparticles and the analytes. In one aspect of the invention, the a second binding composition is added so that complexes form among the microparticle-bound binding moieties, the analytes, and second binding moieties of the second binding composition. Such second binding moieties have cleavage-inducing moieties attached that upon activation cause the cleavage of the cleavable linkages and the release of molecular tags. Released molecular tags are separated and the presence and/or amount of the target analytes are determined based on the analysis of the released and separated molecular tags.

19 Claims, 28 Drawing Sheets

U.S. PATENT DOCUMENTS

| | | | |
|---|---|---|---|
| 4,331,590 A | 5/1982 | Bocuslaski | 260/112 B |
| 4,650,750 A | 3/1987 | Giese | 435/7 |
| 4,675,300 A | 6/1987 | Zare | 436/172 |
| 4,709,016 A | 11/1987 | Giese | 530/389 |
| 4,780,421 A | 10/1988 | Kameda | 436/518 |
| 5,057,412 A | 10/1991 | Rabin | 435/6 |
| 5,254,469 A | 10/1993 | Warren, III | 435/188 |
| 5,310,687 A | 5/1994 | Bard et al. | |
| 5,324,401 A | 6/1994 | Yeung | 204/180.1 |
| 5,326,692 A | 7/1994 | Brinkley et al. | |
| 5,340,716 A | 8/1994 | Ullman | 435/6 |
| 5,360,819 A | 11/1994 | Giese | 514/538 |
| 5,470,705 A | 11/1995 | Grossman | 435/6 |
| 5,494,793 A | 2/1996 | Schindele | 435/6 |
| 5,514,543 A | 5/1996 | Grossman | 435/6 |
| 5,516,636 A | 5/1996 | McCapra | 435/6 |
| 5,516,931 A | 5/1996 | Giese | 560/59 |
| 5,536,834 A | 7/1996 | Singh | 544/98 |
| 5,560,811 A | 10/1996 | Briggs | 204/451 |
| 5,565,324 A | 10/1996 | Still | 435/6 |
| 5,567,292 A | 10/1996 | Madabhushi | 204/451 |
| 5,573,906 A | 11/1996 | Bannwarth | 435/6 |
| 5,573,909 A | 11/1996 | Singer et al. | |
| 5,578,498 A | 11/1996 | Singh | 436/518 |
| 5,580,732 A | 12/1996 | Grossman | 435/6 |
| 5,602,273 A | 2/1997 | Giese | 560/60 |
| 5,604,104 A | 2/1997 | Giese | 435/7.1 |
| 5,610,020 A | 3/1997 | Giese | 435/7.1 |
| 5,616,719 A | 4/1997 | Davalian | 546/334 |
| 5,622,929 A | 4/1997 | Willner | 514/8 |
| 5,624,800 A | 4/1997 | Grossman | 435/6 |
| 5,643,728 A | 7/1997 | Slater | 435/6 |
| 5,650,270 A | 7/1997 | Giese | 435/6 |
| 5,691,151 A | 11/1997 | Braun | 435/7.2 |
| 5,703,222 A | 12/1997 | Grossman | 536/24.3 |
| 5,705,402 A | 1/1998 | Leland et al. | |
| 5,705,622 A | 1/1998 | McCapra | 536/23.1 |
| 5,709,994 A | 1/1998 | Pease | 435/4 |
| 5,719,028 A | 2/1998 | Dahlberg | 435/6 |
| 5,721,099 A | 2/1998 | Still | 435/6 |
| 5,723,591 A | 3/1998 | Livak | 536/22.1 |
| 5,736,410 A | 4/1998 | Zarling et al. | |
| 5,756,726 A | 5/1998 | Hemmi | 540/474 |
| 5,763,602 A | 6/1998 | Li | 540/128 |
| 5,766,481 A | 6/1998 | Zambias | 210/656 |
| 5,777,096 A | 7/1998 | Grossman | 536/24.3 |
| 5,789,172 A | 8/1998 | Still | 435/6 |
| 5,807,675 A | 9/1998 | Davalian | 435/6 |
| 5,807,682 A | 9/1998 | Grossman | 435/6 |
| 5,811,239 A | 9/1998 | Frayne | 435/6 |
| 5,843,655 A | 12/1998 | McGall | 435/6 |
| 5,843,666 A | 12/1998 | Akhavan-Tafti | 435/6 |
| 5,846,703 A | 12/1998 | Devlin et al. | |
| 5,846,839 A | 12/1998 | Gallop | 436/518 |
| 5,849,878 A | 12/1998 | Cantor | 530/391.9 |
| 5,851,770 A | 12/1998 | Babon | 435/6 |
| 5,858,676 A | 1/1999 | Yang et al. | |
| 5,874,213 A | 2/1999 | Cummins | 435/6 |
| 5,876,930 A | 3/1999 | Livak | 435/6 |
| 5,898,005 A | 4/1999 | Singh | 436/527 |
| 5,916,426 A | 6/1999 | Madabhushi | 204/451 |
| 5,952,654 A | 9/1999 | Giese | 250/288 |
| 5,958,202 A | 9/1999 | Regnier | 204/451 |
| 5,981,180 A | 11/1999 | Chandler | 435/6 |
| 5,986,076 A | 11/1999 | Rothschild | 536/22.1 |
| 5,989,871 A | 11/1999 | Grossman | 435/91.1 |
| 5,998,140 A | 12/1999 | Dervan | 435/6 |
| 6,001,567 A | 12/1999 | Brow | 435/6 |
| 6,001,579 A | 12/1999 | Still | 435/7.1 |
| 6,027,890 A | 2/2000 | Ness | 435/6 |
| 6,045,676 A | 4/2000 | Mathies | 204/603 |
| 6,078,782 A | 6/2000 | Leland et al. | |
| 6,090,947 A | 7/2000 | Dervan | 548/312.4 |
| 6,251,581 B1 | 6/2001 | Ullman | 435/4 |
| 6,312,893 B1 | 11/2001 | Van Ness | 435/6 |
| 6,322,980 B1 | 11/2001 | Singh | 435/6 |
| 6,331,530 B1 | 12/2001 | Breslow | 514/58 |
| 6,335,201 B1 | 1/2002 | Allbritton | 436/63 |
| 6,346,384 B1 | 2/2002 | Pollner | 435/6 |
| 6,346,529 B1 | 2/2002 | Floyd | 514/226.2 |
| 6,649,351 B1 * | 11/2003 | Matray et al. | 435/6 |
| 2002/0037542 A1 | 3/2002 | Allbritton | 435/7.23 |
| 2002/0128465 A1 | 9/2002 | Lyamichev | 536/24.3 |

FOREIGN PATENT DOCUMENTS

| | | |
|---|---|---|
| WO | WO 93/06121 | 4/1993 |
| WO | WO 96/24061 | 8/1996 |
| WO | WO 97/27325 | 7/1997 |
| WO | WO 97/27327 | 7/1997 |
| WO | WO 97/28275 | 8/1997 |
| WO | WO 98/01533 | 1/1998 |
| WO | WO 98/15830 | 4/1998 |
| WO | WO 99/05319 | 2/1999 |
| WO | WO 99/13108 | 3/1999 |
| WO | WO 99/42838 | 8/1999 |
| WO | WO 99/64519 | 12/1999 |
| WO | WO 00/56925 | 9/2000 |
| WO | WO 00/66607 | 11/2000 |

OTHER PUBLICATIONS

Adam et al., "Photooxygenation of Vinyl Sulfides: Substituent Effects on the [2+2] Cycloaddition versus Schenck Ene Reaction Modes", Tetrahedron Letters, vol. 36, No. 43, Pergamon Press 1995, pp. 7853-7854.

Ando et al., "Photosensitized Oxygenation of Vinylic Sulphides", J.C.S. Chem. Comm., 1972, pp. 477-478.

Ando et al., "Singlet Oxygen Reaction—II Alkylthiosubstituted Ethylene[1]", Tetrahedron, vol. 29, Pergamon Press 1973, pp. 1507-1513.

Ando et al., "Singlet Oxygen Reaction. III. Solvent and Temperature Effects on the Photosensitized Oxygenation of Vinyl Sulfides and Vinyl Ethers", Journal of the American Chemical Society, vol. 96:21, 1974, pp. 6766-6768.

Ando et al., "Singlet Oxygen Reaction. IV. Photooxygenation of Enamines Involving a Two-Step Cleavage of a 1, 2-Dioxetane Intermediate[1]", Journal of American Chemical Society, vol. 97:17, 1975, pp. 5028-5029.

Ando et al., "Singlet Oxygen Reaction V. Ring Size Effects on the Decomposition of Sulfur Substituted 1, 2-Dioxetane[1]", Tetrahedron Letters, No. 47, Pergamon Press 1975, pp. 4127-4130.

Brenner et al., "Encoded Combinatorial Chemistry", Proc. Natl. Acad. Sci. USA, vol. 89, 1992, pp. 5381-5383.

Fitch et al., "Improved Methods for Encoding and Decoding Dialkylamine-Encoded Combinatorial Libraries", J. Comb. Chem., I, 1999, pp. 188-194.

Giese, "Electrophoric Release Tags: Ultrasensitive Molecular Labels Providing Multiplicity", Trends in Analytical Chemistry, vol. 2, No. 7, 1983, pp. 166-168.

Gomer, "Preclinical Examination of First and Second Generation Photosensitizers Used in Photodynamic Therapy", Photochemistry and Photobiology, vol. 54, No. 6, 1991, pp. 1093-1107.

Hacia et al., "Detection of Heterozygous Mutations in BRCA1 Using High Density Oligonucleotide Arrays and Two-Colour Fluorescence Analysis", Nature Genetics, vol. 14, 1996, pp. 441-447.

Haff et al., "Multiplex Genotyping of PCR Products with MassTag-Labled Primers", Nucleic Acids Research, vol. 25, No. 18, 1997, pp. 3749-3750.

Holland et al., "Detection of Specific Polymerase Chain Reaction Product by Utilizing the 5'→3' Exonuclease Activity of *Thermus Aquaticus* DNA Polymerase", Proc. Natl. Acad. Sci. USA, vol. 88, 1991, pp. 7276-7280.

Houghten et al., "Human β -Endorphin: Synthesis and Characterization of Analogs Iodinated and Tritiated at Tryosine Residues 1 and 27", Int. J. Peptide Protein Res., vol. 16, 1980, pp. 311-320.

Kochevar et al., "Photosensitized Production of Singlet Oxygen", Methods in Enzymology, vol. 319, 2000, pp. 20-29.

Lee et al., "Allelic Discrimination by Nick-Translation PCR with Fluorogenic Probes", Nucleic Acids Research, vol. 21, No. 16, 1993, pp. 3761-3766.

Liu et al., "Capillary Electrochromatography-laser-induced Fluorescence Method for Separation and Detection of Dansylated Dialkylamine Tags in Encoded Combinatorial Libraries", Journal of Chromatorgraphy, Art. 924, 2001, pp. 323-329.

Lu et al., "Polymerizable Fab' Antibody Fragments for Targeting of Anticancer Drugs", Nature Biotechnology, vol. 17, 1999, pp. 1101-1104.

Lum et al., "Ability of Specific Monoclonal Antibodies and Conventional Antisera Conjugated to Hematoporphyrin to Label and Kill Selected Cell Lines Subsequent to Light Activation", Cancer Research, vol. 45, 1985, pp. 4380-4386.

Marglin et al., "Chemical Synthesis of Peptides and Proteins", Art. 739, 1970, pp. 841-866.

Marino et al., "Characterization of Mitochondrial DNA Using Low-Stringency Single Specific Primer Amplification Analyzed by Laser Induced Fluoroscene—Capillary Electrophoresis", Electrophoresis, vol. 17, 1996, pp. 1499-1504.

Matthews et al., "Analytical Strategies for the Use of DNA Probes", Analytical Biochemistry, vol. 169, 1988, pp. 1-25.

Merrifield, "Solid Phase Peptide Synthesis. I. The Synthesis of a Tetrapeptide", Synthesis of a Tetrapeptide, vol. 85, 1963, pp. 2149-2154.

Ni et al., "Versatile Approach to Encoding Combinatorial Organic Synthesis Using Chemically Robust Secondary Amine Tags", J. Med. Chem., vol. 39, 1996, pp. 1601-1608.

Olejnik et al., "Photocleavable Affinity Tags for Isolation and Detection of Biomolecules", Methods in Enzymology, vol. 291, 1998, pp. 135-154.

Oseroff et al., "Antibody-Targeted Photolysis: Selective photodestruction of Human T-Cell Leukemia Cells Using Monoclonal Antibody-Chlorin $e_6$ Conjugates", Proc. Natl. Acad. Sci. USA, vol. 83, 1986, pp. 8744-8748.

Pastinen et al., "Multiplex, Fluorescent, Solid-Phase Minisequencing for Efficient Screening of DNA Sequence Variation", Clinical Chemistry, vol. 42:9, 1996, pp. 1391-1397.

Posewitz et al., "Immobilized Gallium(III) Affinity Chromatography of Phosphopeptides", Anal. Chem., vol. 71, 1999, pp. 2883-2892.

Rakestraw et al., "Antibody-Targeted photolysis: *In vitro* Studies with Sn(IV) Chlorin $e_6$ Covalently Bound to Monoclonal Antibodies Using a Modified Dextran Carrier", Proc. Natl. Acad. Sci. USA, vol. 87, 1990, pp. 4217-4221.

Da Ros et al., "DNA-Photocleavage Agents", Current Pharmaceutical Design, vol. 7, 2001, pp. 1781-1821.

Ross et al., "Discrimination of Single-Nucleotide Polymorphisms in Human DNA Using Peptide Nucleic Acid Probes Detected by MALDI-TOF Mass Spectrometry", Anal. Chem., vol. 69, 1997, pp. 4197-4202.

Sharman et al., "Role of Activated Oxygen Species in Photodynamic Therapy", Methods in Enzymology, vol. 319, 2000, pp. 376-400.

Still, "Discovery of Sequence-Selective Peptide Binding by Synthetic Receptors Using Encoded Combinatorial Libraries", Acc. Chem. Res., vol. 29, 1996, pp. 155-163.

Strong, "Antibody-Targeted Photolysis", Annals New York Academy of Sciences, vol. 745, 1994, pp. 297-320.

Ullman et al., "Luminescent Oxygen Channeling Immunoassay: Measurement of Particle Binding Kinetics by Chemiluminescence", Proc. Natl. Acad. Sci. USA, vol. 91, 1994, pp. 5426-5430.

Wang et al., "Large-Scale Identification, Mapping, and Genotyping of Single-Nucleotide Polymorphisms in the Human Genome", Science, vol. 280, 1998, pp. 1077-1082.

Wasserman et al., "Enamine-Single Oxygen Reactions. α-Diketones from Intermediate Amino Dioxetanes", Tetrahedron Letters, No. 21, 1975, pp. 1735-1738.

Wetmur, "DNA Probes: Applications of the Principles of Nucleic Acid Hybridization", Critical Reviews in Biochemistry and Molecular Biology, vol. 26, 1991, pp. 227-259.

White, "The Future of PCR Technology: Diversification of Technologies and Applications", Tibtech, vol. 14, 1996, pp. 478-483.

Wöhrle, "Porphyrins, Phthalocyanines, and Naphthalocyanines for Various Processes fo Visible Light Driven Conversion Processes", Chimia, vol. 45, 1991, pp. 307-310.

Woolley et al., "Functional Integration of PCR Amplification and Capillary Electrophoresis in a Microfabricated DNA Analysis Device", Anal. Chem., vol. 68, 1996, pp. 4081-4086.

Yarmush et al., "Antibody Targeted Photolysis", Critical Reviews in Therapeutic Drug Carrier Systems, vol. 10, 1993, pp. 197-252.

Yemul et al., "Selective Killing of T Lymphocytes by Phototoxic Liposomes", Proc. Natl. Acad. Sci. USA, vol. 84, 1987, pp. 246-250.

Zaklika et al., "Mechanisms of 1,2-Dioxetane Decomposition: The Role of Electron Transfer", Photochemistry and Photobiology, vol. 30, 1979, pp. 35-44.

Beaudet et al., "Homogeneous Assays for Single-Nucleotide Polymorphism Typing Using AplhaScreen", Genome Research, 11-600-608.

Bangs Laboratories, Inc., "Working with Microspheres", Tech Note #201, Rev. #001, Active: Aug. 29, 1999, pp. 1-16.

\* cited by examiner

Thiazole cleavable linkage

Oxazole cleavable linkage

Olefin cleavable linkage

Thioether cleavable linkage

Pro1-NHS

Pro2-NHS

Pro3-NHS

Pro4-NHS

Pro5-NHS

Pro6-NHS

Pro7-NHS

Pro8-NHS

Pro9-NHS

Pro10-NHS

Pro11-NHS

Pro12-NHS

Pro13-NHS

Pro14-NHS

Pro15-NHS

Pro16-NHS

Pro17-NHS

Pro18-NHS

Pro19-NHS

Pro20-NHS

Pro21-NHS

Pro22-NHS

Pro23-biotin

Pro24-biotin

Pro25-biotin

Pro26-biotin

Pro27-biotin

Pro28-NHS

Pro28-biotin

Pro29-NHS

Pro29-biotin

Pro30-NHS

Pro30-biotin

Pro31-NHS

Pro32-NHS

Pro32-biotin

Pro33-NHS

Pro33-biotin

Synthesis of Pro15

Synthesis of Pro22

Synthesis of Pro28

TAGGED MICROPARTICLE COMPOSITIONS AND METHODS

CROSS-REFERENCE TO RELATED APPLICATIONS AND PATENTS

This application claims priority from U.S. provisional application Ser. No. 60/337,768 filed 9 Nov. 2001 and is a continuation-in-part of co-pending U.S. application Ser. No. 10/154,042 filed 21 May 2002 which is a continuation-in-part of co-pending U.S. application Ser. No. 09/698,846 filed 27 Oct. 2000, now U.S. Pat. No. 6,627,400 which is a continuation-in-part of co-pending U.S. application Ser. No. 09/602,586 filed 21 Jun., 2000 now U.S Pat. No. 6,514,700 and U.S. application Ser. No. 09/684,386 filed 04 Oct. 2000 (now abandoned), which are both continuations-in-parts of co-pending U.S. application Ser. No. 09/561,579 filed 28 Apr. 2000, now U.S. Pat. No. 6,682,887 all of which are incorporated herein by reference in their entirety.

FIELD OF THE INVENTION

This invention relates to methods and compositions for detecting and/or measuring multiple analytes in a sample using microparticle-bound binding pairs with releasable molecular tags.

BACKGROUND OF THE INVENTION

The development of several powerful technologies for genome-wide and proteome-wide expression measurements has created an opportunity to study and understand the coordinated activities of large sets of, if not all, an organism's genes in response to a wide variety of conditions and stimuli, e.g. DeRisi et al, Science, 278: 680–686 (1997); Wodicka et al, Nature Biotechnology, 15: 1359–1367 (1997); Velculescu et al, Cell, 243–251 (1997); Brenner et al, Nature Biotechnology, 18: 630–634 (2000); McDonald et al, Disease Markers, 18: 99–105 (2002); Patterson, Bioinformatics, 18 (Suppl 2): S181 (2002). Studies using these technologies have shown that reduced subsets of genes appear to be co-regulated to perform particular functions and that subsets of expressed genes and proteins can be used to classify cells phenotypically, e.g. Shiffman and Porter, Current Opinion in Biotechnology, 11: 598–601 (2000); Afshari et al, Nature, 403: 503–511 (2000); Golub et al, Science, 286: 531–537 (1999); van't Veer et al, Nature, 415: 530–536 (2002); and the like.

An area of interest in drug development is the expression profiles of genes and proteins involved with the metabolism or toxic effects of xenobiotic compounds. Several studies have shown that sets of several tens of genes can serve as indicators of compound toxicity, e.g. Thomas et al, Molecular Pharmacology, 60: 1189–1194 (2001); Waring et al, Toxicology Letters, 120: 359–368 (2001); Longueville et al, Biochem. Pharmacology, 64: 137–149 (2002); and the like. Similarly, in the area of cancer diagnostics and prognosis, the differential expression of sets of a few tens of genes or proteins has been shown frequently to have strong correlations with the progression and prognosis of a cancer.

Accordingly, there is an interest in technologies that provide convenient and accurate measurements of multiple expressed genes in a single assay, either at the messenger RNA level or the protein level, or both. Current approaches to such measurements include multiplexed polymerase chain reaction (PCR), spotted and synthesized DNA microarrays, color-coded microbeads, and single-analyte assays, such as enzyme-linked immunosorbant assays (ELISAs) or Taqman-based PCR, used with robotics apparatus, e.g. Longueville et al (cited above); Elnifro et al, Clinical Microbiology Reviews, 13: 559–570 (2000); Chen et al, Genome Research, 10: 549–557 (2000); and the like. Unfortunately, none of the approaches provides a completely satisfactory solution for the desired measurements for several reasons including difficulty in automating, reagent usage, sensitivity, consistency of results, and so on, e.g. Elnifro et al (cited above); Hess et al, Trends in Biotechnology, 19: 463–468 (2001); King and Sinha, JAMA, 286: 2280–2288 (2001).

In view of the above, the availability of a convenient and cost effective technique for measuring the presence or absence or quantities of multiple analytes, such as gene expression products, in a single assay reaction would advance the art in many fields where such measurements are becoming increasingly important, including life science research, medical research and diagnostics, drug discovery, genetic identification, animal and plant science, and the like.

SUMMARY OF THE INVENTION

The present invention is directed to methods and compositions for determining the presence and/or amount of one or more target analytes in a sample using microparticles derivatized with a plurality of releasable molecular tags that have distinct separation characteristics.

In one aspect, the invention includes a composition comprising a mixture of more than one microparticle, each microparticle in the mixture having molecular tags attached by cleavable linkages such that different molecular tags are attached to different microparticles, the molecular tags being selected from a plurality of molecular tags such that each molecular tag of the plurality has one or more physical and/or optical characteristics distinct from those of the other molecular tags of the plurality so that each molecular tag forms a distinguishable peak upon cleavage and separation based on such one or more physical and/or optical characteristics.

In another aspect, the invention includes a composition comprising: (i) a mixture of more than one microparticle, each microparticle having a surface with binding moieties and molecular tags attached, each binding moiety being specific for a predetermined analyte and the molecular tags being attached by cleavable linkages, such that different pairs of molecular tags and binding moieties are attached to different microparticles, the molecular tags being selected from a plurality of molecular tags such that each molecular tag of the plurality has one or more physical and/or optical characteristics distinct from those of the other molecular tags of the plurality so that each molecular tag forms a distinguishable peak upon cleavage and separation based on such one or more physical and/or optical characteristics; and (ii) a second binding composition comprising at least one binding moiety specific for each of the predetermined analytes, each such binding moiety having a sensitizer for generating an active species capable of cleaving the cleavable linkage.

In yet another aspect, the invention provides methods of using the above compositons to determine the presence or absence or quantities of multiple target analytes in a sample. Such methods comprise the steps of (i) combining with a sample a mixture of microparticles and a second binding composition such that in the presence of a target analyte a complex is formed between the target analyte and at least one first binding moiety and at least one second binding moiety specific therefor, and such that the sensitizer of the second binding moiety causes the generation of an active species and the cleavage of one or more cleavable linkages to release one or more molecular tags from at least one microparticle; and (ii) separating and identifying the released molecular tags by the one or more physical and/or optical characteristics to determine the target analytes in the sample.

In another aspect, the present invention includes kits for performing the methods of the invention, such kits comprising a mixture of microparticles for detecting or measuring the quantities of each of one or more target analytes. Such kits further comprise a cleavage agent and appropriate buffers for cleaving the cleavable linkages between molecular tags and binding moieties that form stable complexes with a target analyte. Such kit futher comprise separation standards for aiding in making quantitative measurements of the separated molecular tags.

In another aspect, compositions of the invention may be used as identifying agents, or taggants, for monitoring or tracking materials or products including natural resources such as animals, plants, oil, minerals, and water; chemicals such as drugs, solvents, petroleum products, and explosives; commercial by-products including pollutants such as radioactive or other hazardous waste; and articles of manufacture such as guns, typewriters, automobiles and automobile parts. In this aspect, a composition of the invention comprising a plurality of microparticles each coated with a different kind of releaseable molecular tag is incorporated or added to a material to be tracked and/or identified.

The present invention provides a detection and signal generation means with several advantages for multiplexed measurements of target analytes, including but not limited to (1) the detection and/or measurement of molecular tags that are separated from the assay mixture provide greatly reduced background and a significant gain in sensitivity; (2) the use of tags that are specially designed for ease of separation thereby providing convenient multiplexing capability; (3) providing greater sensitivity by attaching analyte binding moieties to solid phase supports, and (4) providing increased numbers of molecular tags released per analyte detection event by use of microparticle supports.

DEFINITIONS

Figure 1:
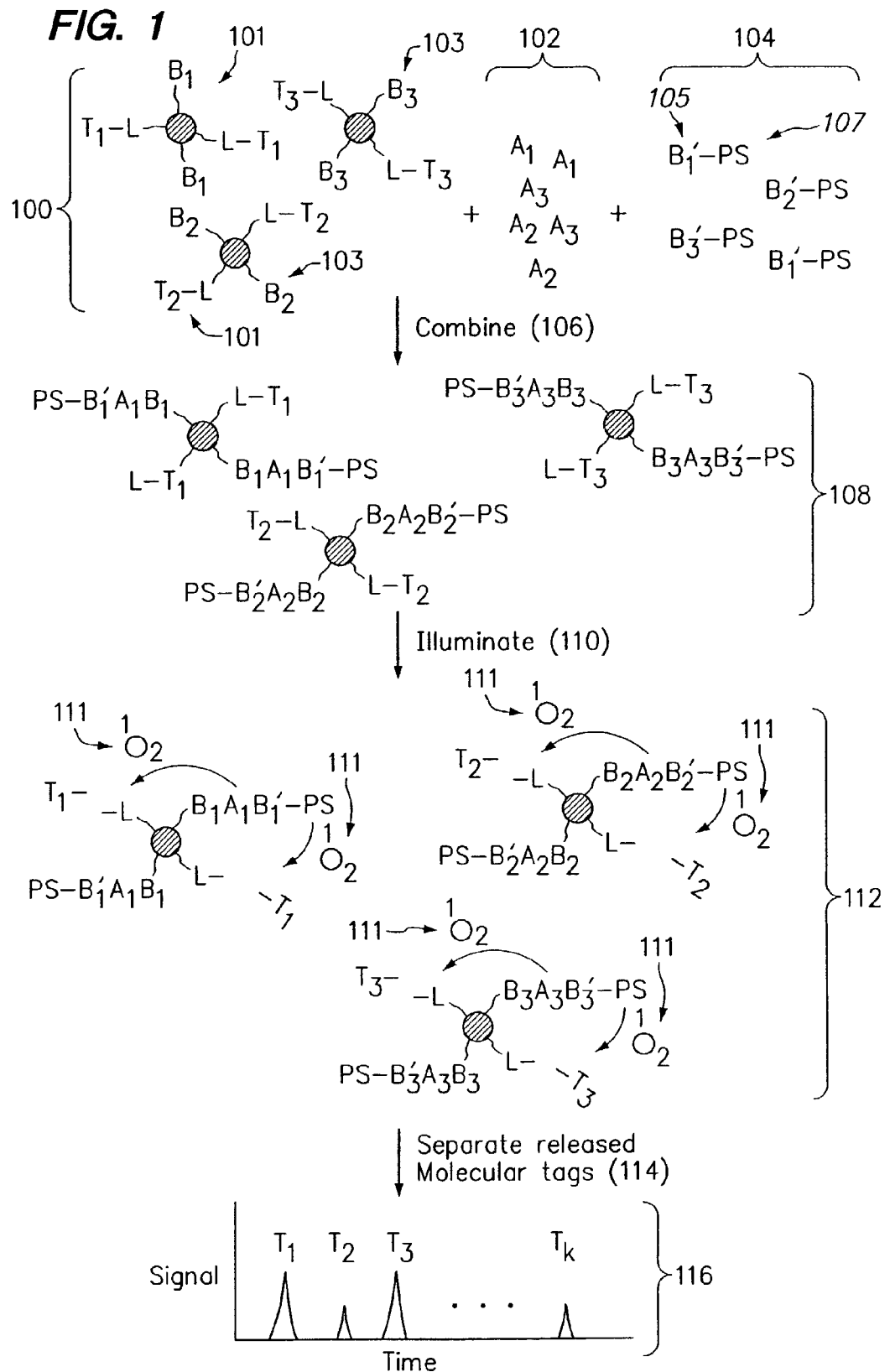
FIG. 1 illustrates a method of using the compositions of the invention to detect multiple analytes.

"Analyte" means a substance, compound, or component in a sample whose presence or absence is to be detected or whose quantity is to be measured. Analytes include but are not limited to peptides, proteins, polynucleotides, polypeptides, oligonucleotides, organic molecules, haptens, epitopes, parts of biological cells, posttranslational modifications of proteins, receptors, complex sugars, vitamins, hormones, and the like. There may be more than one analyte associated with a single molecular entity, e.g. different phosphorylation sites on the same protein.

"Antibody" means an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular polypeptide is maintained.

"Antibody binding composition" means a molecule or a complex of molecules that comprise one or more antibodies and derives its binding specificity from an antibody. Antibody binding compositions include, but are not limited to, antibody pairs in which a first antibody binds specifically to a target molecule and a second antibody binds specifically to a constant region of the first antibody; a biotinylated antibody that binds specifically to a target molecule and streptavidin derivatized with moieties such as molecular tags or photosensitizers; antibodies specific for a target molecule and conjugated to a polymer, such as dextran, which, in turn, is derivatized with moieties such as molecular tags or photosensitizers; antibodies specific for a target molecule and conjugated to a bead, or microbead, or other solid phase support, which, in turn, is derivatized with moieties such as molecular tags or photosensitizers, or polymers containing the latter.

"Capillary-sized" in reference to a separation column means a capillary tube or channel in a plate or microfluidics device, where the diameter or largest dimension of the separation column is between about 25–500 microns, allowing efficient heat dissipation throughout the separation medium, with consequently low thermal convection within the medium.

"Chromatography" or "chromatographic separation" as used herein means or refers to a method of analysis in which the flow of a mobile phase, usually a liquid, containing a mixture of compounds, e.g. including analytes, promotes the separation of such compounds by a differential distribution between the mobile phase and a stationary phase, usually a solid.

A "separation profile" in reference to the separation of molecular tags means a chart, graph, curve, bar graph, or other representation of signal intensity data versus time, or other variable related to time, that provides a readout, or measure, of the number of molecular tags of each type produced in an assay. A separation profile may be an electropherogram, a chromatogram, an electrochromatogram, or like graphical representations of data depending on the separation technique employed. A "peak" or a "band" or a "zone" in reference to a separation profile means a region where a separated compound is concentrated. There may be multiple separation profiles for a single assay if, for example, different molecular tags have different fluorescent labels having distinct emission spectra and data is collected and recorded at multiple wavelengths.

"Microparticles" as used herein means solid phase particulate supports to which molecular tags can be covalently attached and/or to which binding moieties, such as antibodies, can be covalently, or in some embodiments, non-covalently attached. Such particulate supports are small-sized to provide large surface area-to-volume ratios and are monodisperse under assay conditions. Microparticles may vary widely in size, shape, and composition. In one aspect, microparticles are uniformly sized microspheres having a diameter in the range of from a few tens of nanometers to several tens of micrometers, e.g. in the range of from 20 nm to 50 µm, or from 0.5 µm to 25 µm, or from 1 µm to 10 µm. Typically, diameters of populations of uniformly sized microparticles have a coeffient of variation of less than ten percent. In one aspect, microparticles are are mechanically rigid and substantially non-swellable under assay conditions. In another aspect, microparticles are non-porous. Microparticles may be made from a variety of materials including polymers, such as polystyrene, polymethylacrylate, glycidal methacrylate, nylon, or the like, or minerals, such as silica, alumina, or the like. In another aspect, microparticles include colloidal particles, dentrimers, liposomes, and other non-rigid particle-like supports, e.g. Hermanson, Bioconjugate Techniques (Academic Press, New York, 1996); Frechet, Science, 263: 1710–1705 (1994); Klajnert et al, Acta. Biochim. Pol., 48: 199–208 (2001); Singh et al, Clinical Chemistry, 40: 1845–1849 (1994); and the like. Microparticles further include magnetic microbeads, e.g. Dynadeads™, as disclosed in U.S. Pat. Nos. 4,186,120; 4,530,956; 4,563,510; and 4,654,267.

"Specific" or "specificity" in reference to the binding of one molecule to another molecule, such as a probe for a target polynucleotide, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, ionic and hydrophobic interactions, and the like, dominate the interaction of the molecules. As used herein, "stable complex" in reference to two or more molecules means that such molecules form noncovalently linked aggregates, e.g. by specific binding, that under assay conditions are thermodynamically more favorable than a non-aggregated state.

As used herein, the term "spectrally resolvable" in reference to a plurality of fluorescent labels means that the fluorescent emission bands of the labels are sufficiently distinct, i.e. sufficiently non-overlapping, that molecular tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558; 4,811,218, or the like, or in Wheeless et al, pgs. 21–76, in Flow Cytometry: Instrumentation and Data Analysis (Academic Press, New York, 1985).

"Oligonucleotide" as used herein means linear oligomers of natural or modified nucleosidic monomers linked by phosphodiester bonds or analogs thereof. Oligonucleotides include deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several tens of monomeric units, e.g. 40–60. Whenever an oligonucleotide is represented by a sequence of letters, such as "ATGCCTG," it will be understood that the nucleotides are in 5'□3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides of the invention comprise the four natural deoxynucleotides; however, they may also comprise ribonucleosides or non-natural nucleotide analogs. It is clear to those skilled in the art when oligonucleotides having natural or non-natural nucleotides may be employed in the invention. For example, where processing by an enzyme is called for, usually oligonucleotides consisting of natural nucleotides are required. Likewise, where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding. As used herein, "stable duplex" between complementary oligonucleotides or polynucleotides means that a significant fraction of such compounds are in duplex or double stranded form with one another as opposed to single stranded form. Preferably, such significant fraction is at least ten percent of the strand in lower concentration, and more preferably, thirty percent.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce complexity, increase specificity, and the like.

A probe is "capable of hybridizing" to a nucleic acid sequence if at least one region of the probe shares substantial sequence identity with at least one region of the complement of the nucleic acid sequence. "Substantial sequence identity" is a sequence identity of at least about 80%, preferably at least about 85%, more preferably at least about 90%, and most preferably 100%. It should be noted that for the purpose of determining sequence identity of a DNA sequence and a RNA sequence, U and T are considered the same nucleotide. For example, a probe comprising the sequence ATCAGC is capable of hybridizing to a target RNA sequence comprising the sequence GCUGAU.

"Normal phase" in reference to chromatographic separation means that separation operates on the basis of hydrophilicity and lipophilicity by using a polar stationary phase and a less polar mobile phase. Thus hydrophobic compounds elute more quickly than do hydrophilic compounds. Exemplary groups on a solid phase for normal phase chromatography are amine (—$NH_2$) and hydroxyl (—OH) groups.

"Reverse phase" in reference to chromatographic separation means that separation operates on the basis of hydrophilicity and lipophilicity. The stationary phase usually consists of silica based packings with n-alkyl chains or phenyl groups covalently bound. For example, C-8 signifies an octyl chain and C-18 an octadecyl ligand in the matrix. The more hydrophobic the matrix on each ligand, the greater is the tendancy of the column to retain hydrophobic moieties. Thus hydrophilic compounds elute more quickly than do hydrophobic compounds.

"Ion-exchange" in reference to chromatographic separation means that separation operates on the basis of selective exchange of ions in the sample with counterions in the stationary phase. Ion exchange is performed with columns containing charge-bearing functional groups attached to a polymer matrix. The functional ions are permanently bonded to the column and each has a counterion attached. The sample is retained by replacing the counterions of the stationary phase with its own ions. The sample is eluted from the column by changing the properties of the mobile phase do that the mobile phase will now displace the sample ions from the stationary phase, (ie. changing the pH).

As used herein, the term "Tm" is used in reference to the "melting temperature." The melting temperature is the temperature at which a population of double-stranded nucleic acid molecules becomes half dissociated into single strands. Several equations for calculating the Tm of nucleic acids are well known in the art. As indicated by standard references, a simple estimate of the T, value may be calculated by the equation. Tm=81.5+0.4 1 (% G+C), when a nucleic acid is in aqueous solution at I M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581–94 (1997)) include alternative methods of computation which take structural and environmental, as well as sequence characteristics into account for the calculation of Tm.

The term "sample" in the present specification and claims is used in a broad sense. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "isothermal" in reference to assay conditions means a uniform or constant temperature at which the cleavage of the binding compound in accordance with the present invention is carried out. The temperature is chosen so that the duplex formed by hybridizing the probes to a polynucleotide with a target polynucleotide sequence is in equilibrium with the free or unhybridized probes and free or unhybridized target polynucleotide sequence, a condition that is otherwise referred to herein as "reversibly hybridizing" the probe with a polynucleotide. Normally, at least 1%, preferably 20 to 80%, usually less than 95% of the polynucleotide is hybridized to the probe under the isothermal conditions. Accordingly, under isothermal conditions there are molecules of polynucleotide that are hybridized with the probes, or portions thereof, and are in dynamic equilibrium with molecules that are not hybridized with the probes. Some fluctuation of the temperature may occur and still achieve the benefits of the present invention. The fluctuation generally is not necessary for carrying out the methods of the present invention and usually offer no substantial improvement. Accordingly, the term "isothermal" includes the use of a fluctuating temperature, particularly random or uncontrolled fluctuations in temperature, but specifically excludes the type of fluctuation in temperature referred to as thermal cycling, which is employed in some known amplification procedures, e.g., polymerase chain reaction.

As used herein, the term "kit" refers to any delivery system for delivering materials. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Polypeptide" refers to a class of compounds composed of amino acid residues chemically bonded together by amide linkages with elimination of water between the carboxy group of one amino acid and the amino group of another amino acid. A polypeptide is a polymer of amino acid residues, which may contain a large number of such residues. Peptides are similar to polypeptides, except that, generally, they are comprised of a lesser number of amino acids. Peptides are sometimes referred to as oligopeptides. There is no clear-cut distinction between polypeptides and peptides. For convenience, in this disclosure and claims, the term "polypeptide" will be used to refer generally to peptides and polypeptides. The amino acid residues may be natural or synthetic.

"Protein" refers to a polypeptide, usually synthesized by a biological cell, folded into a defined three-dimensional structure. Proteins are generally from about 5,000 to about 5,000,000 or more in molecular weight, more usually from about 5,000 to about 1,000,000 molecular weight, and may include posttranslational modifications, such acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, phosphorylation, prenylation, racemization, selenoylation, sulfation, and ubiquitination, e.g. Wold, F., Post-translational Protein Modifications: Perspectives and Prospects, pgs. 1–12 in Post-translational Covalent Modification of Proteins, B. C. Johnson, Ed., Academic Press, New York, 1983. Proteins include, by way of illustration and not limitation, cytokines or interleukins, enzymes such as, e.g., kinases, proteases, galactosidases and so forth, protamines, histones, albumins, immunoglobulins, scleroproteins, phosphoproteins, mucoproteins, chromoproteins, lipoproteins, nucleoproteins, glycoproteins, T-cell receptors, proteoglycans, unclassified proteins, e.g., somatotropin, prolactin, insulin, pepsin, proteins found in human plasma, blood clotting factors, blood typing factors, protein hormones, cancer antigens, tissue specific antigens, peptide hormones, nutritional markers, tissue specific antigens, and synthetic peptides.

DETAILED DESCRIPTION OF THE INVENTION

In one aspect, the present invention is directed to methods and compositions for determining the presence and/or amount of one or more analytes in a sample by releasing microparticle-bound molecular tags as the result of a binding reaction. The binding reaction is between analytes and binding moieties operationally associated with the microparticle-bound molecular tags. Usually, a binding moiety is operationally associated with a particular species of molecular tag by being attached to the same microparticle. In one embodiment, such a binding moiety binds to an analyte together with a second binding moiety having a sensitizer attached. Such a binding event brings molecular tags on the microparticle into the effective proximity of the sensitizer. When a target analyte is a polynucleotide, both binding moieties comprise oligonucleotides specific for such polynucleotide. When a target analyte is a protein, or other analyte having a molecular weight greater than about 4–6000 daltons, the binding moieties may both be antibody binding compositions. When a target analyte is a surface membrane receptor of a biological cell, the binding moiety attached to the microparticle is a ligand or candidate ligand for the receptor. In the later embodiment, a sensitizer may be a lipid-photosensitizer conjugate disposed in the same membrane as the receptor.

Methods using compositions of the invention may be operated in either a homogeneous or a heterogeneous format. One embodiment of a homogeneous format is illustrated in FIG. 1. Mixture (100) of microparticles derivatized with molecular tags ("$T_1$", "$T_2$", "$T_3$") (101) and first binding moieties ("$B_1$", "$B_2$", "$B_3$") (103) are combined (106) with target analytes ("$A_1$", "$A_2$", "$A_3$") (102) and second binding composition ("$B_k'$-PS") (104) comprising conjugates of first binding moieties (105) and photosensitizers ("PS") (107). Assay conditions are selected so that complexes (108) form among the first and second binding moieties and target analytes. After an incubation period to allow such complexes to form, the assay mixture is subjected to illumination (110) by light that excites photosensitizers (107) so that they react with molecular oxygen to produce singlet oxygen (111) that, in turn, reacts with cleavable linkages ("L") (113) to release molecular tag (101). Such incubation period can vary from a few minutes, e.g. 15 min, to several hours, e.g. 2 hours, 4 hours, 8 hours, to overnight, depending on the nature of the binding moieties and analytes. Released molecular tags are then separated from the assay mixture and from one another (114) to produce separation profile (116) from which the presence, absence, and/or quantities of target analytes are determined.

A heterogeneous format may be desirable whenever sensitizers are either long-lived molecular entities or act throughout the entire reaction mixture rather than in a limited region, e.g. light when the cleavable linkages are photo-cleavable, acid when the cleavable linkages are acid labile, etc. In such embodiments, after formation, microparticles containing complexes (108) are separated from microparticles lacking such complexes, after which they treated as described above.

As described more fully below, target analytes are determined by separation and identification of the released molecular tags. A wide variety of separation techniques may be employed that can distinguish molecules based on one or more physical, chemical, or optical differences among molecules being separated including but not limited to electrophoretic mobility, molecular weight, shape, solubility, pKa, hydrophobicity, charge, charge/mass ratio, polarity, or the like. In one aspect, molecular tags in a plurality differ in electrophoretic mobility and optical detection characteristics and are separated by electrophoresis. In another aspect, molecular tags in a plurality differ in molecular weight, shape, solubility, pKa, hydrophobicity, charge, polarity, and are separated by normal phase or reverse phase HPLC, ion exchange HPLC, capillary electrochromatography, or like technique.

Another aspect of the present invention is providing sets of molecular tags that may be separated into distinct bands or peaks by the separation technique employed after they are released from microparticles. Molecular tags within a set may be chemically diverse; however, for convenience, sets of molecular tags are usually chemically related. For example, they may all be peptides, or they may consist of different combinations of the same basic building blocks or monomers, or they may be synthesized using the same basic scaffold with different substituent groups for imparting different separation characteristics, as described more fully below. The number of molecular tags in a plurality may vary depending on several factors including the mode of separation employed, the labels used on the molecular tags for detection, the sensitivity of the binding moieties, the efficiency with which the cleavable linkages are cleaved, and the like. In one aspect, the number of molecular tags in a plurality ranges from 2 to several hundred, e.g. 200. In other aspects, the size of the plurality may be in the range of from 5 to 100, and more usually, in the range of from 5 to 50, or in the range of from 5 to 30, or in the range of from 5 to 20.

Microparticle Supports for Molecular Tags and Binding Moieties

In one aspect, compositions of the invention comprise mixtures of microparticles having molecular tags covalently attached by way of cleavable linkages. Usually, each microparticle has only one kind of molecular tag attached, so that different molecular tags are attached to different microparticles; however, in some embodiments, two or more different kinds of molecular tag may be attached to the same microparticle. Compositions of the invention also comprise mixtures of microparticles having both molecular tags covalently attached by cleavage linkages and binding moieties attached either covalently or non-covalently. As above, usually when both molecular tags and binding moieties are attached to microparticles, only pairs of a single kind of molecular tag and a single kind of binding moiety are attached to the same microparticle; thus, different molecular tag-binding moiety pairs are attached to different microparticles. The ratio of molecular tags to binding moieties on a microparticle is readily varied by one of ordinary skill in the art and depends on the requirements of a particular assay. Other embodiments of the invention include combinations of multiple molecular tags and/or multiple binding moieties on single microparticles. Making compositions of the invention based on such embodiments are design choices available to one of ordinary skill in the art depending on the requirements of a particular assay.

Microparticles for use with the invention may be derivatized with many different functional groups that permit the covalent attachment of molecular tags and/or binding moieties. Such functional groups include but are not limited to amino, carboxyl, hydroxyl, hydrazide, chloromethyl, silanol, and the like. Molecular tags are attached by reacting a functional group on the microparticles with a complementary functionality on a precursor of the molecular tag. For example, carboxyl-modified microparticles may be coupled to an amino complementary functionality of a molecular tag via a water soluble carbodiimide cross-linking agent, amino-modified microparticles may be coupled to an amino complementary functionality of a molecular tag via a glutaraldehyde cross-linking agent, hydroxyl-modified microparticles may be coupled to an amino complementary functionality of a molecular tag via cyanogens bromide, and the like. Extensive guidance can be found in the literature for covalently linking molecular tags and binding moieties, such as antibodies, to microparticles, e.g. Bangs Labortories (Fishers, Ind.) Technical Note 205 (30 Mar. 2002); Hermanson, Bioconjugate Techniques, (Academic Press, New York, 1996), and the like.

In one aspect, carboxyl-derivatized microparticles (many sizes and varieties available from Bangs Laboratories, Fishers, Ind.) are treated with a polymeric carrier molecules, such as polylysine, aminodextran, or the like, to create an amino derivatized surface for reacting with complementary functionalities of molecular tags and/or binding moieties. Preferably, carboxyl-derivatized microparticles are treated with aminodextran to prepare their surfaces for reaction with amine-reactive groups on molecular tags and/or binding moieties, e.g. as disclosed by Pollner, U.S. Pat. No. 6,346,384; and Patel, International patent publication WO 01/90399; both of which are incorporated by reference.

In one aspect of the invention, molecular tags and antibodies are attached to amino derivatized microparticles, e.g. hydroxypropylaminodextran coated microspheres, as described below. Preferably, attachment is done in a two step process. In the first stage, a mixture of NHS-ester of a molecular tag and an NHS-ester cross-linking agent are reacted with the free amines on the microparticle. The proportion of each compound in the mixture depends on several factors including the proportion of molecular tag to antibody that is desired on the surface of the microparticle, relative reaction rates, efficiency of the reaction of the second stage of the process, and the like. Numerous suitable cross linking agents may be used including but not limited to succinimidyl 6-((iodoacetyl)amino)hexanoate (SIAX), succinimidyl 6-[6-(((iodoacetyl)amino)-hexanoyl)amino]hexanoate (SIAXX), N-succinimidyl 3-(2-pyridyldithio)propionate (SPDP), and like compounds well known in the art, e.g. Hermanson (cited above); Haugland, Handbook of Fluorescent Probes and Research Products, Ninth Edition (Molecular Probes, Eugene, Oreg., 2002). In the second stage, an appropriately derivatized antibody binding moiety is reacted with the other functionality of the cross-linking agent, such as the iodoacetyl group of SIAX. By way of example, for such a reaction, an amino group of an antibody binding moiety may be converted to a sulfhydryl group by treatment with N-succinimidyl-S-acetylthioacetate (SATA), e.g. Hermanson (cited above).

In another aspect of the invention, molecular tags and binding moieties are attached to microparticles by providing biotinylated forms of molecular tags and binding moieties and avidinated microparticles. A mixture of biotinylated molecular tags and biotinylated binding moieties, such as antibodies, can then be combined with the avidinated microparticle for attachment. Binding moieties such as antibodies, fragments thereof, or other proteins, are readily biotinylated using commercial reagents, e.g. NHS-esters of biotin (Pierce Chemical Co.).

In yet another aspect, molecular tags and oligonucleotides are attached to amino derivatized microparticles, e.g. hydroxypropylaminodextran coated microspheres, as described in Pollner (cited above); Patel (cited above); or Beaudet et al, Genome Research, 11: 600–608 (2001); which are incorporated by reference for this teaching.

Once microparticles are separately derivatized by a plurality of different molecular tags and/or binding moieties they are pooled to produce the compositions of the invention. Usually, each different kind of microparticle is present in a composition in the same proportion; however, proportions may be varied as a design choice so that one or a subset of particular microparticles are present in greater or lower proportion depending on the desirability or requirements for a particular embodiment or assay.

Molecular Tags and Cleavable Linkages

In one embodiment, molecular tags are cleaved from a microparticle by reaction of a cleavable linkage with an active species, such as singlet oxygen, generated by a cleavage-inducing moiety, e.g. Singh et al, International patent publication WO 01/83502. A cleavable linkage can be virtually any chemical linking group that may be cleaved under conditions that do not degrade the structure or affect detection characteristics of the released molecular tag. Whenever compositions of the invention are used in a homogeneous assay format, the cleavable linkage holding a molecular tag to a microparticle is cleaved by a cleavage agent that acts over a short distance so that only cleavable linkages in its immediate proximity are cleaved. Typically, such an agent must be activated by making a physical or chemical change to the reaction mixture so that the agent produces an short lived active species that diffuses to a cleavable linkage to effect cleavage. In a homogeneous format, the cleavage agent is preferably attached to a binding agent, such as an antibody, that targets the cleavage agent to a particular site prior to activation, e.g. on an analyte, in the proximity of the binding compound.

In a non-homogeneous, or heterogeneous format, stable complexes between binding compounds and analytes are separated from unbound binding compounds. Thus, a wider selection of cleavable linkages and cleavage agents are available for use with the invention. Cleavable linkages may not only include linkages that are labile to reaction with a locally acting reactive species, such as singlet oxygen, but also include linkages that are labile to agents that operate throughout a reaction mixture, such as a base cleaving all base-labile linkages, general illumination by light of an appropriate wavelength cleaving all photocleavable linkages, and so on. Additional linkages cleavable by agents that act generally throughout a reaction mixture include linkages cleavable by reduction, linkages cleaved by oxidation, acid-labile linkages, peptide linkages cleavable by specific proteases, and the like. References describing many such linkages include Greene and Wuts, Protective Groups in Organic Synthesis, Second Edition (John Wiley & Sons, New York, 1991); Hermanson, Bioconjugate Techniques (Academic Press, New York, 1996); and Still et al, U.S. Pat. No. 5,565,324.

An aspect of the invention includes providing mixtures of pluralities of different microparticles, wherein each different microparticle has one or more molecular tags attached through cleavable linkages. In another aspect, such microparticles have attached pairs of molecular tags and binding moieties. A binding moiety is a compound that is capable of forming a stable complex with an analyte under assay conditions. The nature of the binding moiety, cleavable linkage, and molecular tag may vary widely. A binding moiety may be an antibody binding composition, an antibody, a peptide, a peptide or non-peptide ligand for a cell surface receptor, an oligonucleotide, an oligonucleotide analog, such as a peptide nucleic acid, a lectin, or any other molecular entity that is capable of specific binding or complex formation with an analyte of interest and that can be attached to a microparticle. In one aspect, a molecular tag attached to a microparticle can be represented by the formula:

$$P\text{-}(L\text{-}E)_k$$

wherein P is a microparticle; L is a cleavable linkage; and E is a molecular tag. Preferably, in homogeneous assays for non-polynucleotide analytes, cleavable linkage, L, is an oxidation-labile linkage, and more preferably, it is a linkage that may be cleaved by singlet oxygen. The moiety "-(L-E)$_k$" indicates that a single microparticle has multiple molecular tags attached via cleavable linkages. In one aspect, k is an integer greater than several hundred, e.g. 100 to 500, or k is greater than several hundred to as many as several thousand, e.g. 500 to 5000. Within a composition of the invention, each of the plurality of different types of microparticle has a different molecular tag, E. Cleavable linkages, e.g. oxidation-labile linkages, and molecular tags, E, are attached to P by way of conventional chemistries.

When L is oxidation labile, L is preferably a thioether or its selenium analog; or an olefin, which contains carbon-carbon double bonds, wherein cleavage of a double bond to an oxo group, releases the molecular tag, E. Illustrative olefins include vinyl sulfides, vinyl ethers, enamines, imines substituted at the carbon atoms with an a-methine (CH, a carbon atom having at least one hydrogen atom), where the vinyl group may be in a ring, the heteroatom may be in a ring, or substituted on the cyclic olefinic carbon atom, and there will be at least one and up to four heteroatoms bonded to the olefinic carbon atoms. The resulting dioxetane may decompose spontaneously, by heating above ambient temperature, usually below about 75° C., by reaction with acid or base, or by photo-activation in the absence or presence of a photosensitizer. Such reactions are described in the following exemplary references: Adam and Liu, J. Amer. Chem. Soc. 94, 1206–1209, 1972, Ando, et al., J. C. S. Chem. Comm. 1972, 477–8, Ando, et al., Tetrahedron 29, 1507–13, 1973, Ando, et al., J. Amer. Chem. Soc. 96, 6766–8, 1974, Ando and Migita, ibid. 97, 5028–9, 1975, Wasserman and Terao, Tetra. Lett. 21, 1735–38, 1975, Ando and Watanabe, ibid. 47, 4127–30, 1975, Zaklika, et al., Photochemistry and Photobiology 30, 35–44, 1979, and Adam, et al., Tetra. Lett. 36, 7853–4, 1995. See also, U.S. Pat. No. 5,756,726.

The formation of dioxetanes is obtained by the reaction of singlet oxygen with an activated olefin substituted with an molecular tag at one carbon atom and the binding moiety at the other carbon atom of the olefin. See, for example, U.S. Pat. No. 5,807,675. These cleavable linkages may be depicted by the following formula:

$$-W-(X)_n C_\alpha = C_\beta (Y)(Z)-$$

wherein:

W may be a bond, a heteroatom, e.g., O, S, N, P, M (intending a metal that forms a stable covalent bond), or a functionality, such as carbonyl, imino, etc., and may be bonded to X or $C_\alpha$;

at least one X will be aliphatic, aromatic, alicyclic or heterocyclic and bonded to $C_\alpha$ through a hetero atom, e.g., N, O, or S and the other X may be the same or different and may in addition be hydrogen, aliphatic, aromatic, alicyclic or heterocyclic, usually being aromatic or aromatic heterocyclic wherein one X may be taken together with Y to form a ring, usually a heterocyclic ring, with the carbon atoms to which they are attached, generally when other than hydrogen being from about 1 to 20, usually 1 to 12, more usually 1 to 8 carbon atoms and one X will have 0 to 6, usually 0 to 4 heteroatoms, while the other X will have at least one heteroatom and up to 6 heteroatoms, usually 1 to 4 heteroatoms;

Y will come within the definition of X, usually being bonded to $C_\beta$ through a heteroatom and as indicated may be taken together with X to form a heterocyclic ring;

Z will usually be aromatic, including heterocyclic aromatic, of from about 4 to 12, usually 4 to 10 carbon atoms and 0 to 4 heteroatoms, as described above, being bonded directly to $C_\beta$ or through a heteroatom, as described above;

n is 1 or 2, depending upon whether the molecular tag is bonded to $C_\alpha$ or X;

wherein one of Y and Z will have a functionality for binding to the binding moiety, or be bound to the binding moiety, e.g. by serving as, or including a linkage group, to a binding moiety, T.

Preferably, W, X, Y, and Z are selected so that upon cleavage molecular tag, E, is within the size limits described below.

Illustrative cleavable linkages include S(molecular tag)-3-thiolacrylic acid, N(molecular tag), N-methyl 4-amino-4-butenoic acid, 3-hydroxyacrolein, N-(4-carboxyphenyl)-2-(molecular tag)-imidazole, oxazole, and thiazole.

Also of interest are N-alkyl acridinyl derivatives, substituted at the 9 position with a divalent group of the formula:

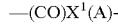

wherein:

$X^1$ is a heteroatom selected from the group consisting of O, S, N, and Se, usually one of the first three; and A is a chain of at least 2 carbon atoms and usually not more than 6 carbon atoms substituted with an molecular tag, where preferably the other valences of A are satisfied by hydrogen, although the chain may be substituted with other groups, such as alkyl, aryl, heterocyclic groups, etc., A generally being not more than 10 carbon atoms.

Also of interest are heterocyclic compounds, such as diheterocyclopentadienes, as exemplified by substituted imidazoles, thiazoles, oxazoles, etc., where the rings will usually be substituted with at least one aromatic group and in some instances hydrolysis will be necessary to release the molecular tag.

Also of interest are tellurium (Te) derivatives, where the Te is bonded to an ethylene group having a hydrogen atom β to the Te atom, wherein the ethylene group is part of an alicyclic or heterocyclic ring, that may have an oxo group, preferably fused to an aromatic ring and the other valence of the Te is bonded to the molecular tag. The rings may be coumarin, benzoxazine, tetralin, etc.

Figure 6:
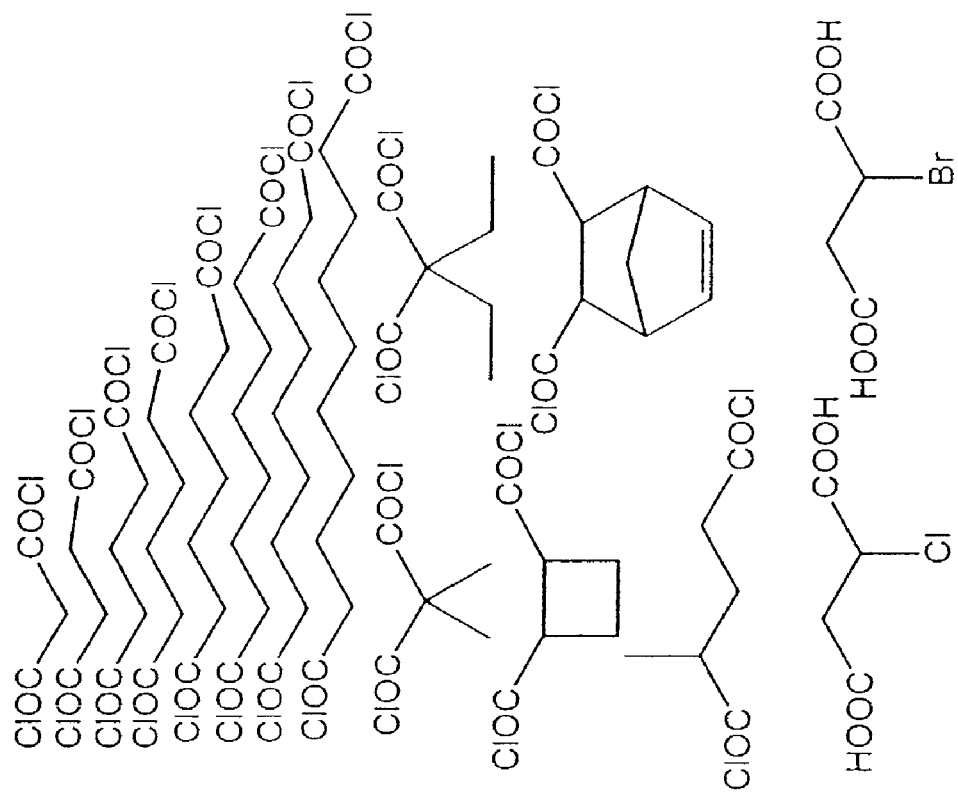
FIG. 6 illustrates several amino alcohols and diacid dichlorides that can be assembled into mobility modifiers in the synthesis of molecular tags.
Figure 6:
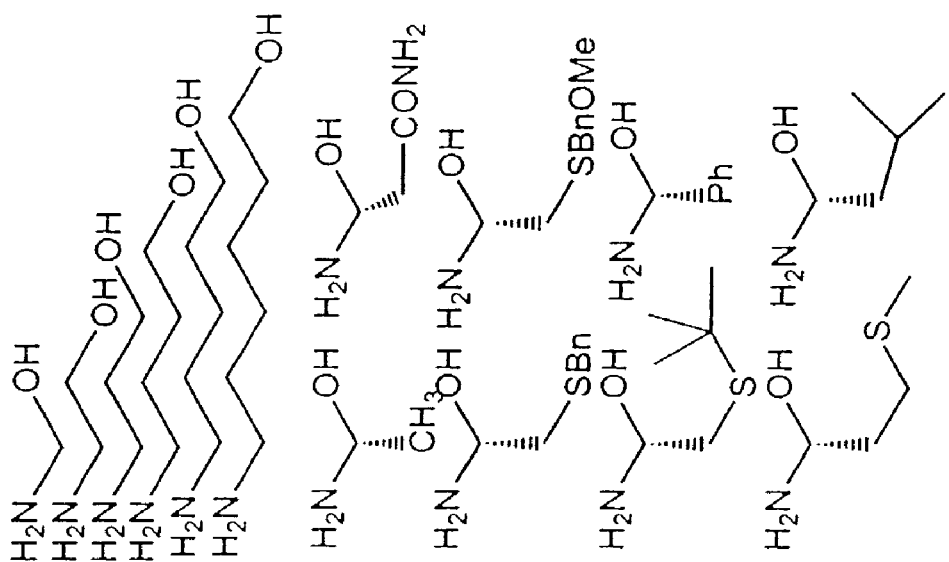

Several preferred cleavable linkages and their cleavage products are illustrated in FIGS. 6A–F. The thiazole cleavable linkage, "—$CH_2$-thiazole-$(CH2)_n$—C(=O)—NH-protein," shown in FIG. 6A, results in an molecular tag with the moiety "—$CH_2$—C(=O)—NH—CHO." Preferably, n is in the range of from 1 to 12, and more preferably, from 1 to 6. The oxazole cleavable linkage, "—$CH_2$-oxazole-$(CH2)_n$—C(=O)—NH-protein," shown in FIG. 6B, results in an molecular tag with the moiety "—$CH_2$—C(=O)O—CHO." An olefin cleavable linkage (FIG. 6C) is shown in connection with the binding compound embodiment "P-L-M-D," described above and with D being a fluorescein dye. The olefin cleavable linkage may be employed in other embodiments also. Cleavage of the illustrated olefin linkage results in an molecular tag of the form: "R—(C=O)-M-D," where "R" may be any substituent within the general description of the molecular tags, E, provided above. Preferably, R is an electron-donating group, e.g. Ullman et al, U.S. Pat. No. 6,251,581; Smith and March, March's Advanced Organic Chemistry: Reactions, Mechanisms, and Structure, $5^{th}$ Edition (Wiley-Interscience, New York, 2001); and the like. More preferably, R is an electron-donating group having from 1–8 carbon atoms and from 0 to 4 heteroatoms selected from the group consisting of 0, S, and N. In further preference, R is —$N(Q)_2$, —OQ, p-[$C_6H_4N(Q)_2$], furanyl, n-alkylpyrrolyl, 2-indolyl, or the like, where Q is alkyl or aryl. In further reference to the olefin cleavable linkage of FIG. 6C, substituents "X" and "R" are equivalent to substituents "X" and "Y" of the above formula describing cleavable linkage, L. In particular, X in FIG. 6C is preferably morpholino, —OR', or —SR", where R' and R" are aliphatic, aromatic, alicyclic or heterocyclic having from 1 to 8 carbon atoms and 0 to 4 heteroatoms selected from the group consisting of O, S. and N. A preferred thioether cleavable linkage is illustrated in FIG. 6D having the form "—$(CH_2)_2$—S—CH($C_6H_5$)C(=O)NH—$(CH_2)_n$—NH—," wherein n is in the range of from 2 to 12, and more preferably, in the range of from 2 to 6. Thioether cleavable linkages of the type shown in FIG. 6D may be attache to binding moieties, T, and molecular tags, E, by way of precursor compounds shown in FIGS. 6E and 6F. To attach to an amino group of a binding moiety, T, the terminal hydroxyl is converted to an NHS ester by conventional chemistry. After reaction with the amino group and attachment, the Fmoc protection group is removed to produce a free amine which is then reacted with an NHS ester of the molecular tag, such as compounds produced by the schemes of FIGS. 1, 2, and 4, with the exception that the last reaction step is the addition of an NHS ester, instead of a phosphoramidite group.

Molecular tag, E, is a water soluble organic compound that is stable with respect to the active species, especially singlet oxygen, and that includes a detection or reporter group. Otherwise, E may vary widely in size and structure. In one aspect, E has a molecular weight in the range of from about 100 to about 2500 daltons, more preferably, from about 100 to about 1500 daltons. Preferred structures of E are described more fully below. The detection group may generate an electrochemical, fluorescent, or chromogenic signal. Preferably, the detection group generates a fluorescent signal.

Molecular tags within a plurality of a composition each have either a unique chromatographic separation characteristics and/or a unique optical property with respect to the other members of the same plurality. In one aspect, the chromatographic separation characteristic is retention time in the column used for separation. In another aspect, the optical property is a fluorescence property, such as emission spectrum, fluorescence lifetime, fluorescence intensity at a given wavelength or band of wavelengths, or the like. Preferably, the fluorescence property is fluorescence intensity. For example, each molecular tag of a plurality may have the same fluorescent emission properties, but each will differ from one another by virtue of a unique retention time in the column of choice. On the other hand, or two or more of the molecular tags of a plurality may have identical retention times, but they will have unique fluorescent properties, e.g. spectrally resolvable emission spectra, so that all the members of the plurality are distinguishable by the combination of molecular separation and fluorescence measurement.

In one aspect, molecular tag, E, is (M, D), where M is a mobility-modifying moiety and D is a detection moiety. The notation "(M, D)" is used to indicate that the ordering of the M and D moieties may be such that either moiety can be adjacent to the cleavable linkage, L. That is, "P-L-(M, D)" designates binding compound of either of two forms: "P-L-M-D" or "P-L-D-M."

Detection moiety, D, may be a fluorescent label or dye, a chromogenic label or dye, an electrochemical label, or the like. Preferably, D is a fluorescent dye. Exemplary fluorescent dyes for use with the invention include water-soluble rhodamine dyes, fluoresceins, 4,7-dichlorofluoresceins, benzoxanthene dyes, and energy transfer dyes, disclosed in the following references: Handbook of Molecular Probes and Research Reagents, 8th ed., (Molecular Probes, Eugene, 2002); Lee et al, U.S. Pat. No. 6,191,278; Lee et al, U.S. Pat. No. 6,372,907; Menchen et al, U.S. Pat. No. 6,096,723; Lee et al, U.S. Pat. No. 5,945,526; Lee et al, Nucleic Acids Research, 25: 2816–2822 (1997); Hobb, Jr., U.S. Pat. No. 4,997,928; Khanna et al., U.S. Pat. No. 4,318,846; Reynolds, U.S. Pat. No. 3,932,415; Eckert et al, U.S. Pat. No. 2,153,059; Eckert et al, U.S. Pat. No. 2,242,572; Taing et al, International patent publication WO 02/30944; and the like. Further specific exemplary fluorescent dyes include 5- and 6-carboxyrhodamine 6G; 5- and 6-carboxy-X-rhodamine, 5- and 6-carboxytetramethylrhodamine, 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7',8'-dibenzo-4',5'-dichloro-5- and 6carboxy-4,7-dichlorofluorescein, 2',7'-dichloro-5- and 6-carboxy-4,7-dichlorofluorescein, and 2',4',5',7'-tetrachloro-5- and 6-carboxy-4,7-dichlorofluorescein. Most preferably, D is a fluorescein or a fluorescein derivative.

The size and composition of mobility-modifying moiety, M, can vary from a bond to about 100 atoms in a chain, usually not more than about 60 atoms, more usually not more than about 30 atoms, where the atoms are carbon, oxygen, nitrogen, phosphorous, boron and sulfur. Generally, when other than a bond, the mobility-modifying moiety has from about 0 to about 40, more usually from about 0 to about 30 heteroatoms, which in addition to the heteroatoms indicated above may include halogen or other heteroatom. The total number of atoms other than hydrogen is generally fewer than about 200 atoms, usually fewer than about 100 atoms. Where acid groups are present, depending upon the pH of the medium in which the mobility-modifying moiety is present, various cations may be associated with the acid group. The acids may be organic or inorganic, including carboxyl, thionocarboxyl, thiocarboxyl, hydroxamic, phosphate, phosphite, phosphonate, phosphinate, sulfonate, sulfinate, boronic, nitric, nitrous, etc. For positive charges, substituents include amino (includes ammonium), phosphonium, sulfonium, oxonium, etc., where substituents are generally aliphatic of from about 1–6 carbon atoms, the total number of carbon atoms per heteroatom, usually be less than about 12, usually less than about 9. The side chains include amines, ammonium salts, hydroxyl groups, including phenolic groups, carboxyl groups, esters, amides, phosphates, heterocycles. M may be a homo-oligomer or a hetero-oligomer, having different monomers of the same or different chemical characteristics, e.g., nucleotides and amino acids.

In another aspect, (M,D) moieties are constructed from chemical scaffolds used in the generation of combinatorial libraries. For example, the following references describe scaffold compound useful in generating diverse mobility modifying moieties: peptoids (PCT Publication No WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. U.S.A. 90: 6909–6913 (1993), vinylogous polypeptides (Hagihara et al. J. Amer. Chem. Soc. 114: 6568 (1992)), nonpeptidal peptidomimetics with a Beta-D-Glucose scaffolding (Hirschmann, R. et al., J. Amer. Chem. Soc. 114: 9217–9218 (1992)), analogous organic syntheses of small compound libraries (Chen, C. et al. J. Amer. Chem. Soc. 116: 2661(1994)), oligocarbamates (Cho, C. Y. et al. Science 261: 1303(1993)), peptidyl phosphonates (Campbell, D. A. et al., J. Org. Chem. 59:658(1994)); Cheng et al., U.S. Pat. No. 6,245,937; Heizmann et al, "Xanthines as a scaffold for molecular diversity," Mol. Divers. 2: 171–174 (1997); Pavia et al, Bioorg. Med. Chem., 4: 659–666 (1996); Ostresh et al, U.S. Pat. No. 5,856,107; Gordon, E. M. et al., J. Med. Chem. 37: 1385 (1994); and the like. Preferably, in this aspect, D is a substituent on a scaffold and M is the rest of the scaffold.

In yet another aspect, (M, D) moieties are constructed from one or more of the same or different common or commercially available linking, cross-linking, and labeling reagents that permit facile assembly, especially using a commercial DNA or peptide synthesizer for all or part of the synthesis. In this aspect, (M, D) moieties are made up of subunits usually connected by phosphodiester and amide bonds. Exemplary, precursors include, but are not limited to, dimethoxytrityl (DMT)-protected hexaethylene glycol phosphoramidite, 6-(4-Monomethoxytritylamino)hexyl-(2-cyanoethyl)-(N,N-diisopropyl)-phosphoramidite, 12-(4-Monomethoxytritylamino)dodecyl-(2-cyanoethyl)-(N,N-diisopropyl)-phosphoramidite, 2-[2-(4-Monomethoxytrityl) aminoethoxy]ethyl-(2-cyanoethyl), N,N-diisopropyl)-phosphoramidite, (S-Trityl-6-mercaptohexyl)-(2-cyanoethyl)-(N,N-diisopropyl)-phosphoramidite, 5'-Fluorescein phosphoramidite, 5'-Hexachloro-Fluorescein Phosphoramidite, 5'-Tetrachloro-Fluorescein Phosphoramidite, 9-O-Dimethoxytrityl-triethylene glycol,1-[(2-cyanoethyl)-(N,N-diisopropyl)]-phosphoramidite, 3(4,4'Dimethoxytrityloxy)propyl-1-[(2-cyanoethyl)-(N,N-diisopropyl)]-phosphoramidite, 5'-O-Dimethoxytrityl-1',2'-Dideoxyribose-3'-[(2-cyanoethyl)-(N,N-diisopropyl)]-phosphoramidite, 18-O Dimethoxytritylhexaethyleneglycol, 1-[(2-cyanoethyl)-(N,N-diisopropyl)]-phosphoramidite, 12-(4,4'-Dimethoxytrityloxy)dodecyl-1-[(2-cyanoethyl)-(N,N-diisopropyl)]-phosphoramidite, 1,3-bis-[5-(4,4'dimethoxytrityloxy)pentylamido]propyl-2-[(2-cyanoethyl)-(N,N-diisopropyl)]phosphoramidite, 1-[5-(4,4'-dimethoxytrityloxy)pentylamido]-3-[5-fluorenomethoxycarbonyloxy pentylamido]-propyl-2-[(2-cyanoethyl)-(N,N-diisopropyl)]-phosphoramidite, Tris-2,2, 2-[3-(4,4'-dimethoxytrityloxy)propyloxymethyl]ethyl-[(2-cyanoethyl)-(N,N-diisopropyl)]-phosphoramidite, succinimidyl trans-4-(maleimidylmethyl) cyclohexane-1-carboxylate (SMCC), succinimidyl 3-(2-pyridyldithio)propionate (SPDP), succinimidyl acetylthioacetate, Texas Red-X-succinimidyl ester, 5- and 6-carboxytetramethylrhodamine succinimidyl ester, bis-(4-carboxypiperidinyl)sulfonerhodamine di(succinimidyl ester), 5- and 6-((N-(5-aminopentyl)aminocarbonyl)tetramethylrhodamine, succinimidyl 4-(p-maleimidophenyl)butyrate (SMPB); N-γ-maleimidobutyryl-oxysuccinimide ester (GMBS); p-nitrophenyl iodoacetate (NPIA); 4-(4-N-maleimidophenyl)butyric acid hydrazide (MPBH); and like reagents. The above reagents are commercially available, e.g. from Glen Research (Sterling, Va.), Molecular Probes (Eugene, Oreg.), Pierce Chemical, and like reagent providers. Use of the above reagents in conventional synthetic schemes is well known in the art, e.g. Hermanson, Bioconjugate Techniques (Academic Press, New York, 1996). In particular, M may be constructed from the following reagents: dimethoxytrityl (DMT)-protected hexaethylene glycol phosphoramidite, 6-(4-Monomethoxytritylamino) hexyl-(2-cyanoethyl)-(N,N-diisopropyl)-phosphoramidite, 12-(4-Monomethoxytritylamino)dodecyl-(2-cyanoethyl)-(N,N-diisopropyl)-phosphoramidite, 2-[2-(4-Monomethoxytrityl)aminoethoxy]ethyl-(2-cyanoethyl), N,N-diisopropyl)-phosphoramidite, (S-Trityl-6-mercaptohexyl)-(2-cyanoethyl)-(N,N-diisopropyl)-phosphoramidite, 9-O-Dimethoxytrityl-triethylene glycol, 1-[(2-cyanoethyl)-(N,N-diisopropyl)]-phosphoramidite, 3(4,4'Dimethoxytrityloxy) propyl-1-[(2-cyanoethyl)-(N,N-diisopropyl)]-phosphoramidite, 5'-O-Dimethoxytrityl-1',2'-Dideoxyribose-3'-[(2-cyanoethyl)-(N,N-diisopropyl)]-phosphoramidite, 18-O Dimethoxytritylhexaethyleneglycol, 1-[(2-cyanoethyl)-(N,N-diisopropyl)]-phosphoramidite, 12-(4,4'-Dimethoxytrityloxy)dodecyl-1-[(2-cyanoethyl)-(N,N-diisopropyl)]-phosphoramidite, 1,3-bis-[5-(4,4'-dimethoxytrityloxy)pentylamido]propyl-2-[(2-cyanoethyl)-(N,N-diisopropyl)]-phosphoramidite, 1-[5-(4,4'-dimethoxytrityloxy)pentylamido]-3-[5-fluorenomethoxycarbonyloxy pentylamido]-propyl-2-[(2-cyanoethyl)-(N,N-diisopropyl)]-phosphoramidite, Tris-2,2, 2-[3-(4,4'-dimethoxytrityloxy)propyloxymethyl]ethyl-[(2-cyanoethyl)-(N,N-diisopropyl)]-phosphoramidite, succinimidyl trans-4-(maleimidylmethyl) cyclohexane-1-carboxylate (SMCC), succinimidyl 3-(2-pyridyldithio)propionate (SPDP), succinimidyl acetylthioacetate, succinimidyl 4-(p-maleimidophenyl)butyrate (SMPB); N-γ-maleimidobutyryl-oxysuccinimide ester (GMBS); p-nitrophenyl iodoacetate (NPIA); and 4-(4-N-maleimidophenyl)butyric acid hydrazide (MPBH).

M may also comprise polymer chains prepared by known polymer subunit synthesis methods. Methods of forming selected-length polyethylene oxide-containing chains are well known, e.g. Grossman et al, U.S. Pat. No. 5,777,096. It can be appreciated that these methods, which involve coupling of defined-size, multi-subunit polymer units to one another, directly or via linking groups, are applicable to a wide variety of polymers, such as polyethers (e.g., polyethylene oxide and polypropylene oxide), polyesters (e.g., polyglycolic acid, polylactic acid), polypeptides, oligosaccharides, polyurethanes, polyamides, polysulfonamides, polysulfoxides, polyphosphonates, and block copolymers thereof, including polymers composed of units of multiple subunits linked by charged or uncharged linking groups. In addition to homopolymers, the polymer chains used in accordance with the invention include selected-length copolymers, e.g., copolymers of polyethylene oxide units alternating with polypropylene units. As another example, polypeptides of selected lengths and amino acid composition (i.e., containing naturally occurring or man-made amino acid residues), as homopolymers or mixed polymers.

In another aspect, after release, molecular tag, E, is defined by the formula:

A-M-D wherein:

A is —C(=O)R, where R is aliphatic, aromatic, alicyclic or heterocyclic having from 1 to 8 carbon atoms and 0 to 4 heteroatoms selected from the group consisting of O, S. and N; —CH$_2$—C(=O)—NH—CHO; —SO$_2$H; —CH$_2$—C(=O)O—CHO; —C(=O)NH—(CH$_2$)$_n$—NH—C(=O)C(=O)—(C$_6$H$_5$), where n is in the range of from 2 to 12;

D is a fluorescent dye; and

M is as described above, with the proviso that the total molecular weight of A-M-D be within the range of from about 100 to about 2500 daltons.

In another aspect, D is a fluorescein and the total molecular weight of A-M-D is in the range of from about 100 to about 1500 daltons.

In another aspect, M may be synthesized from smaller molecules that have functional groups that provide for linking of the molecules to one another, usually in a linear chain. Such functional groups include carboxylic acids, amines, and hydroxy- or thiol- groups. In accordance with the present invention the charge-imparting moiety may have one or more side groups pending from the core chain. The side groups have a functionality to provide for linking to a label or to another molecule of the charge-imparting moiety. Common functionalities resulting from the reaction of the functional groups employed are exemplified by forming a covalent bond between the molecules to be conjugated. Such functionalities are disulfide, amide, thioamide, dithiol, ether, urea, thiourea, guanidine, azo, thioether, carboxylate and esters and amides containing sulfur and phosphorus such as, e.g., sulfonate, phosphate esters, sulfonamides, thioesters, etc., and the like.

Cleavage-Inducing Moieties Producing Active Species

A cleavage-inducing moiety is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background because beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide, and the like. Illustrative quenchers for active species that cause oxidation include polyenes, carotenoids, vitamin E, vitamin C, amino acid-pyrrole N-conjugates of tyrosine, histidine, and glutathione, and the like, e.g. Beutner et al, Meth. Enzymol., 319: 226–241(2000).

An important consideration for the cleavage-inducing moiety and the cleavable linkage is that they not be so far removed from one another when bound to a target protein that the active species generated by the sensitizer diffuses and loses its activity before it can interact with the cleavable linkage. Accordingly, a cleavable linkage preferably are within 1000 nm, preferably 20–100 nm of a bound cleavage-inducing moiety. This effective range of a cleavage-inducing moiety is referred to herein as its "effective proximity." Generators of active species include enzymes, such as oxidases, such as glucose oxidase, xanthene oxidase, D-amino acid oxidase, NADH-FMN oxidoreductase, galactose oxidase, glyceryl phosphate oxidase, sarcosine oxidase, choline oxidase and alcohol oxidase, that produce hydrogen peroxide, horse radish peroxidase, that produces hydroxyl radical, various dehydrogenases that produce NADH or NADPH, urease that produces ammonia to create a high local pH.

A sensitizer is a compound that can be induced to generate a reactive intermediate, or species, usually singlet oxygen. Preferably, a sensitizer used in accordance with the invention is a photosensitizer. Other sensitizers included within the scope of the invention are compounds that on excitation by heat, light, ionizing radiation, or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed in the following references: Di Mascio et al, FEBS Lett., 355: 287 (1994)(peroxidases and oxygenases); Kanofsky, J. Biol. Chem. 258: 5991–5993 (1983)(lactoperoxidase); Pierlot et al, Meth. Enzymol., 319: 3–20 (2000)(thermal lysis of endoperoxides); and the like.

Attachment of a binding agent to the cleavage-inducing moiety may be direct or indirect, covalent or non-covalent and can be accomplished by well-known techniques, commonly available in the literature. See, for example, "Immobilized Enzymes," Ichiro Chibata, Halsted Press, New York (1978); Cuatrecasas, J. Biol. Chem., 245:3059 (1970). A wide variety of functional groups are available or can be incorporated. Functional groups include carboxylic acids, aldehydes, amino groups, cyano groups, ethylene groups, hydroxyl groups, mercapto groups, and the like. The manner of linking a wide variety of compounds is well known and is amply illustrated in the literature (see above). The length of a linking group to a binding agent may vary widely, depending upon the nature of the compound being linked, the effect of the distance on the specific binding properties and the like.

It may be desirable to have multiple cleavage-inducing moieties attached to a binding agent to increase, for example, the number of active species generated. This can be accomplished with a polyfunctional material, normally polymeric, having a plurality of functional groups, e.g., hydroxy, amino, mercapto, carboxy, ethylenic, aldehyde, etc., as sites for linking. Alternatively a support may be used. The support can have any of a number of shapes, such as particle including bead, film, membrane, tube, well, strip, rod, and the like. For supports in which photosensitizer is incorporated, the surface of the support is, preferably, hydrophilic or capable of being rendered hydrophilic and the body of the support is, preferably, hydrophobic. The support may be suspendable in the medium in which it is employed. Examples of suspendable supports, by way of illustration and not limitation, are polymeric materials such as latex, lipid bilayers, oil droplets, cells and hydrogels. Other support compositions include glass, metals, polymers, such as nitrocellulose, cellulose acetate, poly(vinyl chloride), polyacrylamide, polyacrylate, polyethylene, polypropylene, poly (4-methylbutene), polystyrene, polymethacrylate, poly(ethylene terephthalate), nylon, poly(vinyl butyrate), etc.; either used by themselves or in conjunction with other materials. Attachment of binding agents to the support may be direct or indirect, covalent or non-covalent and can be accomplished by well-known techniques, commonly available in the literature as discussed above. See, for example, "Immobilized Enzymes," Ichiro Chibata, supra. The surface of the support will usually be polyfunctional or be capable of being polyfunctionalized or be capable of binding to a target-binding moiety, or the like, through covalent or specific or non-specific non-covalent interactions.

The cleavage-inducing moiety may be associated with the support by being covalently or non-covalently attached to the surface of the support or incorporated into the body of the support. Linking to the surface may be accomplished as discussed above. The cleavage-inducing moiety may be incorporated into the body of the support either during or after the preparation of the support. In general, the cleavage-inducing moiety is associated with the support in an amount necessary to achieve the necessary amount of active species. Generally, the amount of cleavage-inducing moiety is determined empirically.

Photosensitizers as Cleavage-Inducing Moieties

As mentioned above, the preferred cleavage-inducing moiety in accordance with the present invention is a photosensitizer that produces singlet oxygen. As used herein, "photosensitizer" refers to a light-adsorbing molecule that when activated by light converts molecular oxygen into singlet oxygen. Photosensitizers may be attached directly or indirectly, via covalent or non-covalent linkages, to the binding agent of a class-specific reagent. Guidance for constructing of such compositions, particularly for antibodies as binding agents, available in the literature, e.g. in the fields of photodynamic therapy, immunodiagnostics, and the like. The following are exemplary references: Ullman, et al., Proc. Natl. Acad. Sci. USA 91, 5426–5430 (1994); Strong et al, Ann. New York Acad. Sci., 745: 297–320 (1994); Yarmush et al, Crit. Rev. Therapeutic Drug Carrier Syst., 10: 197–252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516,636; and the like.

Likewise, there is guidance in the literature regarding the properties and selection of photosensitizers suitable for use in the present invention. The following are exemplary references: Wasserman and R. W. Murray. Singlet Oxygen. (Academic Press, New York, 1979); Baumstark, Singlet Oxygen, Vol. 2 (CRC Press Inc., Boca Raton, Fla. 1983); and Turro, Modern Molecular Photochemistry (University Science Books, 1991).

The photosensitizers are sensitizers for generation of singlet oxygen by excitation with light. The photosensitizers include dyes and aromatic compounds, and are usually compounds comprised of covalently bonded atoms, usually with multiple conjugated double or triple bonds. The compounds typically absorb light in the wavelength range of about 200 to about 1,100 nm, usually, about 300 to about 1,000 nm, preferably, about 450 to about 950 nm, with an extinction coefficient at its absorbance maximum greater than about 500 $M^{-1}$ $cm^{-1}$, preferably, about 5,000 $M^{-1}$ $cm^{-1}$, more preferably, about 50,000 $M^{-1}$ $cm^{-1}$, at the excitation wavelength. The lifetime of an excited state produced following absorption of light in the absence of oxygen will usually be at least about 100 nanoseconds, preferably, at least about 1 millisecond. In general, the lifetime must be sufficiently long to permit cleavage of a linkage in a reagent in accordance with the present invention. Such a reagent is normally present at concentrations as discussed below. The photosensitizer excited state usually has a different spin quantum number (S) than its ground state and is usually a triplet (S=1) when the ground state, as is usually the case, is a singlet (S=0). Preferably, the photosensitizer has a high intersystem crossing yield. That is, photoexcitation of a photosensitizer usually produces a triplet state with an efficiency of at least about 10%, desirably at least about 40%, preferably greater than about 80%.

Photosensitizers chosen are relatively photostable and, preferably, do not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates inter-system crossing such as a carbonyl or imine group or a heavy atom selected from rows 3–6 of the periodic table, especially iodine or bromine, or they may have extended aromatic structures.

A large variety of light sources are available to photo-activate photosensitizers to generate singlet oxygen. Both polychromatic and monchromatic sources may be used as long as the source is sufficiently intense to produce enough singlet oxygen in a practical time duration. The length of the irradiation is dependent on the nature of the photosensitizer, the nature of the cleavable linkage, the power of the source of irradiation, and its distance from the sample, and so forth. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include, by way of illustration and not limitation, lasers such as, e.g., helium-neon lasers, argon lasers, YAG lasers, He/Cd lasers, and ruby lasers; photodiodes; mercury, sodium and xenon vapor lamps; incandescent lamps such as, e.g., tungsten and tungsten/halogen; flashlamps; and the like.

Examples of photosensitizers that may be utilized in the present invention are those that have the above properties and are enumerated in the following references: Turro, Modern Molecular Photochemistry (cited above); Singh and Ullman, U.S. Pat. No. 5,536,834; Li et al, U.S. Pat. No. 5,763,602; Ullman, et al., Proc. Natl. Acad. Sci. USA 91, 5426–5430 (1994); Strong et al, Ann. New York Acad. Sci., 745: 297–320 (1994); Martin et al, Methods Enzymol., 186: 635–645 (1990);Yarmush et al, Crit. Rev. Therapeutic Drug Carrier Syst., 10: 197–252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516, 636; Wohrle, Chimia, 45: 307–310 (1991); Thetford, European patent publ. 0484027; Sessler et al, SPIE, 1426: 318–329 (1991); Madison et al, Brain Research, 522: 90–98 (1990); Polo et al, Inorganica Chimica Acta, 192: 1–3 (1992); Demas et al, J. Macromol. Sci., A25: 1189–1214 (1988); and the like. Exemplary photosensitizers are listed in Table 1b.

TABLE 1b

Exemplary Photosensitizers

| | |
|---|---|
| Hypocrellin A | Tetraphenylporphyrin |
| Hypocrellin B | Halogenated derivatives of rhodamine dyes |
| Hypericin | metallo-Porphyrins |
| Halogenated derivatives of fluorescein dyes | Phthalocyanines |
| Rose bengal | Naphthalocyanines |
| Merocyanine 540 | Texaphyrin-type macrocycles |
| Methylene blue | Hematophorphyrin |
| 9-Thioxanthone | 9,10-Dibromoanthracene |
| Chlorophylls | Benzophenone |
| Phenaleone | Chlorin e6 |
| Protoporphyrin | Perylene |
| Benzoporphyrin A monacid | Benzoporphryin B monacid |

In certain embodiments the photosensitizer moiety comprises a support, as discussed above with respect to the cleavage-inducing moiety. The photosensitizer may be associated with the support by being covalently or non-covalently attached to the surface of the support or incorporated into the body of the support as discussed above. In general, the photosensitizer is associated with the support in an amount necessary to achieve the necessary amount of singlet oxygen. Generally, the amount of photosensitizer is determined empirically. Photosensitizers used as the photosensitizer are preferably relatively non-polar to assure dissolution into a lipophilic member when the photosensitizer is incorporated in, for example, a latex particle to form photosensitizer beads, e.g. as disclosed by Pease et al., U.S. Pat. No. 5,709,994. For example, the photosensitizer rose bengal is covalently attached to 0.5 micron latex beads by means of chloromethyl groups on the latex to provide an ester linking group, as described in J. Amer. Chem. Soc., 97: 3741 (1975).

In one aspect of the invention, a class-specific reagent comprises a first binding agent that is an antibody and a cleavage-inducing moiety that is a photosensitizer, such that the photosensitizer is covalently linked to the antibody, e.g. using well know techniques as disclosed in Strong et al (cited above); Yarmush et al (cited above); or the like. Alternatively, a class-specific reagent comprises a solid phase support, e.g. a bead, to which a photosensitizer is covalently or non-covalently attached and an antibody is attached, preferably convalently, either directly or by way of a functionalized polymer, such as amino-dextran, or the like.

Conjugation of sensitizer molecules to assay reagents: Sensitizer molecules can be conjugated to an antibody, antigen, avidin, biotin, mononucleotides, polynucleotides, small molecules, large molecules and others by various methods and configurations. For example, an activated (NHS ester, aldehyde, sulfonyl chloride, etc) sensitizer (Rose Bengal, phthalocyanine, etc.) can be reacted with reactive amino-group containing moieties (antibody, avidin or other proteins, H2N-LC-Biotin, aminodextran, amino-group containing other small and large molecules). The formed conjugates can be used directly (for example the antibody-sensitizer conjugate, Biotin-LC-sensitizer, etc.) in various assays. Also, the formed conjugates can be further coupled with antibody (for example, aminodextran-sensitizer conjugate containing 20–200 sensitizers and 200–500 amino-groups can be coupled to periodate oxidized antibody molecules to generate the antibody-dextran-sensitizer conjugate) or with the antibody and a particle. For example, aminodextran-sensitizer conjugate containing 20–200 sensitizers and 200–500 amino-groups can be coupled to carboxylated polystyrene beads by EDC coupling chemistry to form the sensitizer-aminodextran-particle conjugate. Methods for incorporation of a sensitizer into a particle are given in, e.g., U.S. Pat. No. 5,340,716. Then the Na-periodate oxidized antibody molecules can be reacted with the amino-groups of the aminodextran molecule, in presence of sodium cyanoborohydride, to generate the antibody-dextran-sensitizer-particle conjugate). It should be noted that instead of an antibody molecule, avidin or other molecules can be used.

Separation of Released Molecular Tags

As mentioned above, molecular tags are designed for separation by a separation technique that can distinguish molecular tags based on one or more physical, chemical, and/or optical characteristics. Preferably, such separation technique is capable of providing quantitative information as well as qualitative information about the presence or absence of molecular tags (and therefore, corresponding analytes). In one aspect, a liquid phase separation technique is employed so that a solution, e.g. buffer solution, reaction solvent, or the like, containing a mixture of molecular tags is processed to bring about separation of individual kinds of molecular tags. Usually, such separation is accompanied by the differential movement of molecular tags from such a starting mixture along a path until discernable peaks or bands form that correspond to regions of increased concentration of the respective molecular tags. Such a path may be defined by a fluid flow, electric field, magnetic field, or the like. The selection of a particular separation technique depends on several factors including the expense and convenience of using the technique, the resolving power of the technique given the chemical nature of the molecular tags, the number of molecular tags to be separated, the type of detection mode employed, and the like. Preferably, molecular tags are electrophoretically or chromatographically separated.

A. Electrophoretic Separation

Methods for electrophoresis of are well known and there is abundant guidance for one of ordinary skill in the art to make design choices for forming and separating particular pluralities of molecular tags. The following are exemplary references on electrophoresis: Krylov et al, Anal. Chem., 72: 111R–128R (2000); P. D. Grossman and J. C. Colburn, Capillary Electrophoresis: Theory and Practice, Academic Press, Inc., NY (1992); U.S. Pat. Nos. 5,374,527; 5,624,800; 5,552,028; ABI PRISM 377 DNA Sequencer User's Manual, Rev. A, January 1995, Chapter 2 (Applied Biosystems, Foster City, Calif.); and the like. In one aspect, molecular tags are separated by capillary electrophoresis. Design choices within the purview of those of ordinary skill include but are not limited to selection of instrumentation from several commercially available models, selection of operating conditions including separation media type and concentration, pH, desired separation time, temperature, voltage, capillary type and dimensions, detection mode, the number of molecular tags to be separated, and the like.

In one aspect of the invention, during or after electrophoretic separation, the molecular tags are detected or identified by recording fluorescence signals and migration times (or migration distances) of the separated compounds, or by constructing a chart of relative fluorescent and order of migration of the molecular tags (e.g., as an electropherogram). To perform such detection, the molecular tags can be illuminated by standard means, e.g. a high intensity mercury vapor lamp, a laser, or the like. Typically, the molecular tags are illuminated by laser light generated by a He—Ne gas laser or a solid-state diode laser. The fluorescence signals can then be detected by a light-sensitive detector, e.g., a photomultiplier tube, a charged-coupled device, or the like. Exemplary electrophoresis detection systems are described elsewhere, e.g., U.S. Pat. Nos. 5,543,026; 5,274,240; 4,879,012; 5,091,652; 6,142,162; or the like. In another aspect, molecular tags may be detected electrochemically detected, e.g. as described in U.S. Pat. No. 6,045,676.

Electrophoretic separation involves the migration and separation of molecules in an electric field based on differences in mobility. Various forms of electrophoretic separation include, by way of example and not limitation, free zone electrophoresis, gel electrophoresis, isoelectric focusing, isotachophoresis, capillary electrochromatography, and micellar electrokinetic chromatography. Capillary electrophoresis involves electroseparation, preferably by electrokinetic flow, including electrophoretic, dielectrophoretic and/or electroosmotic flow, conducted in a tube or channel of from about 1 to about 200 micrometers, usually, from about 10 to about 100 micrometers cross-sectional dimensions. The capillary may be a long independent capillary tube or a channel in a wafer or film comprised of silicon, quartz, glass or plastic.

In capillary electroseparation, an aliquot of the reaction mixture containing the molecular tags is subjected to electroseparation by introducing the aliquot into an electroseparation channel that may be part of, or linked to, a capillary device in which the amplification and other reactions are performed. An electric potential is then applied to the electrically conductive medium contained within the channel to effectuate migration of the components within the combination. Generally, the electric potential applied is sufficient to achieve electroseparation of the desired components according to practices well known in the art. One skilled in the art will be capable of determining the suitable electric potentials for a given set of reagents used in the present invention and/or the nature of the cleaved labels, the nature of the reaction medium and so forth. The parameters for the electroseparation including those for the medium and the electric potential are usually optimized to achieve maximum separation of the desired components. This may be achieved empirically and is well within the purview of the skilled artisan.

Detection may be by any of the known methods associated with the analysis of capillary electrophoresis columns including the methods shown in U.S. Pat. No.: 5,560,811 (column 11, lines 19–30), U.S. Pat. Nos. 4,675,300, 4,274,240 and 5,324,401, the relevant disclosures of which are incorporated herein by reference. Those skilled in the electrophoresis arts will recognize a wide range of electric potentials or field strengths may be used, for example, fields of 10 to 1000 V/cm are used with about 200 to about 600 V/cm being more typical. The upper voltage limit for commercial systems is about 30 kV, with a capillary length of about 40 to about 60 cm, giving a maximum field of about 600 V/cm. For DNA, typically the capillary is coated to reduce electroosmotic flow, and the injection end of the capillary is maintained at a negative potential.

For ease of detection, the entire apparatus may be fabricated from a plastic material that is optically transparent, which generally allows light of wavelengths ranging from about 180 to about 1500 nm, usually about 220 to about 800 nm, more usually about 450 to about 700 nm, to have low transmission losses. Suitable materials include fused silica, plastics, quartz, glass, and so forth.

B. Chromatographic Separation

In one aspect of the invention, pluralities of molecular tags are designed for separation by chromatography based on one or more physical characteristics that include but are not limited to molecular weight, shape, solubility, pKa, hydrophobicity, charge, polarity, or the like. A chromatographic separation technique is selected based on parameters such as column type, solid phase, mobile phase, and the like, followed by selection of a plurality of molecular tags that may be separated to form distinct peaks or bands in a single operation. Several factors determine which HPLC technique is selected for use in the invention, including the number of molecular tags to be detected (i.e. the size of the plurality), the estimated quantities of each molecular tag that will be generated in the assays, the availability and ease of synthesizing molecular tags that are candidates for a set to be used in multiplexed assays, the detection modality employed, and the availability, robustness, cost, and ease of operation of HPLC instrumentation, columns, and solvents. Generally, columns and techniques are favored that are suitable for analyzing limited amounts of sample and that provide the highest resolution separations. Guidance for making such selections can be found in the literature, e.g. Snyder et al, Practical HPLC Method Development, (John Wiley & Sons, New York, 1988); Millner, "High Resolution Chromatography: A Practical Approach", Oxford University Press, New York (1999), Chi-San Wu, "Column Handbook for Size Exclusion Chromatography", Academic Press, San Diego (1999), and Oliver, "HPLC of Macromolecules: A Practical Approach, Oxford University Press", Oxford, England (1989). In particular, procedures are available for systematic development and optimization of chromatographic separations given conditions, such as column type, solid phase, and the like, e.g. Haber et al, J. Chromatogr. Sci., 38: 386–392 (2000); Outinen et al, Eur. J. Pharm. Sci., 6: 197–205 (1998); Lewis et al, J. Chromatogr., 592: 183–195 and 197–208 (1992); and the like.

In one aspect, initial selections of molecular tag candidates are governed by the physiochemical properties of molecules typically separated by the selected column and stationary phase. The initial selections are then improved empirically by following conventional optimization procedure, as described in the above reference, and by substituting more suitable candidate molecular tags for the separation objectives of a particular embodiment. In one aspect, separation objectives of the invention include (i) separation of the molecular tags of a plurality into distinguishable peaks or bands in a separation time of less than 60 minutes, and more preferably in less than 40 minutes, and still more preferably in a range of between 10 to 40 minutes, (ii) the formation of peaks or bands such that any pair has a resolution of at least 1.0, more preferably at least 1.25, and still more preferably, at least 1.50, (iii) column pressure during separation of less than 150 bar, (iv) separation temperature in the range of from 25° C. to 90° C., preferably in the range of from 35° C. to 80° C., and (v) the plurality of distinguishable peaks is in the range of from 5 to 30 and all of the peaks in the same chromatogram. As used herein, "resolution" in reference to two peaks or bands is the distance between the two peak or band centers divided by the average base width of the peaks, e.g. Snyder et al (cited above).

A chromatographic method is used to separate molecular tags based on their chromatographic properties. A chromatographic property can be, for example, a retention time of a molecular tag on a specific chromatographic medium under defined conditions, or a specific condition under which a molecular tag is eluted from a specific chromatographic medium. A chromatographic property of a molecular tag can also be an order of elution, or pattern of elution, of a molecular tag contained in a group or set of molecular tags being chromatographically separated using a specific chromatographic medium under defined conditions. A chromatographic property of a molecular tag is determined by the physical properties of the molecular tag and its interactions with a chromatographic medium and mobile phase. Defined conditions for chromatography include particular mobile phase solutions, column geometry, including column diameter and length, pH, flow rate, pressure and temperature of column operation, and other parameters that can be varied to obtain the desired separation of molecular tags. A molecular tag, or chromatographic property of a molecular tag, can be detected using a variety of chromatography methods.

Although standard liquid chromatography methods can be used to separate molecular tags, high pressure (or performance) liquid chromatography (HPLC) provides the advantages of high resolution, increased speed of analysis, greater reproducibility, and ease of automation of instrument operation and data analysis. HPLC methods also allow separation of molecular tags based on a variety of physiochemical properties. Molecular tags having similar properties can be used together in the same experiment since HPLC can be used to differentiate between closely related tags. The high degree of resolution achieved using HPLC methods allows the use of large sets of tagged probes because the resulting molecular tags can be distinguished from each other. The ability to detect large sets of tagged probes is an advantage when performing multiplexed detection of target nucleic acids and target analytes. As used herein, "HPLC" refers to a liquid phase chromatographic separation that (i) employs a rigid cylindrical separation column having a length of up to 300 mm and an inside diameter of up to 5 mm, (ii) has a solid phase comprising rigid spherical particles (e.g. silica, alumina, or the like) having the same diameter of up to 5 µm packed into the separation column, (iii) takes place at a temperature in the range of from 35° C. to 80° C. and at column pressure up to 150 bars, and (iv) employs a flow rate in the range of from 1 µL/min to 4 µL/min. Solid phase particles for use in HPLC are further characterized in (i) having a narrow size distribution about the mean particle diameter, with substantially all particle diameters being within 10% of the mean, (ii) having the same pore size in the range of from 70 to 300 angstroms, (iii) having a surface area in the range of from 50 to 250 $m^2/g$, and (iv) having a bonding phase density (i.e. the number of retention ligands per unit area) in the range of from 1 to 5 per $nm^2$.

Sets of molecular tags detected in a single experiment generally are a group of chemically related molecules that differ by mass, charge, mass-charge ratio, detectable tag, such as differing fluorophores or isotopic labels, or other unique characteristic. Therefore, both the chemical nature of the molecular tag and the particular differences among molecular tags in a group of molecular tags can be considered when selecting a suitable chromatographic medium for separating molecular tags in a sample.

Reverse phase chromatography is a type of chromatography in which the chemically bonded phase is hydrophobic (nonpolar) than the mobile phase. This is "reversed" from normal phase chromatography, in which the stationary phase is hydrophilic (polar), and the starting mobile phase is more nonpolar than the stationary phase. Mobile phase gradients that increase in concentration of an organic modifier (usually acetonitrile or methanol) are commonly used in reverse phase HPLC. These gradients elute solute molecules in order of increasing hydrophobicity. Exemplary mobile phases for use with the invention to separate water soluble molecular tags include but are not limited to water, nitromethane, methanol, dimethyl sulfoxide, dimethylformamide, acetonitrile, acetic acid, methoxyethanol, benzyl alcohol, acetone, and the like. The mobile phases may be used isocratically or they may be combined and delivered to a column in continuously varying proportions. In the latter case, usually two solvents are combined in proportions that vary linearly over time, i.e. gradient delivery.

Various mobile phase additives can be used to provide different selectivity to improve separation of molecular tags. For example, ion pairing reagents may be used in reverse phase HPLC methods. Exemplary ion pairing reagents include trifluoroacetic acid (TFA), which is an anionic ion-pairing reagent, and tetrabutylammonium phosphate, which is a cationic ion pairing reagent.

Reverse phase HPLC can be used to separate a variety of types of molecular tags, including organic molecules, oligonucleotides, peptides and polypeptides. Reversed phase HPLC is particularly useful for separating peptide or polypeptide molecular tags that are closely related to each other. Exemplary reversed phase chromatography media for separating molecular tags include particles, e.g. silica or alumina, having bonded to their surfaces retention ligands, such as phenyl groups, cyano groups, or aliphatic groups selected from the group including $C_8$ through $C_{18}$. Preferably, the particles have a pore size in the range of from 80 to 300 angstroms.

Exemplary reversed phase chromatography media for separating molecular tags that are peptides, include particles having aliphatic retention ligands in the range of from $C_8$ to $C_{18}$ bonded to their surfaces and having a pore size of between 60 and 80 angstroms. Commercial preparations useful for separating molecular tags include, for example, Apex WP Octadecyl $C_{18}$, Octyl $C_8$, Butyl $C_4$ and Phenyl, Aquaprep RP-3000 $C_4$ and $C_8$, Bakerbond WP Octadecyl $C_{18}$, Octyl $C_8$, Butyl $C_4$ and Diphenyl.

Prior to separation by HPLC, a sample can be fractionated or subjected to a pre-separation step, for example, to remove particulate matter or molecules other than reporter tags. In addition to standard biochemical methods for fractionating samples, such as centrifugation, precipitation, filtration and extraction, a variety of HPLC pre-columns or guard columns can be used for this purpose.

Separated molecular tags can be detected using a variety of analytical methods, including detection of intrinsic properties of molecular tags, such as absorbance, fluorescence or electrochemical properties, as well as detection of a detection group or moiety attached to a molecular tag. Although not required, a variety of detection groups or moieties can be attached to molecular tags to facilitate detection after chromatographic separation.

Detection methods for use with liquid chromatography are well known, commercially available, and adaptable to automated and high-throughput sampling. The detection method selected for analysis of molecular tags will depend upon whether the molecular tags contain a detectable group or moiety, the type of detectable group used, and the physicochemical properties of the molecular tag and detectable group, if used. Detection methods based on fluorescence, electrolytic conductivity, refractive index, and evaporative light scattering can be used to detect various types of molecular tags.

A variety of optical detectors can be used to detect a molecular tag separated by liquid chromatography. Methods for detecting nucleic acids, polypeptides, peptides, and other macromolecules and small molecules using ultraviolet (UV)/visible spectroscopic detectors are well known, making UV/visible detection the most widely used detection method for HPLC analysis. Infrared spectrophotometers also can be used to detect macromolecules and small molecules when used with a mobile phase that is a transparent polar liquid.

Variable wavelength and diode-array detectors represent two commercially available types of UV/visible spectrophotometers. A useful feature of some variable wavelength UV detectors is the ability to perform spectroscopic scanning and precise absorbance readings at a variety of wavelengths while the peak is passing through the flowcell. Diode array technology provides the additional advantage of allowing absorbance measurements at two or more wavelengths, which permits the calculation of ratios of such absorbance measurements. Such absorbance rationing at multiple wavelengths is particularly helpful in determining whether a peak represents one or more than one molecular tag.

Fluorescence detectors can also be used to detect fluorescent molecular tags, such as those containing a fluorescent detection group and those that are intrinsically fluorescent. Typically, fluorescence sensitivity is relatively high, providing an advantage over other spectroscopic detection methods when molecular tags contain a fluorophore. Although molecular tags can have detectable intrinsic fluorescence, when a molecular tag contains a suitable fluorescent detection group, it can be possible to detect a single molecular tag in a sample.

Electrochemical detection methods are also useful for detecting molecular tags separated by HPLC. Electrochemical detection is based on the measurement of current resulting from oxidation or reduction reaction of the molecular tags at a suitable electrode. Since the level of current is directly proportional to molecular tag concentration, electrochemical detection can be used quantitatively, if desired.

Mass spectrometry methods also can be used to detect molecular tags separated by HPLC. Mass spectrometers can resolve ions with small mass differences and measure the mass of ions with a high degree of accuracy and sensitivity. Mass spectrometry methods are well known in the art (see Burlingame et al. *Anal. Chem.* 70:647R–716R (1998); Kinter and Sherman, Protein Sequencing and Identification Using Tandem Mass Spectrometry Wiley-Interscience, New York (2000)).

Analysis of data obtained using any detection method, such as spectral deconvolution and quantitative analysis can be manual or computer-assisted, and can be performed using automated methods. A variety of computer programs can be used to determine peak integration, peak area, height and retention time. Such computer programs can be used for convenience to determine the presence of a molecular tag qualitatively or quantitatively. Computer programs for use with HPLC and corresponding detectors are well known to those skilled in the art and generally are provided with commercially available HPLC and detector systems.

The particular molecular tags contained in a sample can be determined, for example, by comparison with a database of known chromatographic properties of reference molecular tags, or by algorithmic methods such as chromatographic pattern matching, which allows the identification of components in a sample without the need to integrate the peaks individually. The identities of molecular tags in a sample can be determined by a combination of methods when large numbers of molecular tags are simultaneously identified, if desired.

A variety of commercially available systems are well-suited for high throughput analysis of molecular tags. Those skilled in the art can determine appropriate equipment, such as automated sample preparation systems and autoinjection systems, useful for automating HPLC analysis of molecular tags. Automated methods can be used for high-throughput analysis of molecular tags, for example, when a large number of samples are being processes or for multiplexed application of the methods of the invention for detecting target analytes. An exemplary HPLC instrumentation system suitable for use with the present invention is the Agilent 1100 Series HPLC system (Agilent Technologies, Palo Alto, Calif.).

Those skilled in the art will be aware of quality control measures useful for obtaining reliable analysis of molecular tags, particular when analysis is performed in a high-throughput format. Such quality control measures include the use of external and internal reference standards, analysis of chromatograph peak shape, assessment of instrument performance, validation of the experimental method, for example, by determining a range of linearity, recovery of sample, solution stability of sample, and accuracy of measurement.

In another aspect of the invention, molecular tags are separated by capillary electrochromatography (CEC). In CEC, the liquid phase is driven by electroosmotic flow through a capillary-sized column, e.g. with inside diameters in the range of from 30 to 100 µm. CEC is disclosed in Svec, Adv. Biochem. Eng. Biotechnol. 76: 1–47 (2002); Vanhoenacker et al, Electrophoresis, 22: 4064–4103 (2001); and like references. CEC column may used the same solid phase materials as used in conventional reverse phase HPLC and additionally may use so-called "monolithic" non-particular packings. In some forms of CEC, pressure as well as electroosmosis drives a sample-containing solvent through a column.

Synthesis of Molecular Tags and Binding Compounds

The chemistry for performing the types of syntheses to form the charge-imparting moiety or mobility modifier as a peptide chain is well known in the art. See, for example, Marglin, et al., Ann. Rev. Biochem. (1970) 39:841–866. In general, such syntheses involve blocking, with an appropriate protecting group, those functional groups that are not to be involved in the reaction. The free functional groups are then reacted to form the desired linkages. The peptide can be produced on a resin as in the Merrifield synthesis (Merrifield, J. Am. Chem. Soc. (1980) 85:2149–2154 and Houghten et al., Int. J. Pep. Prot. Res. (1980) 16:311–320. The peptide is then removed from the resin according to known techniques.

A summary of the many techniques available for the synthesis of peptides may be found in J. M. Stewart, et al., "Solid Phase Peptide Synthesis, W. H. Freeman Co, San Francisco (1969); and J. Meienhofer, "Hormonal Proteins and Peptides", (1973), vol. 2, p. 46, Academic Press (New York), for solid phase peptide synthesis; and E. Schroder, et al., "The Peptides", vol. 1, Academic Press (New York), 1965 for solution synthesis.

In general, these methods comprise the sequential addition of one or more amino acids, or suitably protected amino acids, to a growing peptide chain. Normally, a suitable protecting group protects either the amino or carboxyl group of the first amino acid. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide. The protecting groups are removed, as desired, according to known methods depending on the particular protecting group utilized. For example, the protecting group may be removed by reduction with hydrogen and palladium on charcoal, sodium in liquid ammonia, etc.; hydrolysis with trifluoroacetic acid, hydrofluoric acid, and the like.

For synthesis of binding compounds employing phosphoramidite, or related, chemistry many guides are available in the literature: Handbook of Molecular Probes and Research Products, 8$^{th}$ edition (Molecular Probes, Inc., Eugene, Oreg., 2002); Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Many of these chemistries allow components of the binding compound to be conveniently synthesized on an automated DNA synthesizer, e.g. an Applied Biosystems, Inc. (Foster City, Calif.) model 392 or 394 DNA/RNA Synthesizer, or the like.

Synthesis of molecular tag reagents comprising nucleotides as part of the mobility-modifying moiety can be easily and effectively achieved via assembly on a solid phase support using standard phosphoramidite chemistries. The resulting mobility modifying moiety may be linked to the label and/or polypeptide-binding moiety as discussed above.

Exemplary Synthetic Approaches for Molecular Tags

Figure 2:
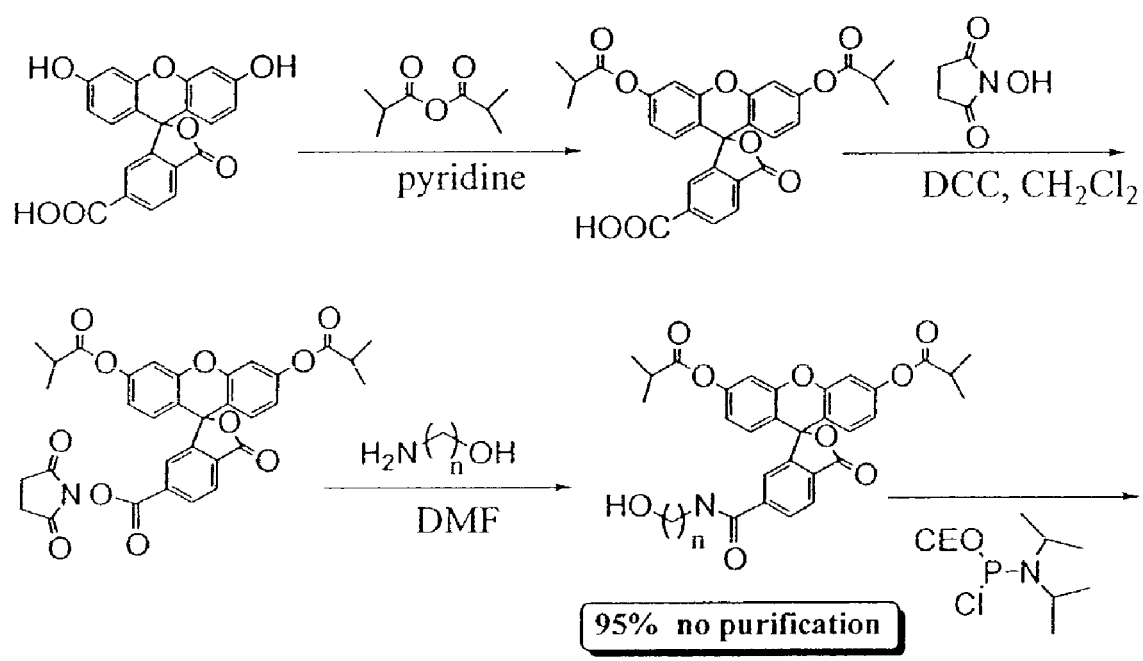
FIG. 2 illustrates one exemplary synthetic approach starting with commercially available 6-carboxy fluorescein, where the phenolic hydroxyl groups are protected using an anhydride. Upon standard extractive workup, a 95% yield of product is obtained. This material is phosphitylated to generate the phosphoramidite monomer.
Figure 3:
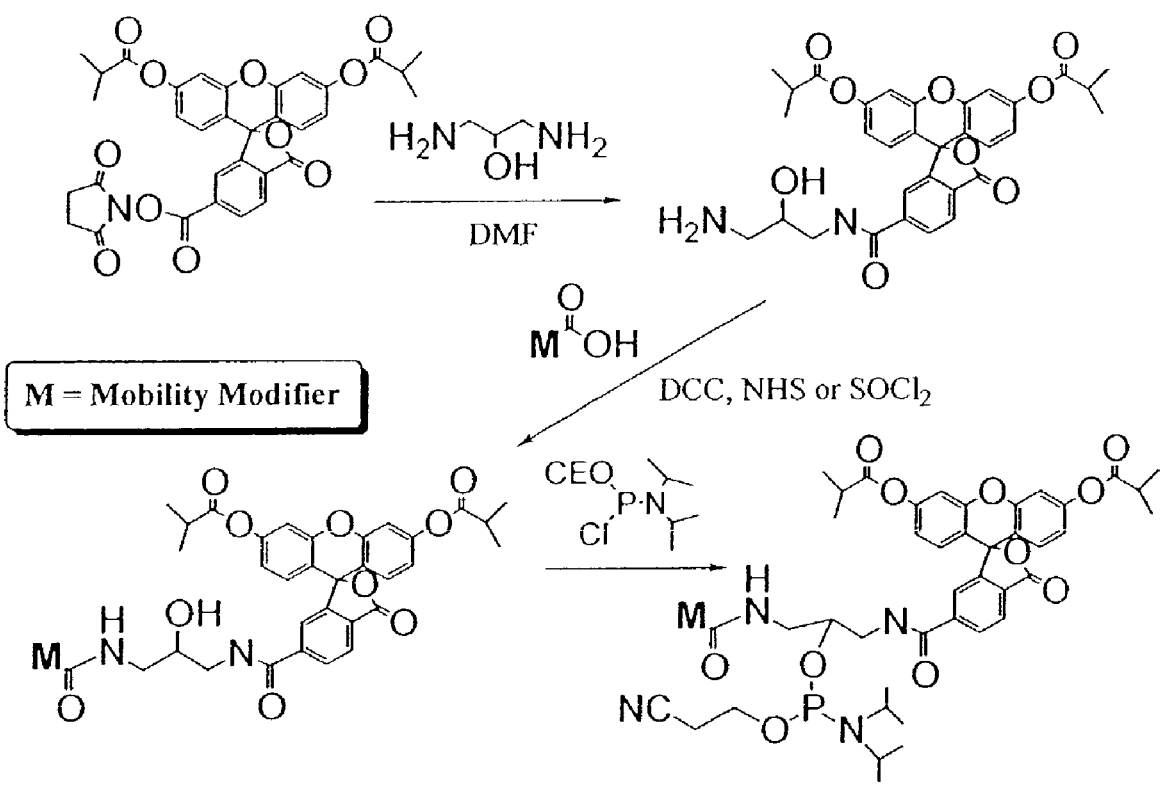
FIG. 3 illustrates the use of a symmetrical bis-amino alcohol linker as the amino alcohol with the second amine then coupled with a multitude of carboxylic acid derivatives.

One exemplary synthetic approach is outlined in FIG. 1. Starting with commercially available 6-carboxy fluorescein, the phenolic hydroxyl groups are protected using an anhydride. Isobutyric anhydride in pyridine was employed but other variants are equally suitable. It is important to note the significance of choosing an ester functionality as the protecting group. This species remains intact throughout the phosphoramidite monomer synthesis as well as during oligonucleotide construction. These groups are not removed until the synthesized oligonucleotide is deprotected using ammonia. After protection the crude material is then activated in situ via formation of an N-hydroxysuccinimide ester (NHS-ester) using DCC as a coupling agent. The DCU by product is filtered away and an amino alcohol is added. Many amino alcohols are commercially available some of which are derived from reduction of amino acids. When the amino alcohol is of the form "$H_2N$—$(CH_2)_n$—$OH$," n is in the range of from 2 to 12, and more preferably, from 2 to 6. Only the amine is reactive enough to displace N-hydroxysuccinimide. Upon standard extractive workup, a 95% yield of product is obtained. This material is phosphitylated to generate the phosphoramidite monomer. For the synthesis of additional molecular tags, a symmetrical bis-amino alcohol linker is used as the amino alcohol (FIG. 2). As such, the second amine is then coupled with a multitude of carboxylic acid derivatives (exemplified by several possible benzoic acid derivatives shown in FIG. 3 prior to the phosphitylation reaction.

Figure 4:
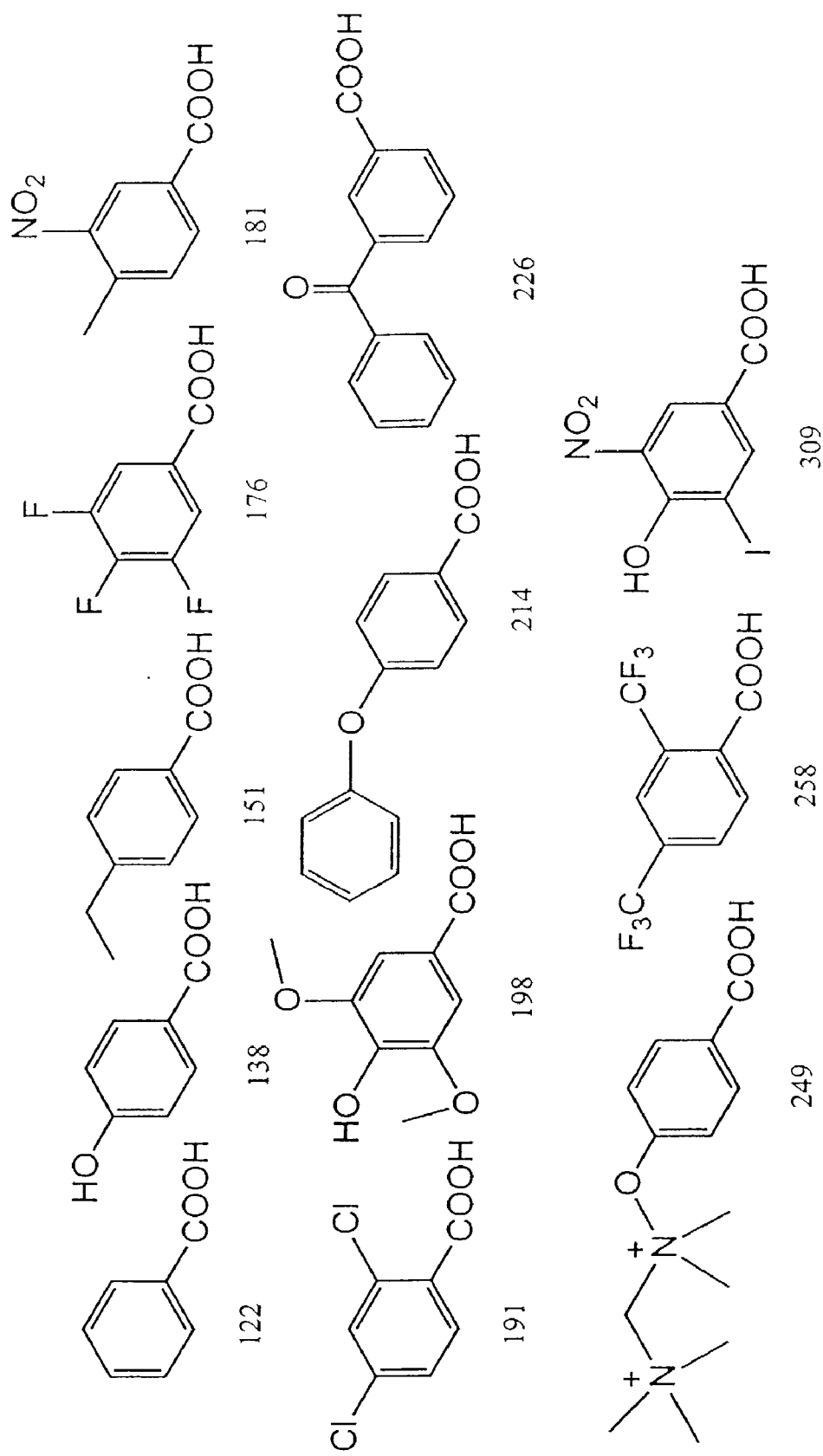
FIG. 4 shows the structure of several benzoic acid derivatives that can serve as mobility modifiers.
Figure 5:
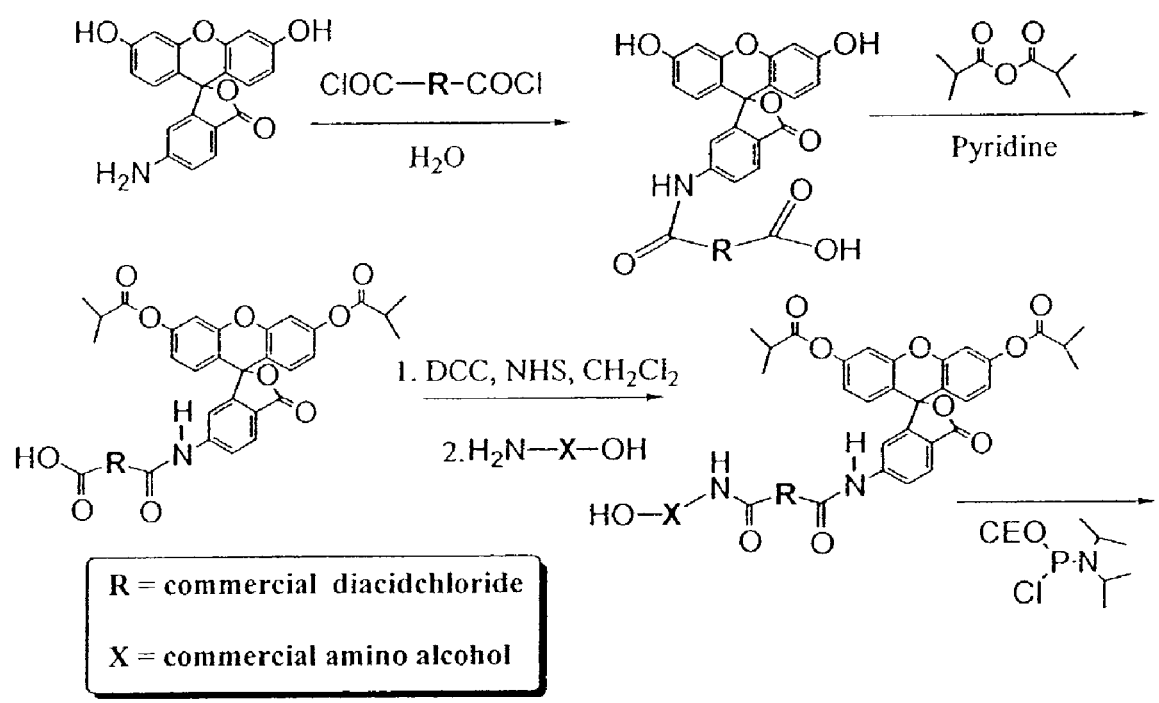
FIG. 5 illustrates the use of an alternative strategy that uses 5-aminofluorescein as starting material and the same series of steps to convert it to its protected phosphoramidite monomer.

Alternatively, molecular tags may be made by an alternative strategy that uses 5-aminofluorescein as starting material (FIG. 4). Addition of 5-aminofluorescein to a great excess of a diacid dichloride in a large volume of solvent allows for the predominant formation of the monoacylated product over dimer formation. The phenolic groups are not reactive under these conditions. Aqueous workup converts the terminal acid chloride to a carboxylic acid. This product is analogous to 6-carboxyfluorescein, and using the same series of steps is converted to its protected phosphoramidite monomer. There are many commercially available diacid dichlorides and diacids, which can be converted to diacid dichlorides using $SOCl_2$ or acetyl chloride. There are many commercial diacid dichlorides and amino alcohols (FIG. 5). These synthetic approaches are ideally suited for combinatorial chemistry.

The molecular tags constructed with the schemes of FIGS. 1, 2, and 4 are further reacted either before or after phosphitylation to attach a cleavable linkage, e.g. using chemistry as described below.

The molecular tag may be assembled having an appropriate functionality at one end for linking to the polypeptide-binding moieties. A variety of functionalities can be employed. Thus, the functionalities normally present in a peptide, such as carboxy, amino, hydroxy and thiol may be the targets of a reactive functionality for forming a covalent bond. The molecular tag is linked in accordance with the chemistry of the linking group and the availability of functionalities on the polypeptide-binding moiety. For example, as discussed above for antibodies, and fragments thereof such as Fab' fragments, specific for a polypeptide, a thiol group will be available for using an active olefin, e.g., maleimide, for thioether formation. Where lysines are available, one may use activated esters capable of reacting in water, such as nitrophenyl esters or pentafluorophenyl esters, or mixed anhydrides as with carbodiimide and half-ester carbonic acid. There is ample chemistry for conjugation in the literature, so that for each specific situation, there is ample precedent in the literature for the conjugation.

In an illustrative synthesis a diol is employed. Examples of such diols include an alkylene diol, polyalkylene diol, with alkylene of from 2 to 3 carbon atoms, alkylene amine or poly(alkylene amine) diol, where the alkylenes are of from 2 to 3 carbon atoms and the nitrogens are substituted, for example, with blocking groups or alkyl groups of from 1–6 carbon atoms, where one diol is blocked with a conventional protecting group, such as a dimethyltrityl group. This group can serve as the mass-modifying region and with the amino groups as the charge-modifying region as well. If desired, the mass modifier can be assembled by using building blocks that are joined through phosphoramidite chemistry. In this way the charge modifier can be interspersed between the mass modifier. For example, a series of polyethylene oxide molecules having 1, 2, 3, n units may be prepared. To introduce a number of negative charges, a small polyethylene oxide unit may be employed. The mass and charge-modifying region may be built up by having a plurality of the polyethylene oxide units joined by phosphate units. Alternatively, by employing a large spacer, fewer phosphate groups would be present, so that without large mass differences, large differences in mass-to-charge ratios may be realized.

The chemistry that is employed is the conventional chemistry used in oligonucleotide synthesis, where building blocks other than nucleotides are used, but the reaction is the conventional phosphoramidite chemistry and the blocking group is the conventional dimethoxytrityl group. Of course, other chemistries compatible with automated synthesizers can also be used. However, it is desirable to minimize the complexity of the process.

As mentioned above, in one embodiment the hub nucleus is a hydrophilic polymer, generally, an addition or condensation polymer with multiple functionality to permit the attachment of multiple moieties. One class of polymers that is useful for the reagents of the present invention comprises the polysaccharide polymers such as dextrans, sepharose, polyribose, polyxylose, and the like. For example, the hub may be dextran to which multiple molecular tags may be attached in a cleavable manner consistent with the present invention. A few of the aldehyde moieties of the dextran remain and may be used to attach the dextran molecules to amine groups on an oligonucleotide by reductive amination. In another example using dextran as the hub nucleus, the dextran may be capped with succinic anhydride and the resulting material may be linked to amine-containing oligonucleotides by means of amide formation.

Besides the nature of the linker and mobility-modifying moiety, as already indicated, diversity can be achieved by the chemical and optical characteristics of the fluorescer, the use of energy transfer complexes, variation in the chemical nature of the linker, which affects mobility, such as folding, interaction with the solvent and ions in the solvent, and the like. As already suggested, in one embodiment the linker is an oligomer, where the linker may be synthesized on a support or produced by cloning or expression in an appropriate host. Conveniently, polypeptides can be produced where there is only one cysteine or serine/threonine/tyrosine, aspartic/glutamic acid, or lysine/arginine/histidine, other than an end group, so that there is a unique functionality, which may be differentially functionalized. By using protective groups, one can distinguish a side-chain functionality from a terminal amino acid functionality. Also, by appropriate design, one may provide for preferential reaction between the same functionalities present at different sites on the linking group. Whether one uses synthesis or cloning for preparation of oligopeptides, will to a substantial degree depend on the length of the linker.

Methods of Using Binding Compositions of the Invention

In one aspect, the invention provides a method for detecting or measuring one or more target analytes from biological sources. Conventional methodologies are employed to prepare samples for analysis. For example, for protein analytes guidance in sample preparation can be found in Scopes, Protein Purification, chapter 2 (Springer-Verlag, N.Y.), where a range of procedures are disclosed for preparing protein extracts from different sources. Preparative techniques include mild cell lysis by osmotic disruption of cellular membranes, to enzymatic digestion of connective tissue followed by osmotic-based lysis, to mechanical homogenization, to ultrasonication.

For sources containing target polynucleotides, guidance for sample preparation techniques can be found in standard treatises, such as Sambrook et al, Molecular Cloning, Second Edition (Cold Spring Harbor Laboratory Press, New York, 1989); Innis et al, editors, PCR Protocols (Academic Press, New York, 1990); Berger and Kimmel, "Guide to Molecular Cloning Techniques," Vol. 152, Methods in Enzymology (Academic Press, New York, 1987); or the like. For mammalian tissue culture cells, or like sources, samples of target RNA may be prepared by conventional cell lysis techniques (e.g. 0.14 M NaCl, 1.5 mM MgCl2, 10 mM Tris-Cl (pH 8.6), 0.5% Nonidet P-40, 1 mM dithiothreitol, 1000 units/mL placental RNAase inhibitor or 20 mM vanadyl-ribonucleoside complexes).

In carrying out the assays, the components, i.e., the sample, composition of microparticles, and in some embodiments a cleavage-inducing moiety, are combined in an assay medium in any order, usually simultaneously. Alternatively, one or more of the reagents may be combined with one or more of the remaining agents to form a subcombination. The subcombination can then be subjected to incubation. Then, the remaining reagents or subcombination thereof may be combined and the mixture incubated. The amounts of the reagents are usually determined empirically. The components are combined under binding conditions, usually in an aqueous medium, generally at a pH in the range of about 5 to about 10, with buffer at a concentration in the range of about 10 to about 200 mM. These conditions are conventional, where conventional buffers may be used, such as phosphate, carbonate, HEPES, MOPS, Tris, borate, etc., as well as other conventional additives, such as salts, stabilizers, organic solvents, etc. The aqueous medium may be solely water or may include from 0.01 to 80 or more volume percent of a co-solvent.

The combined reagents are incubated for a time and at a temperature that permit a substantial number of binding events to occur. The time for incubation after combination of the reagents varies depending on the (i) nature and expected concentration of the analyte being detected, (ii) the mechanism by which the binding compounds for complexes with analytes, and (iii) the affinities of the specific reagents employed. Moderate temperatures are normally employed for the incubation and usually constant temperature. Incubation temperatures will normally range from about 5° to 99° C., usually from about 15° to 85° C., more usually 35° to 75° C.

Generally, the concentrations of the various agents involved with an assay of the invention will vary with the concentration range of the individual analytes in the samples to be analyzed, generally being in the range of about 10 nM to about 10 mM. Buffers will ordinarily be employed at a concentration in the range of about 10 to about 200 mM. The concentration of each analyte will generally be in the range of about 1 pM to about 100 µM, more usually in the range of about 100 pM to about 10 µM. In specific situations the concentrations may be higher or lower, depending on the nature of the analyte, the affinity of the binding compounds, the efficiency of release of the molecular tags, the sensitivity with which the molecular tags are detected, and the number of analytes to be determined in the assay, as well as other considerations.

In heterogeneous assays it is required that the unbound labeled reagent be separable from the bound labeled reagent. This can be achieved in a variety of ways, each requiring a reagent bound to a solid support that distinguishes between the complex of labeled reagent and polypeptide. The solid support may be a vessel wall, e.g., microtiter well plate well, capillary, plate, slide, beads, including magnetic beads, liposomes, or the like. The primary characteristics of the solid support is that it permits segregation of the bound labeled specific binding member from unbound probe and that the support does not interfere with the formation of the binding complex, nor the other operations of the determination.

The solid support may have the complex directly or indirectly bound to the support. For directly bound, one may have the binding compound or second binding compound covalently or non-covalently bound to the support. The surface may be activated with various functionalities that will form covalent bonds with the second binding compound. These groups may include imino halides, activated carboxyl groups, e.g., mixed anhydrides or acyl halides, amino groups, α-halo or pseudohaloketones, etc. A specific binding member bound to the surface of the support may be used to bind a member of the complex.

In some embodiments, where components of the assay mixture interfere with a chromatographic analysis, the molecular tags may be required to be separated from the assay mixture prior to chromatographic analysis, or certain components of the assay mixture, e.g. binding moieties with unreleased molecular tags, may be required to be excluded from the chromatographic analysis. Depending on the nature of the molecular tags and the components of the assay mixture, one may sequester or adsorb or exclude such binding moieties by using guard column, and the like. Alternatively, one may have a capture ligand attached to binding compounds for the purpose of removing such interfering components in the mixture.

An additional degree of flexibility can be conferred on an assay by the stage at which the molecular tags are labeled. A molecular tag may contain a functionality allowing it to bind to a label after reaction with the sample is complete. In this embodiment, a molecular tag comprising a functionality for binding to a detectable label is combined with a sample. After a binding reaction takes place and molecular tags are released, additional reagents are combined in a sample vessel with the products of the first reaction, which react with the released molecular tags to add a detectable label.

For quantitation, one may choose to use controls, which provide a signal in relation to the amount of the target that is present or is introduced. A control to allow conversion of relative fluorescent signals into absolute quantities is accomplished by addition of a known quantity of a fluorophore to each sample before separation of the molecular tags. Any fluorophore that does not interfere with detection of the molecular tag signals can be used for normalizing the fluorescent signal. Such standards preferably have separation properties that are different from those of any of the molecular tags in the sample, and could have the same or a different emission wavelength. Exemplary fluorescent molecules for standards include ROX, FAM, and fluorescein and derivatives thereof.

One example of an assay in accordance with the present invention involves the detection of the phosphorylation of a polypeptide. The sample comprises cellular material and the post-translational modification is the phosphorylation of a particular polypeptide, referred to as a target polypeptide. The sample is combined with a second binding compound comprising a photosensitizer linked to a metal affinity agent to which is bound a metal ion. If the phosphorylated target polypeptide is present, the phosphate group binds to the metal-metal affinity agent complex. A binding composition is combined with the above reaction mixture. The binding composition comprises an antibody for the target polypeptide, to which is cleavably linked one or more molecular tags. The cleavable linkage comprises a moiety that is cleavable by singlet oxygen. After addition of the binding composition and an appropriate incubation period, the reaction mixture is irradiated with light to excite the photosensitizer, which generates singlet oxygen. The cleavable moiety is cleaved by the singlet oxygen because the cleavable moiety is in close proximity to the photosensitizer and the active species, namely, singlet oxygen, retains sufficient activity to cleave the cleavable moiety and release a molecular tag. Binding compounds that do not become bound to target polypeptide because the target polypeptide is not present, or excess binding compound, or binding compound that binds to a polypeptide that is not phosphorylated, does not yield cleaved molecular tags because the activity of the singlet oxygen is very short-lived and the cleavable moiety in any binding compound that is not bound to the second binding compound by virtue of the presence of phosphorylated target polypeptide does not yield cleaved molecular tags. The released molecular tag is separated on the basis of its different mobility and detected on the basis of the detection moiety that remains attached to the mobility modifying moiety of the molecular tag. The presence and/or amount of the released molecular tag indicates the presence and/or amount of the target polypeptide.

The present invention finds particular use in multiplexed assays for target polypeptides. An example of an assay in accordance with this aspect of the present invention involves the detection of the phosphorylation of multiple polypeptides. The sample comprises cellular material and the post-translational modification is the phosphorylation of several polypeptides, referred to as target polypeptides. The sample is combined with a second binding compound comprising a photosensitizer linked to a metal affinity agent to which is bound a metal ion. The second binding compound is a class-specific reagent in that it binds to any phosphate group present in the reaction mixture. If the phosphorylated target polypeptides are present, the phosphate group binds to the metal-metal affinity agent complex. A plurality of binding compounds is combined with the above reaction mixture. Each of the binding compounds comprises an antibody for a particular target polypeptide, to which is cleavably linked an molecular tag that is unique for the particular target polypeptide. The cleavable link comprises a moiety that is cleavable by singlet oxygen. After addition of the binding compounds and an appropriate incubation period, the reaction mixture is irradiated with light to excite the photosensitizer, which generates singlet oxygen. The cleavable moiety is cleaved by the singlet oxygen because the cleavable moiety is in close proximity to the photosensitizer and the active species, namely, singlet oxygen, retains sufficient activity to cleave the cleavable moiety and release molecular tags from all binding compounds that are bound to a target polypeptide bound to the class-specific reagent. Again, binding compounds, which do not become bound to target polypeptides bound to the class-specific reagent, do not yield cleaved molecular tags for the reasons given above. The released molecular tags are separated on the basis of their differences in mobility and detected on the basis of the detection moiety that remains attached to the mobility modifying moiety of the molecular tag. The presence and/or amount of each of the released molecular tags indicate the presence and/or amount of each of the respective target polypeptides. In this fashion various cellular pathways may be studied on a real time basis. Protein phosphorylation and de-phosphorylation reactions may be studied to develop more information about metabolic regulation and signal transduction pathways. The above method may be repeated at various times during the cell cycle to follow the progression of the cell.

Another application of the present invention is to detect multiple phosphorylations of a target polypeptide. For example, it is desirable to know whether a polypeptide has been mono-phosphorylated, bis-phosphorylated or even higher multiples of phosphorylation. An example of an assay in accordance with this aspect of the present invention involves the detection of the degree of phosphorylation of a target polypeptide. The sample, which comprises cellular material, is combined with a second binding compound comprising a multiple photosensitizer molecules linked to a hub molecule to which multiple molecules of a metal affinity agent with bound metal are also linked. By appropriate titration of the class-specific reagent, the level of phosphorylation of the target polypeptide can be determined. If the phosphorylated target polypeptides are present, the phosphate group binds to the metal-metal affinity agent complex. An binding compound is combined with the above reaction mixture. The binding compound comprises an antibody for the particular target polypeptide, to which is cleavably linked an molecular tag that is unique for the particular target polypeptide. The cleavable link comprises a moiety that is cleavable by singlet oxygen. After addition of the binding compound and an appropriate incubation period, the reaction mixture is irradiated with light to excite the photosensitizer, which generates singlet oxygen. The cleavable moiety is cleaved by the singlet oxygen because the cleavable moiety is in close proximity to the photosensitizer. The active species, namely, singlet oxygen, retains sufficient activity to cleave the cleavable moiety and release molecular tags from the binding compound that is bound to a target polypeptide bound to the class-specific reagent. Again, binding compounds, which do not become bound to target polypeptides bound to the class-specific reagent, do not yield cleaved molecular tags for the reasons given above. The released molecular tag is separated on the basis of differences in mobility and detected on the basis of the detection moiety that remains attached to the mobility modifying moiety of the molecular tag. The presence and/or amount of the released molecular tag may be correlated with the amount of class-specific reagent added to determine the level of phosphorylation of the target polypeptide.

The present invention may be employed to determine the site or sites of phosphorylation on a target polypeptide. In an example of an assay in accordance with this aspect of the present invention, the sample, which comprises cellular material, is combined with a second binding compound comprising a chemical protease linked to a metal affinity agent to which is bound a metal ion. If the phosphorylated target polypeptide is present, the phosphate group binds to the metal-metal affinity agent complex. The chemical protease is activated by irradiation with light and site specific cleavage takes place on the target polypeptide whose phosphate group is bound to the metal affinity-metal complex. On the other hand, one or more binding compounds may be combined with the above reaction mixture to provide a detection moiety for the unique moieties. Each binding compound comprises an antibody for a cleaved moiety, to which is attached the detection moiety. The molecular tag and is separated on the basis of its different mobility and detected on the basis of the detection moiety that is attached. The presence of the molecular tag is indicative of the site of phosphorylation of the target polypeptide.

Taggant Use

Compositions of the invention may be used to label and track materials, such as liquids, wherein compositions of microparticles are mixed with the material or liquid to be identified or tracked, referred to herein as a "tagged material" or "tagged liquid." The origin or distribution of the tagged liquid or material can be determined by isolating a sample containing microparticles. The molecular tags of the microparticles are released, separated, and identified. Identity may determined by the presence or absence of a plurality of molecular tags (i.e. a "bar code"), or the presence, absence, or quantity of a plurality of molecular tags. For example, in the former case, if 15 different kinds of microparticles were employed in a composition, over 32,000 ($=2^{15}$) liquids or materials could be uniquely labeled. Guidance for the types of liquids and materials suitable for tagging, amounts to use for tagging, and method of extracting microparticles from a sample of such liquid or material is found in Slater et al, U.S. Pat. No. 5,643,728, which is incorporated by reference. In one aspect, liquids are labeled such that there are from 1 to 100 microparticles of each kind per mL of liquid, or from 10 to 1000 microparticles of each kind per mL of liquid. In another aspect, microparticles may be separated from the liquid by conventional techniques, such as flow cytometry. After such separation, molecular tags are cleaved, separated, and identified, thereby providing the identity of the liquid from which they were sampled.

Kits for Use of Microparticle Compositions

As a matter of convenience, predetermined amounts of reagents employed in the present invention can be provided in a kit in packaged combination. One exemplary kit for polypeptide analysis can comprise in packaged combination a microparticle composition of the invention and a second binding composition of the invention. The kit can further comprise standards for separating released molecular tags under a pretermined separation technique. In another embodiment, microparticles having pairs of molecular tags and binding moieties attached may be packaged separately.

The kits will include microparticle compositions having from 2 to 50, and more usually from 5 to 30, different kinds of microparticles each with a different molecular tag attached, such that the released molecular tags form distinguishable peaks upon separation using a specified separation protocol.

The kit may further comprise a device for conducting chromatography or electrophoresis as well as reagents that may be necessary to activate the cleavage-inducing moiety of the cleavage-inducing reagent. The kit can further include various buffered media, some of which may contain one or more of the above reagents.

The relative amounts of the various reagents in the kits can be varied widely to provide for concentrations of the reagents necessary to achieve the objects of the present invention. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. The kits may also include a written description of a method in accordance with the present invention as described above.

EXAMPLES

The invention is demonstrated further by the following syntheses and illustrative examples. Parts and percentages are by weight unless otherwise indicated. Temperatures are in degrees Centigrade (° C.) unless otherwise specified. The following preparations and examples illustrate the invention but are not intended to limit its scope. Unless otherwise indicated, peptides used in the following examples were prepared by synthesis using an automated synthesizer and were purified by gel electrophoresis or HPLC.

The following abbreviations have the meanings set forth below:

Tris HCl—Tris(hydroxymethyl)aminomethane-HCl (a 10× solution) from BioWhittaker, Walkersville, Md.
TLC—thin layer chromatography
BSA—bovine serum albumin, e.g. available from Sigma Chemical Company (St. Louis, Mo.), or like reagent supplier.
EDTA—ethylene diamine tetra-acetate from Sigma Chemical Company
FAM—carboxyfluorescein
EMCS—N-ε-maleimidocaproyloxy-succinimide ester
EDC—1-Ethyl-3-(3-dimethylaminopropyl)carbodiimide
NHS—N-hydroxysuccinimide
DCC—1,3-dicylcohexylcarbodiimide
DMF—dimethylformamide
Fmoc—N-(9-fluorenylmethoxycarbonyl)-

Example 1

Conjugation of Photosensitizer Molecules to Assay Reagents

Photosensitizer molecules are conjugated to a metal affinity agent, a boronic acid containing agent, a hub molecule, and the like by various conventional methods and configurations. For example, an activated (NHS ester, aldehyde, sulfonyl chloride, etc) photosensitizer (Rose Bengal, phthalocyanine, etc.) can be reacted with reactive amino-group containing moieties (aminodextran, amino-group containing agents (with appropriate protection of metal binding sites), other small and large molecules). The formed conjugates can be used directly (for example the antibody-photosensitizer conjugate, Biotin-LC-photosensitizer, etc.) in various assays. Also, the formed conjugates can be further coupled with antibody (for example, aminodextran-photosensitizer conjugate containing 20–200 photosensitizers and 200–500 amino-groups can be coupled to periodate oxidized antibody molecules to generate the antibody-dextran-sensitizer conjugate) or with the antibody and a particle. For example, aminodextran-sensitizer conjugate containing 20–200 photosensitizers and 200–500 amino-groups can be coupled to carboxylated polystyrene beads by EDC coupling chemistry to form the photosensitizer-aminodextran-particle conjugate. Methods for incorporation of a photosensitizer into a particle are given in, e.g., U.S. Pat. No. 5,340,716. Then the Na-periodate oxidized antibody molecules can be reacted with the amino-groups of the aminodextran molecule, in presence of sodium cyanoborohydride, to generate the antibody-dextran-photosensitizer-particle conjugate, referred to herein as a "photosensitizer bead." It should be noted that instead of an antibody molecule, avidin or other molecules can be used also.

Example 2

Preparation of Aminodextran Derivatized Microspheres

Aminodextran is prepared as described in Pollner, U.S. Pat. No. 6,346,384. Briefly, hydroxypropylaminodextran ($1NH_2/16$ glucose) is prepared by dissolving Dextran T-500 (Pharmacia, Uppsala, Sweden) (100 g) in 500 mL of $H_2O$ in a 3-neck round-bottom flask equipped with mechanical stirrer and dropping funnel. To the above solution is added 45 g sodium hydroxide, 50 mg EDTA, 50 mg $NaBH_4$, 50 mg hydroquinone and 200 g N-(2,3-epoxypropyl) phthalimide. The mixture is heated and stirred in a 90° C. water bath for 2 hr. A small aliquot is precipitated three times from methanol and analyzed by NMR. Appearance of a peak at 7.3–7.66 indicates incorporation of phthalimide. The main reaction mixture is precipitated by addition to 3.5 L of methanol and the solid is collected. The phthalimide protecting group is removed by dissolving the product above in 500 mL of 0.1 M acetate buffer, adding 50 mL of 35% hydrazine and adjusting the pH to 3.5. The mixture is heated at 80° C. for 1 hr, the pH is readjusted to 3.2, and the mixture is heated for an additional one-half hour. An aliquot is precipitated three times in methanol. The reaction mixture is neutralized to pH 8 and stored at room temperature. The product is purified by tangential flow filtration using a 50,000 molecular weight cut-off filter, washing with about 8 L water, 0.5 L of 0.1M HCl, 0.5 L of 0.01 M NaOH, and finally 3 L of water. The product solution is concentrated by filtration to 700 mL and then is lyophilized. Determination of reactive amines using trinitrobenzenesulfonate indicates about 1 amine per 16 glucose residues.

A solution of hydroxypropylaminodextran (synthesized as described above) is prepared at 2 mg/mL in 50 mM MES (pH 6). One hundred fifty (150) mg carboxyl-modified microspheres (Bangs Laboratories, Fishers, Ind.) in 7.5 mL water is added dropwise to 7.5 mL of the hydroxypropylaminodextran solution while vortexing. One hundred eighty eight (188) µL of EDAC solution (80 mg/mL) in water is added to the coating mixture while vortexing. The mixture is incubated overnight at room temperature in the dark. The mixture is diluted with 12 mL water and centrifuged. The supernatant is discarded and the bead pellet is suspended in 40 mL water by sonication. The beads are washed 3 times with water (40 mL per wash) by repeated centrifugation and suspension by sonication. The final pellet is suspended in 5 mL water.

Example 3

Conjugation and Release of a Molecular Tag

Figure 7A:
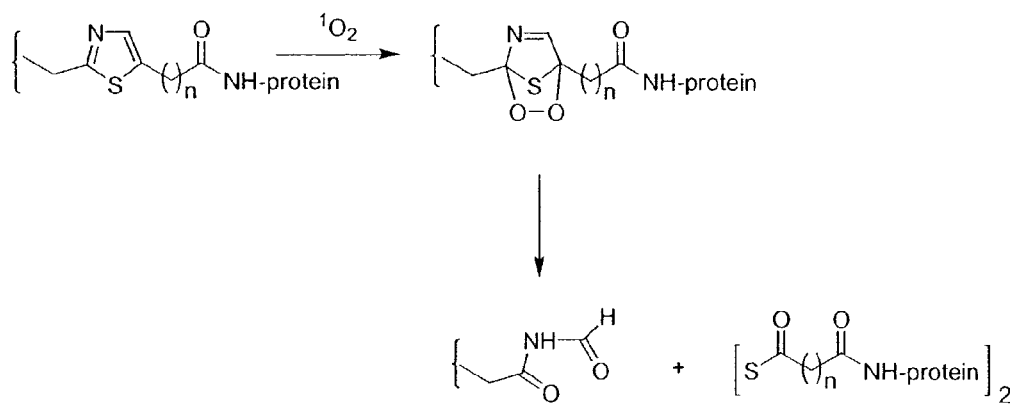
FIGS. 7A–F illustrate oxidation-labile linkages and their respective cleavage reactions mediated by singlet oxygen.
Figure 7B:
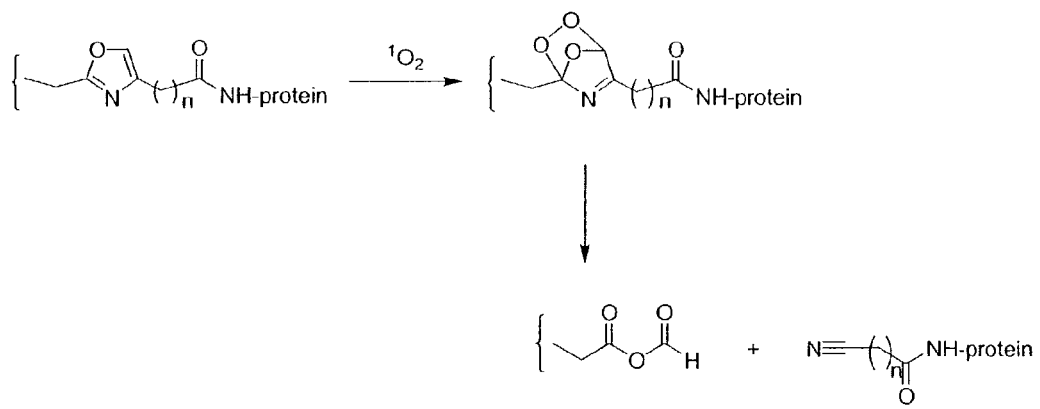
Figure 7C:
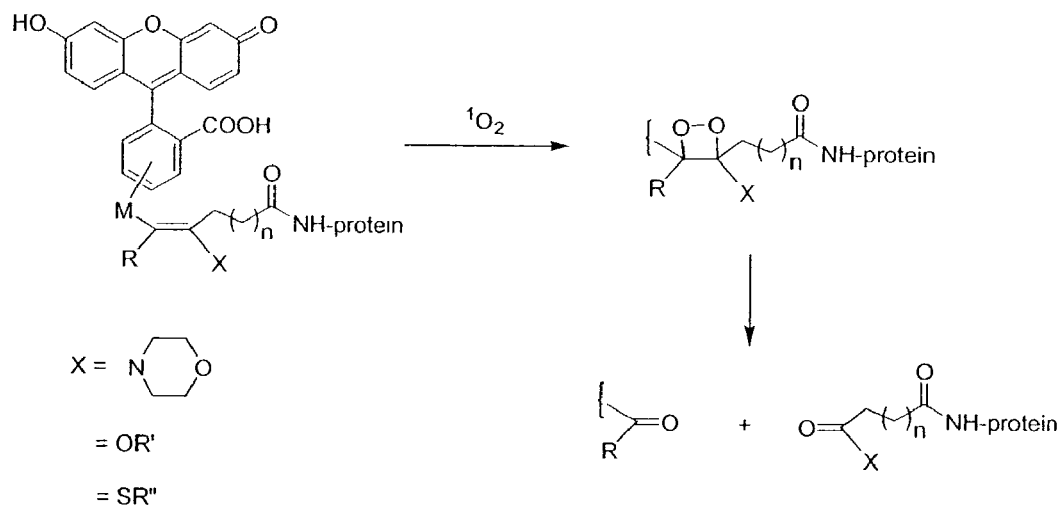
Figure 7D:
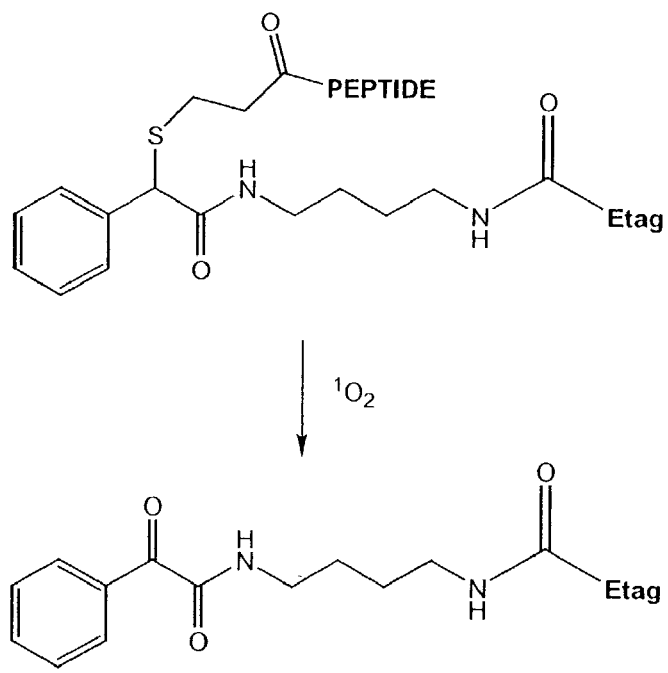
Figure 7E:
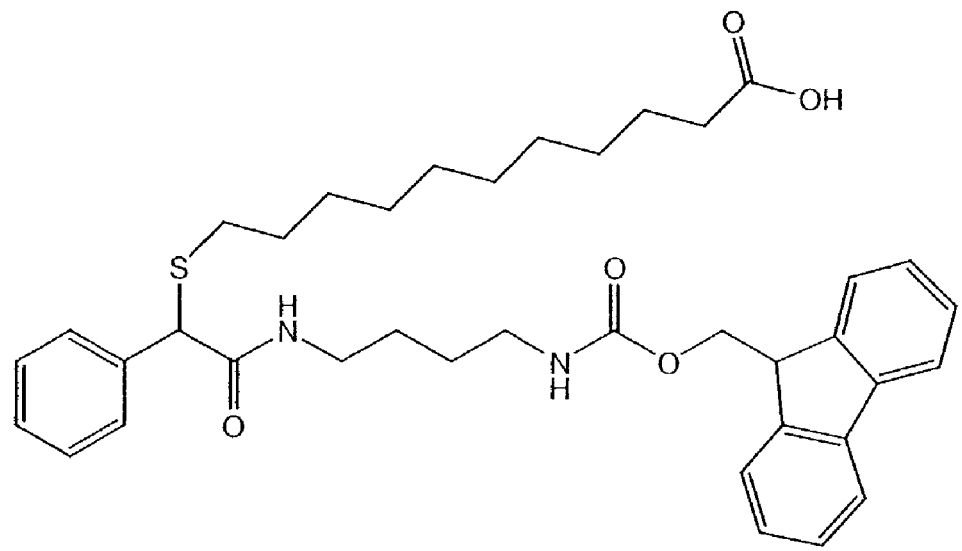
Figure 7F:
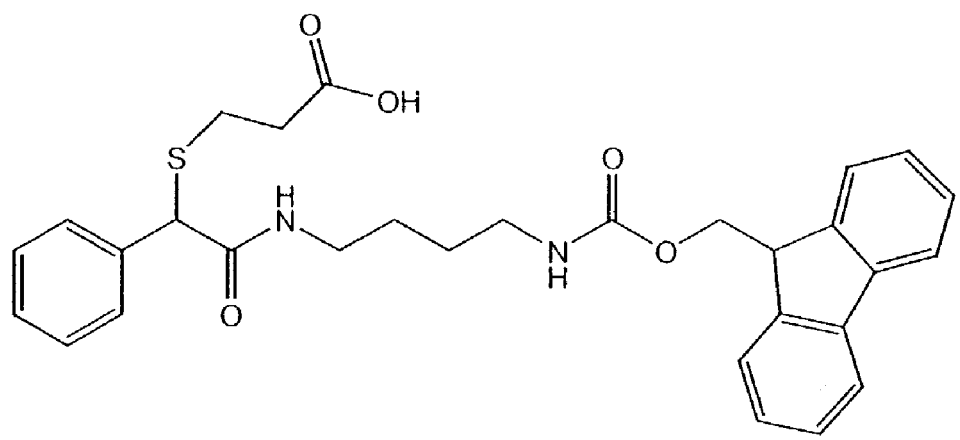
Figure 8A:
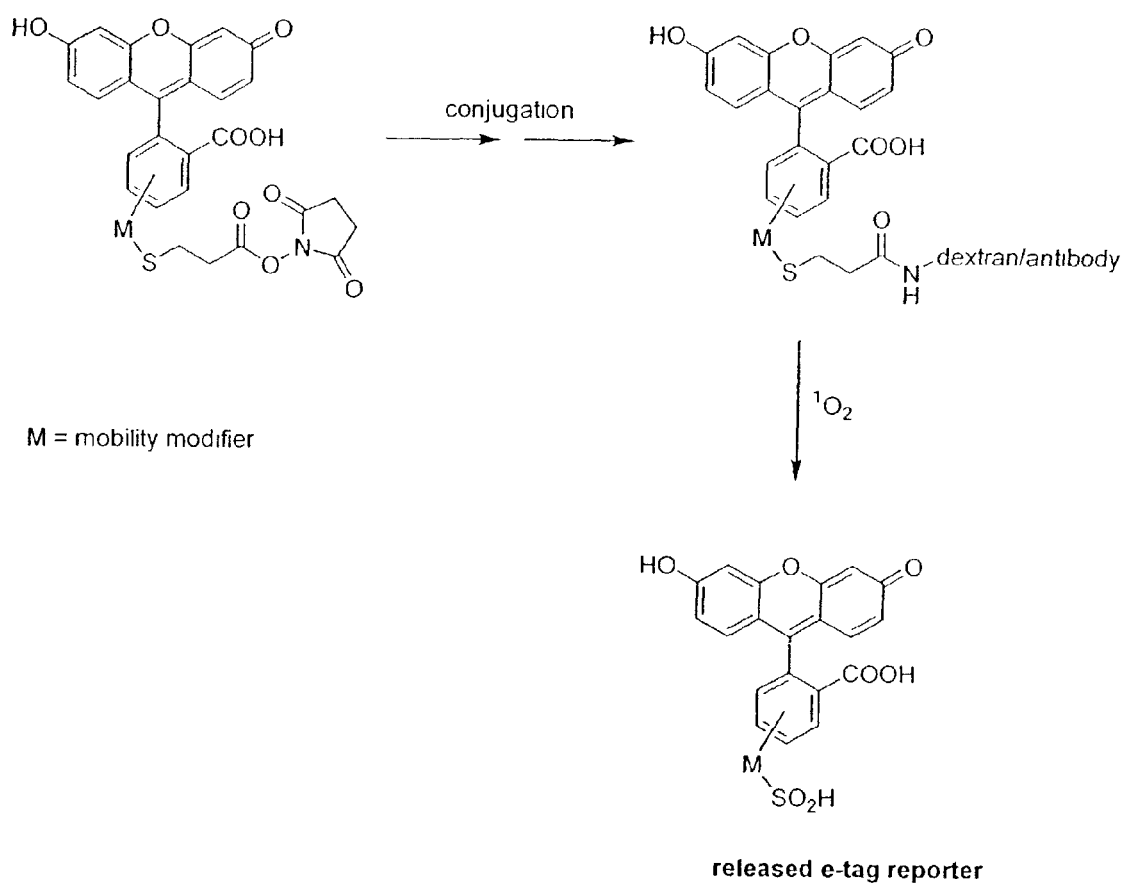
FIGS. 8A–B illustrate the general methodology for conjugation of an e-tag moiety to an antibody to form an e-tag probe, and the reaction of the resulting probe with singlet oxygen to produce a sulfinic acid moiety as the released molecular tag.
Figure 8B:
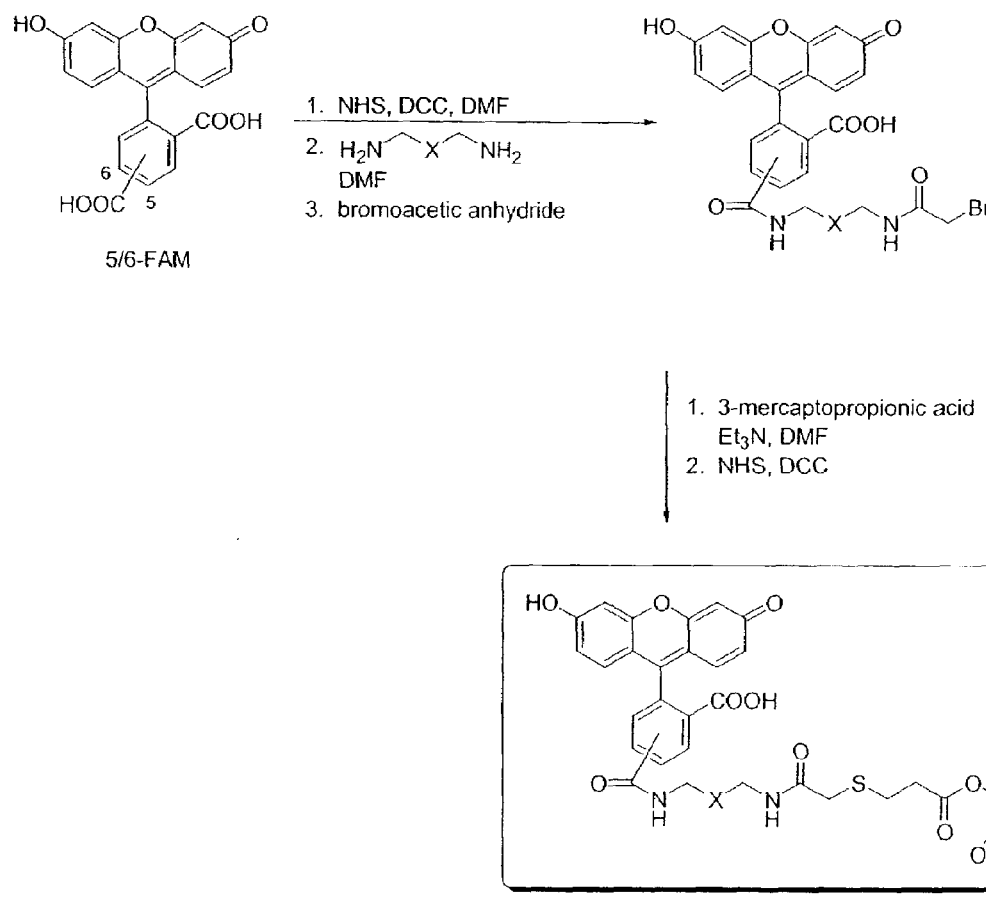

FIG. 7A–B summarize the methodology for conjugation of molecular tag precursor to an antibody or other binding moiety with a free amino group, and the reaction of the resulting conjugate with singlet oxygen to produce a sulfinic acid moiety as the released molecular tag. FIG. 8A–J shows several molecular tag reagents, most of which utilize 5- or 6-carboxyfluorescein (FAM) as starting material.

Example 4

Preparation of Pro2, Pro4, and Pro6 Through Pro13

Figure 9A:
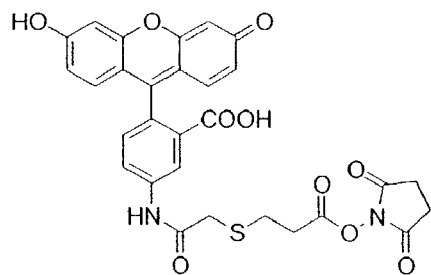
FIGS. 9A–J show the structures of e-tag moieties that have been designed and synthesized. (Pro1 is commercially available from Molecular Probes, Inc.)
Figure 9A:
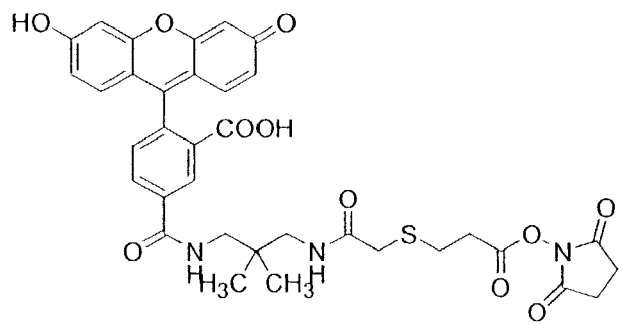
Figure 9A:
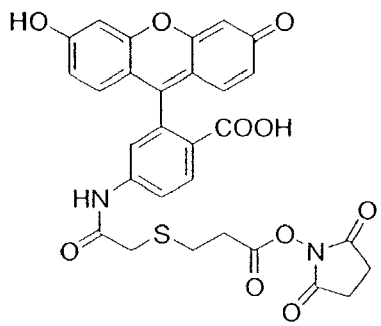
Figure 9A:
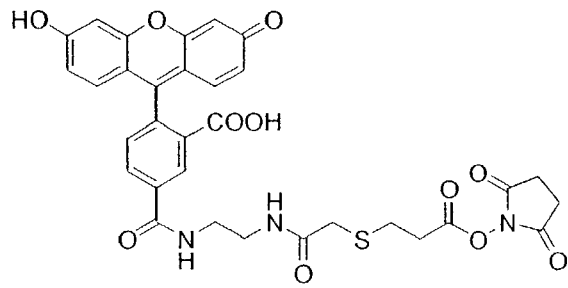

The scheme outlined in FIG. 9A shows a five-step procedure for the preparation of the carboxyfluorescein-derived molecular tag precursors, namely, Pro2, Pro4, Pro6, Pro7, Pro8, Pro9, Pro10, Pro11, Pro12, and Pro13. The first step involves the reaction of a 5-or 6-FAM with N-hydroxysuccinimide (NHS) and 1,3-dicylcohexylcarbodiimide (DCC) in DMF to give the corresponding ester, which was then treated with a variety of diamines to yield the desired amide, compound 1. Treatment of compound 1 with N-succinimidyl iodoacetate provided the expected iodoacetamide derivative, which was not isolated but was further reacted with 3-mercaptopropionic acid in the presence of triethylamine. Finally, the resulting β-thioacid (compound 2) was converted, as described above, to its NHS ester. The various e-tag moieties were synthesized starting with 5- or 6-FAM, and one of various diamines. The diamine is given $H_2N\char`\^X\char`\^NH_2$ in the first reaction of FIG. 9A. The regioisomer of FAM and the chemical entity of "X" within the diamine are indicated in the table below for each of the molecular tag precursors synthesized. Clearly, the diamine, X, can have a wide range of additional forms, as described above in the discussion of the mobility modifier moiety.

| Precursor | FAM | X |
| --- | --- | --- |
| Pro2 | 5-FAM | $C(CH_3)_2$ |
| Pro4 | 5-FAM | no carbon |
| Pro6 | 5-FAM | $(CH_2)_8$ |
| Pro7 | 5-FAM | $CH_2OCH_2CH_2OCH_2$ |
| Pro8 | 5-FAM | $CH_2CH_2OCH_2CH_2OCH_2CH_2OCH_2CH_2$ |
| Pro9 | 5-FAM | 1,4-phenyl |
| Pro10 | 6-FAM | $C(CH_3)_2$ |
| Pro11 | 6-FAM | no carbon |
| Pro12 | 6-FAM | $CH_2OCH_2CH_2OCH_2$ |
| Pro13 | 6-FAM | $CH_2CH_2OCH_2CH_2OCH_2CH_2OCH_2CH_2$ |

Synthesis of Compound 1

To a stirred solution of 5- or 6-carboxyfluorescein (0.5 mmol) in dry DMF (5 mL) were added N-hydroxysuccinimide (1.1 equiv.) and 1,3-dicylcohexylcarbodiimide (1.1 equiv.). After about 10 minutes, a white solid (dicyclohexylurea) started forming. The reaction mixture was stirred under nitrogen at room temperature overnight. TLC (9:1 $CH_2Cl_2$—MeOH) indicated complete disappearance of the starting material.

The supernatant from the above mixture was added dropwise to a stirred solution of diamine (2–5 equiv.) in DMF (10 mL). As evident from TLC (40:9:1 $CH_2Cl_2$—MeOH—$H_2O$), the reaction was complete instantaneously. The solvent was removed under reduced pressure. Flash chromatography of the resulting residue on latrobeads silica provided the desired amine (compound 1) in 58–89% yield. The $^1H$ NMR (300 MHz, DMSO-$d_6$) of compound 1 was in agreement with the assigned structure.

Synthesis of Compound 2

To the amine (compound 1) (0.3 mmol) were sequentially added dry DMF (10 mL) and N-succinimidyl iodoacetate (1.1 equiv.). The resulting mixture was stirred at room temperature until a clear solution was obtained. TLC (40:9:1 $CH_2Cl_2$—MeOH—$H_2O$) revealed completion of the reaction.

The above reaction solution was then treated with triethylamine (1.2 equiv.) and 3-mercaptopropionic acid (3.2 equiv.). The mixture was stirred at room temperature overnight. Removal of the solvent under reduced pressure followed by flash chromatography afforded the β-thioacid (compound 2) in 62–91% yield. The structure of compound 2 was assigned on the basis of its $^1$NMR (300 MHz, DMSO-$d_6$).

Synthesis of Pro2, Pro4, and Pro6 Through Pro13

To a stirred solution of the β-thioacid (compound 2) (0.05 mmol) in dry DMF (2 mL) were added N-hydroxysuccinimide (1.5 equiv.) and 1,3-dicylcohexylcarbodiimide (1.5 equiv.). The mixture was stirred at room temperature under nitrogen for 24–48 h (until all of the starting material had reacted). The reaction mixture was concentrated under reduced pressure and then purified by flash chromatography to give the target molecule in 41–92% yield.

Preparation of Pro1

Figure 9B:
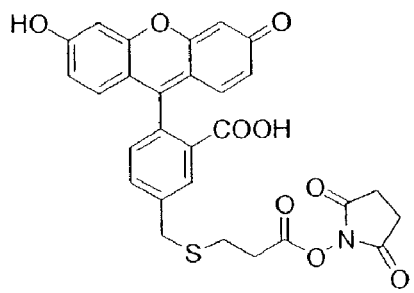
Figure 9B:
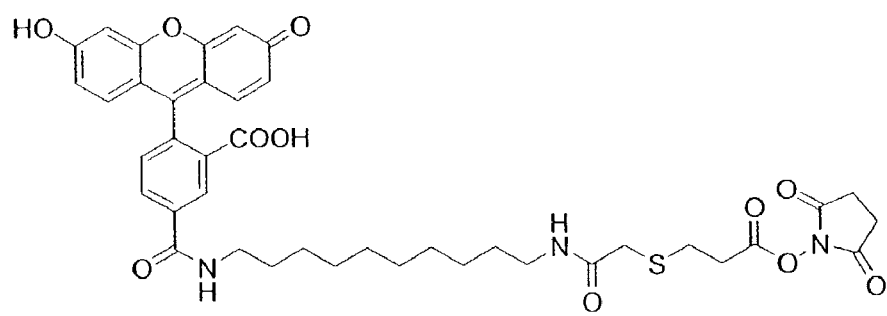
Figure 9B:
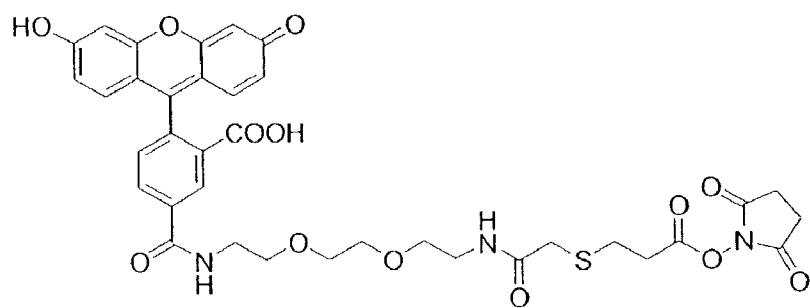
Figure 9B:
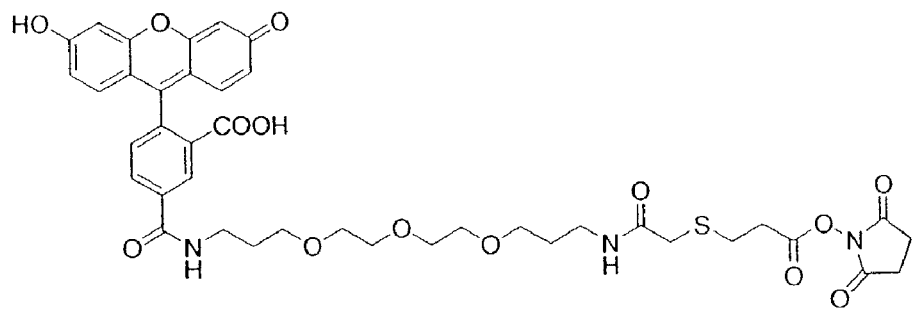

The compounds of this reaction are shown in FIG. 9B. To a stirred solution of 5-iodoacetamidofluorescein (compound 4) (24 mg, 0.047 mmol) in dry DMF (2 mL) were added triethylamine (8 µL, 0.057 mmol) and 3-mercaptopropionic acid (5 µL, 0.057 mmol). The resulting solution was stirred at room temperature for 1.5 h. TLC (40:9:1 $CH_2Cl_2$—MeOH—$H_2O$) indicated completion of the reaction. Subsequently, N-hydroxysuccinimide (9 mg, 0.078 mmol) and 1,3-dicylcohexylcarbodiimide (18 mg, 0.087 mmol) were added. The reaction mixture was stirred at room temperature under nitrogen for 19 h at which time TLC showed complete disappearance of the starting material. Removal of the solvent under reduced pressure and subsequent flash chromatography using 25:1 and 15:1 CH$_2$Cl$_2$—MeOH as eluant afforded Pro1 (23 mg, 83%).

Preparation of Pro3

Figure 9C:
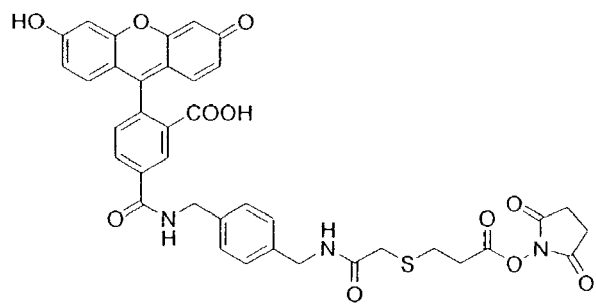
Figure 9C:
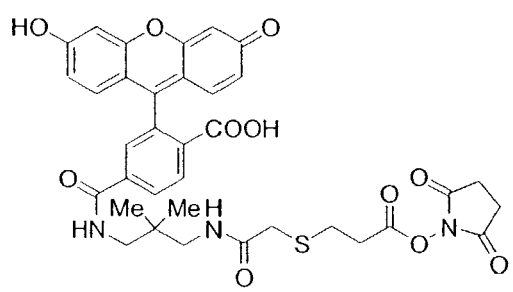
Figure 9C:
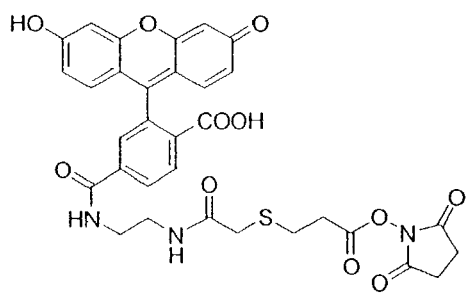
Figure 9C:
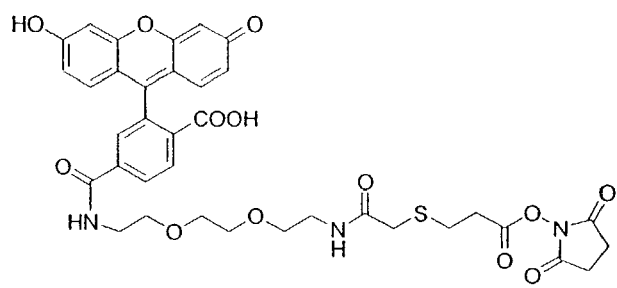

The compounds of this reaction are shown in FIG. 9C. To a stirred solution of 6-iodoacetamidofluorescein (compound 5) (26 mg, 0.050 mmol) in dry DMF (2 mL) were added triethylamine (8 µL, 0.057 mmol) and 3-mercaptopropionic acid (5 µL, 0.057 mmol). The resulting solution was stirred at room temperature for 1.5 h. TLC (40:9:1 CH$_2$Cl$_2$—MeOH—H$_2$O) indicated completion of the reaction. Subsequently, N-hydroxysuccinimide (11 mg, 0.096 mmol) and 1,3-dicylcohexylcarbodiimide (18 mg, 0.087 mmol) were added. The reaction mixture was stirred at room temperature under nitrogen for 19 h at which time TLC showed complete disappearance of the starting material. Removal of the solvent under reduced pressure and subsequent flash chromatography using 30:1 and 20:1 CH$_2$Cl$_2$—MeOH as eluant provided Pro3 (18 mg, 61%).

Preparation of Pro5

Figure 9D:
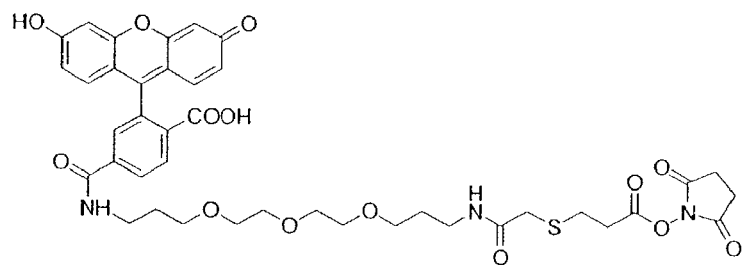
Figure 9D:
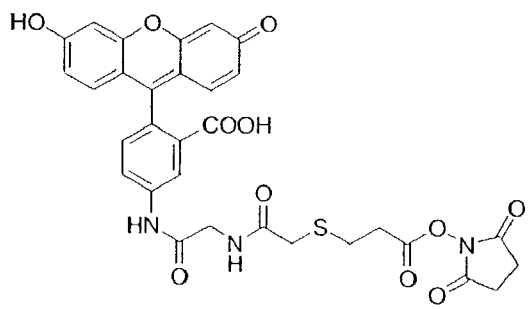
Figure 9D:
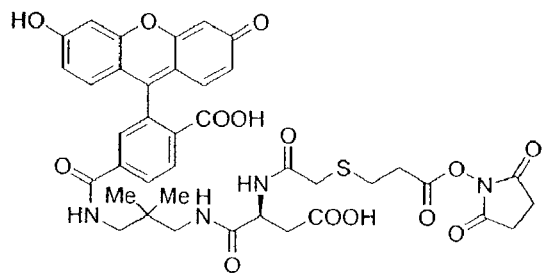
Figure 9D:
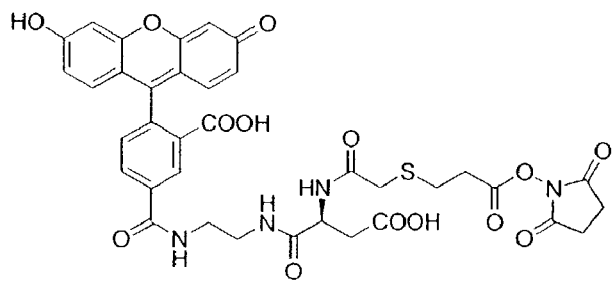

The compounds of this reaction are shown in FIG. 9D.

Synthesis of Compound 7

To a stirred solution of 5-(bromomethyl)fluorescein (compound 6) (40 mg, 0.095 mmol) in dry DMF (5 mL) were added triethylamine (15 µL, 0.108 mmol) and 3-mercaptopropionic acid (10 µL, 0.115 mmol). The resulting solution was stirred at room temperature for 2 days. TLC (40:9:1 CH$_2$Cl$_2$—MeOH—H$_2$O) indicated completion of the reaction. The reaction solution was evaporated under reduced pressure. Finally, flash chromatography employing 30:1 and 25:1 CH$_2$Cl$_2$—MeOH as eluant provided the β-thioacid (compound 7) (28 mg, 66%).

Synthesis of Pro5

To a solution of the acid (compound 7) (27 mg, 0.060 mmol) in dry DMF (2 mL) were added N-hydroxysuccinimide (11 mg, 0.096 mmol) and 1,3-dicylcohexylcarbodiimide (20 mg, 0.097 mmol). The reaction mixture was stirred at room temperature under nitrogen for 2 days at which time TLC (9:1 CH$_2$Cl$_2$—MeOH) showed complete disappearance of the starting material. Removal of the solvent under reduced pressure and subsequent flash chromatography with 30:1 CH$_2$Cl$_2$—MeOH afforded Pro5 (24 mg, 73%).

Preparation of Pro14

Figure 9E:
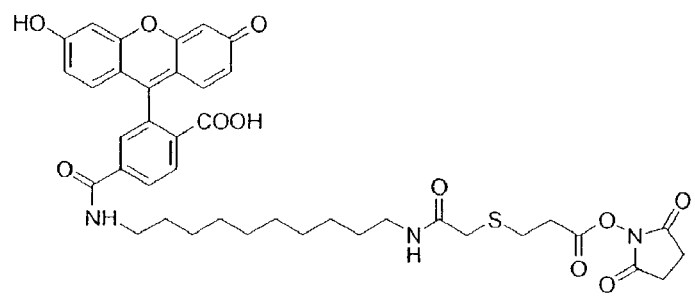
Figure 9E:
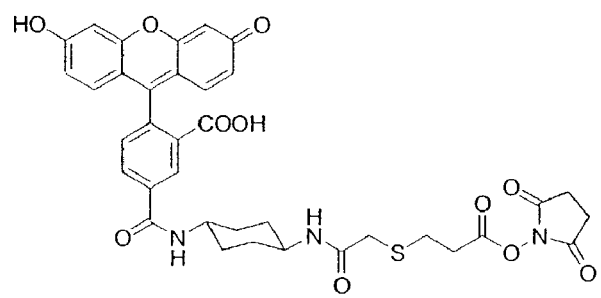
Figure 9E:
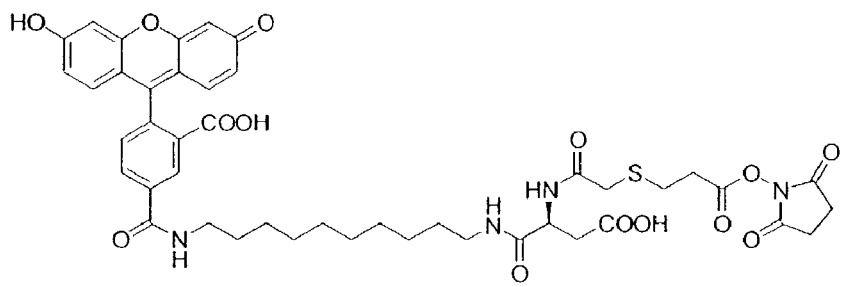
Figure 9E:
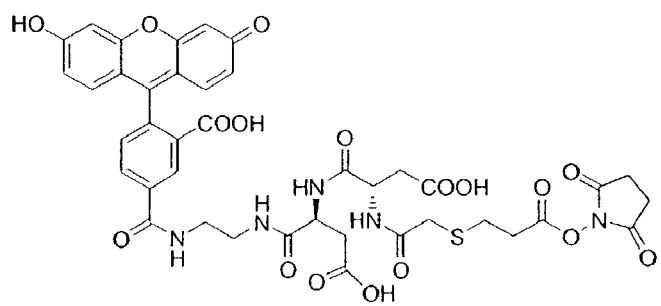
Figure 9F:
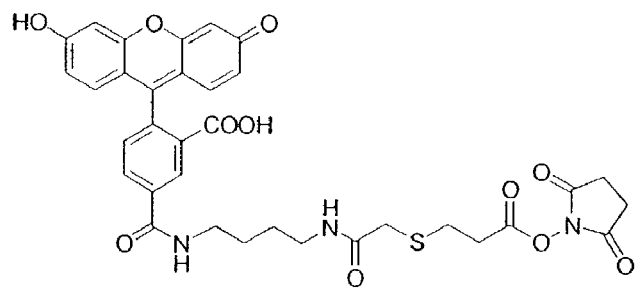
Figure 9F:
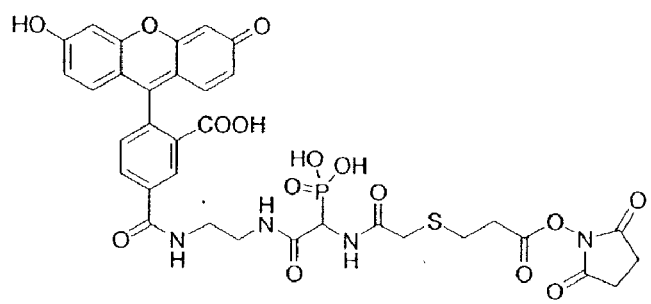
Figure 9F:
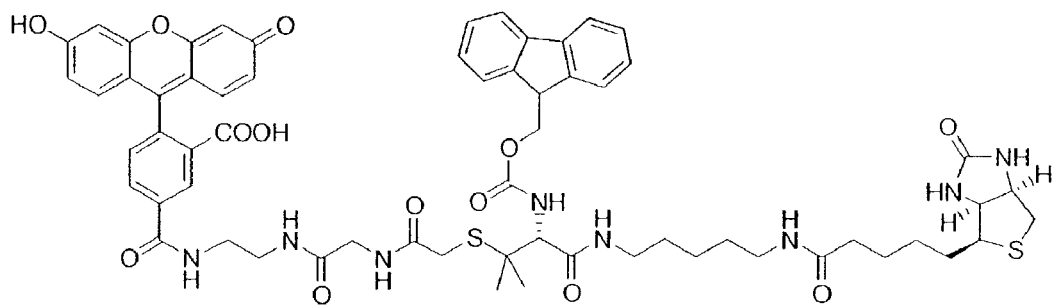
Figure 9F:
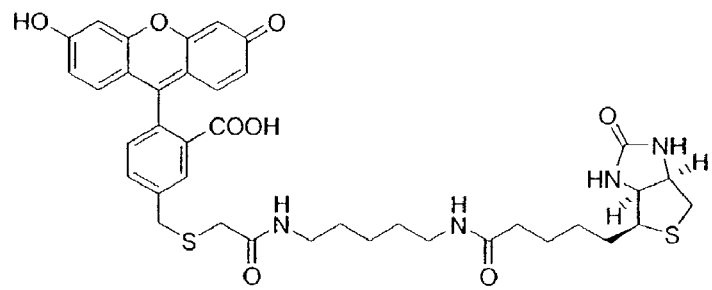
Figure 9G:
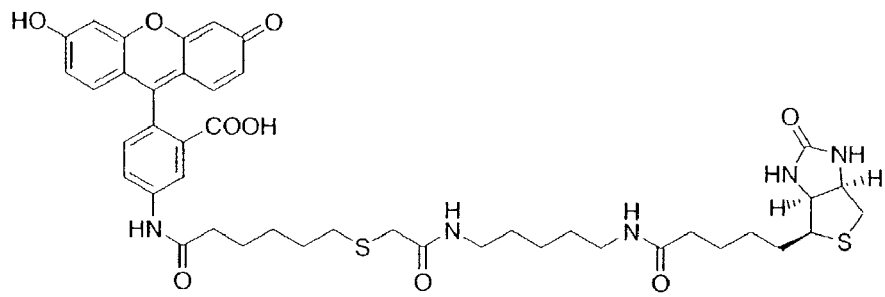
Figure 9G:
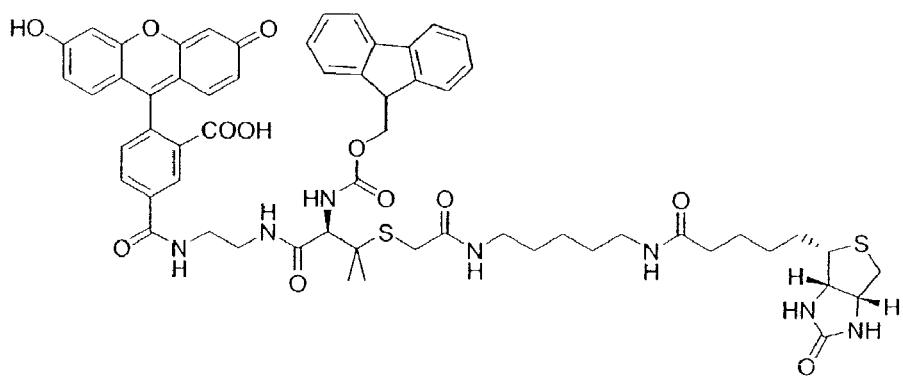
Figure 9G:
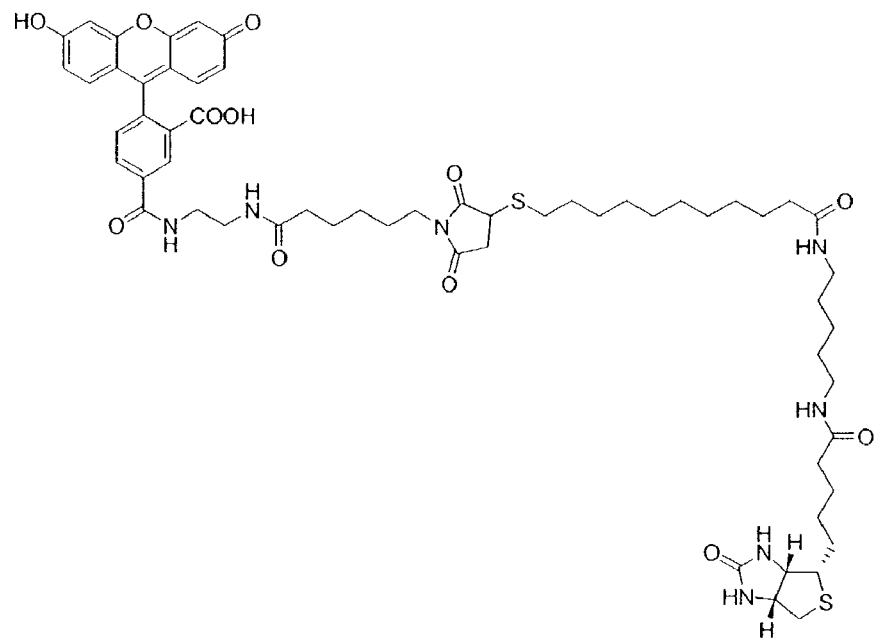
Figure 9H:
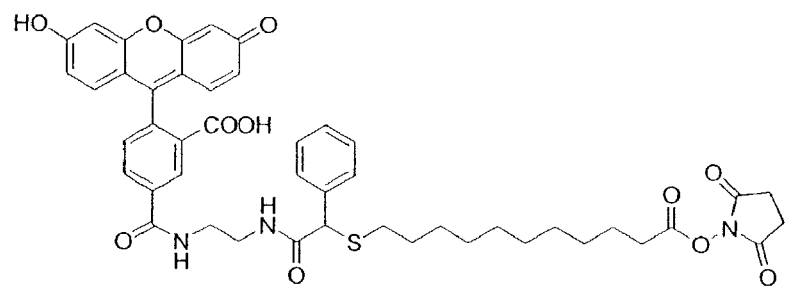
Figure 9H:
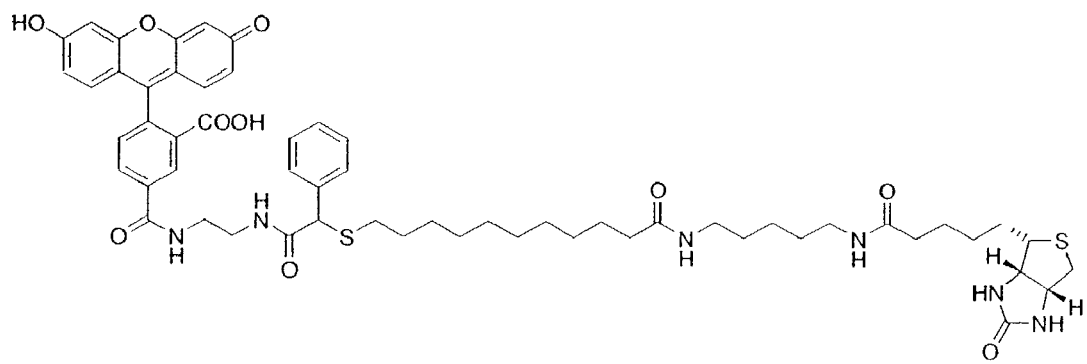
Figure 9H:
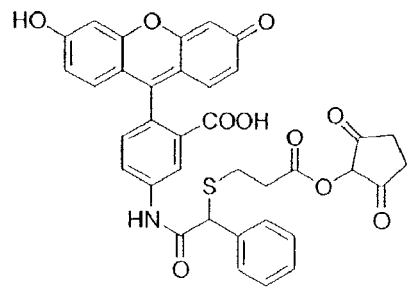
Figure 9H:
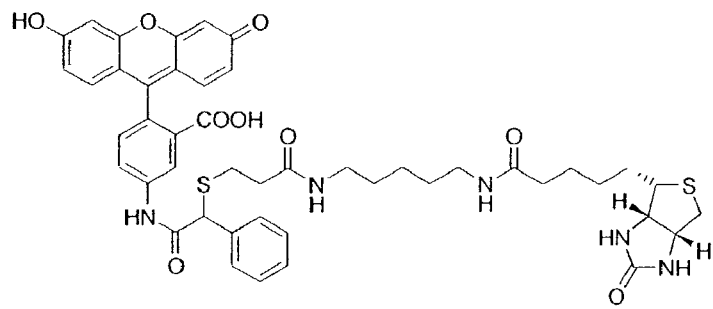
Figure 9I:
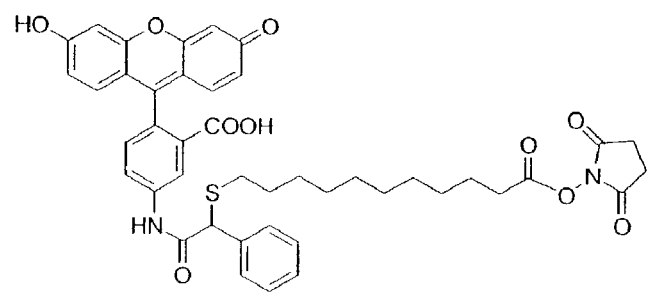
Figure 9I:
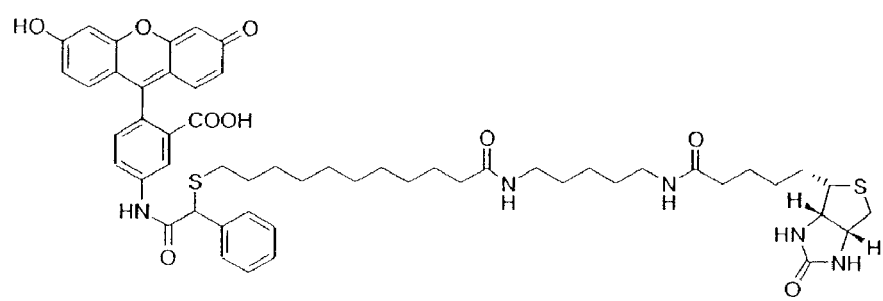
Figure 9I:
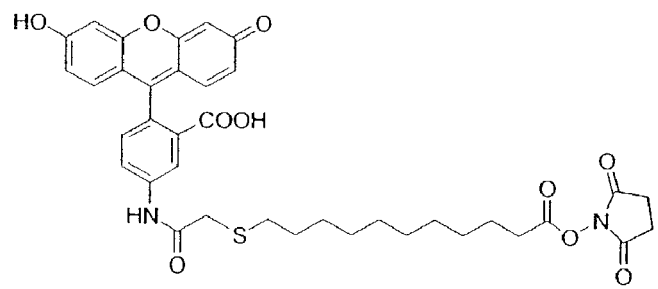
Figure 9I:
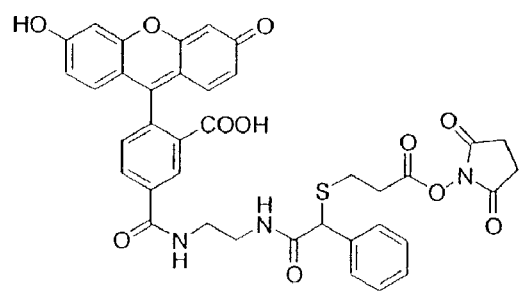
Figure 9J:
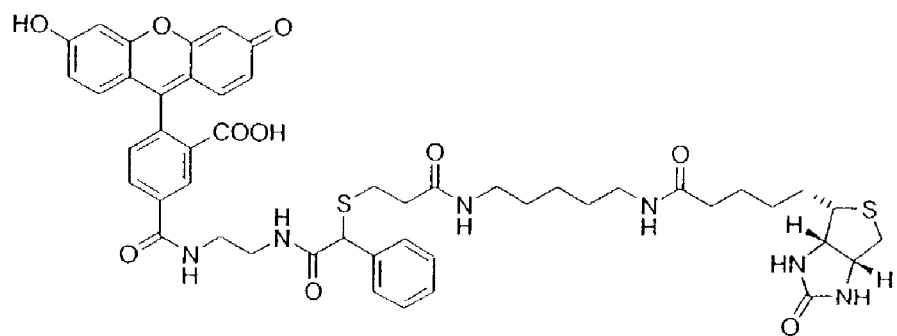
Figure 9J:
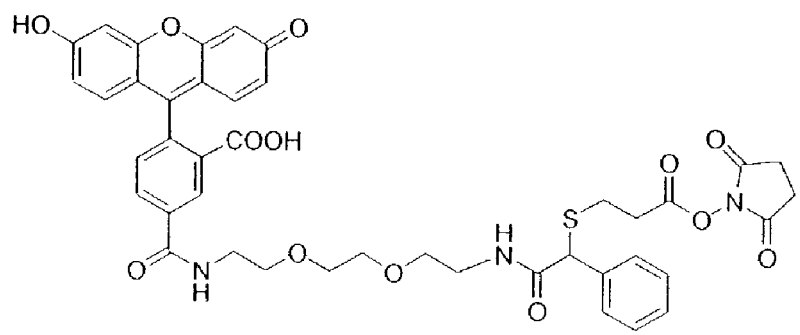
Figure 9J:
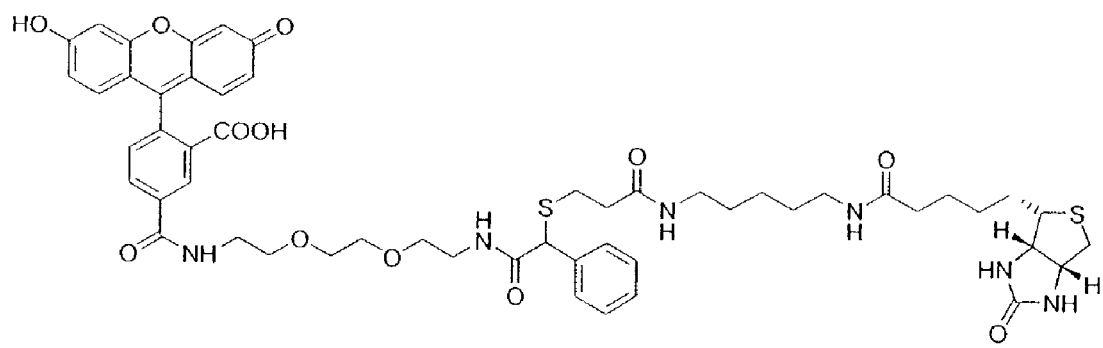
Figure 10A:
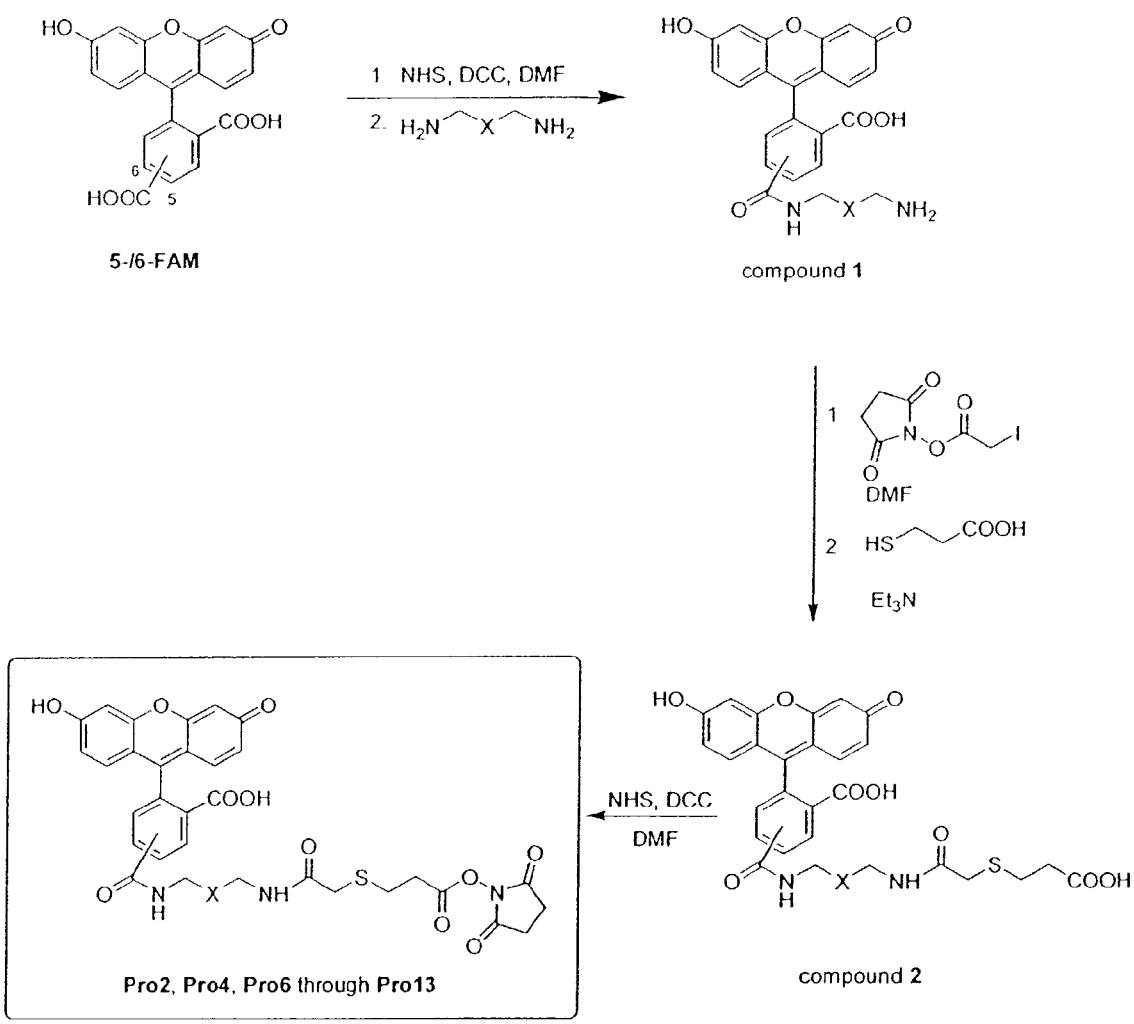
FIGS. 10A–I illustrate the chemistries of synthesis of the e-tag moieties illustrated in FIG. 9.
Figure 10B:
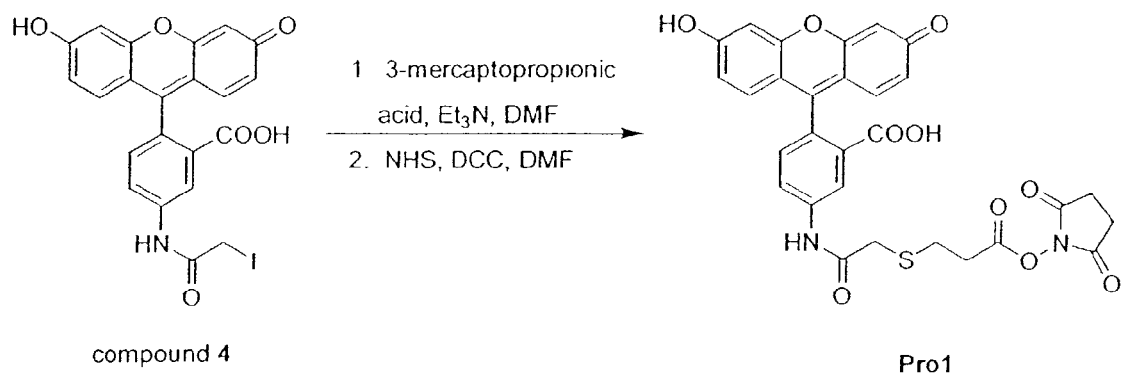
Figure 10C:
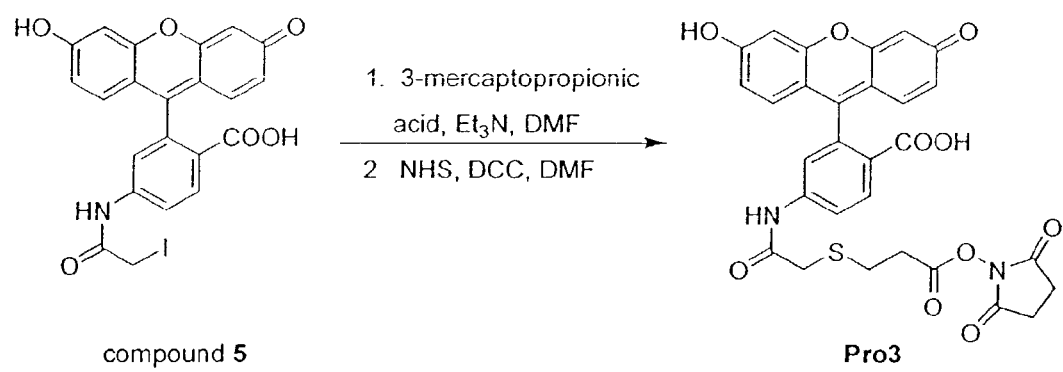
Figure 10D:
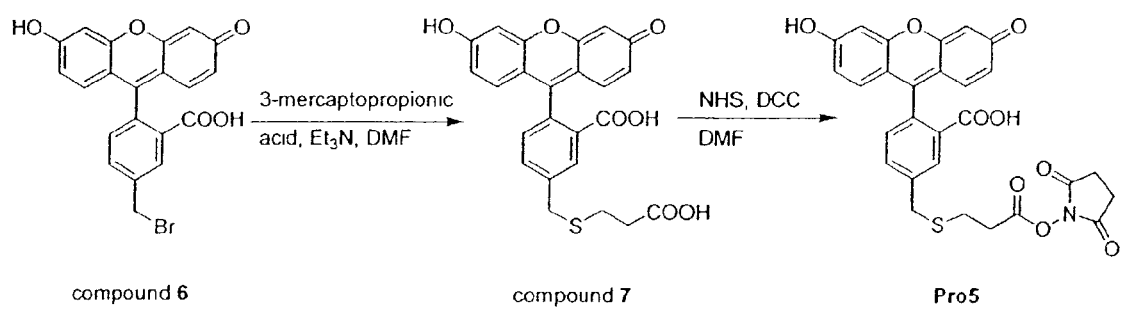
Figure 10E:
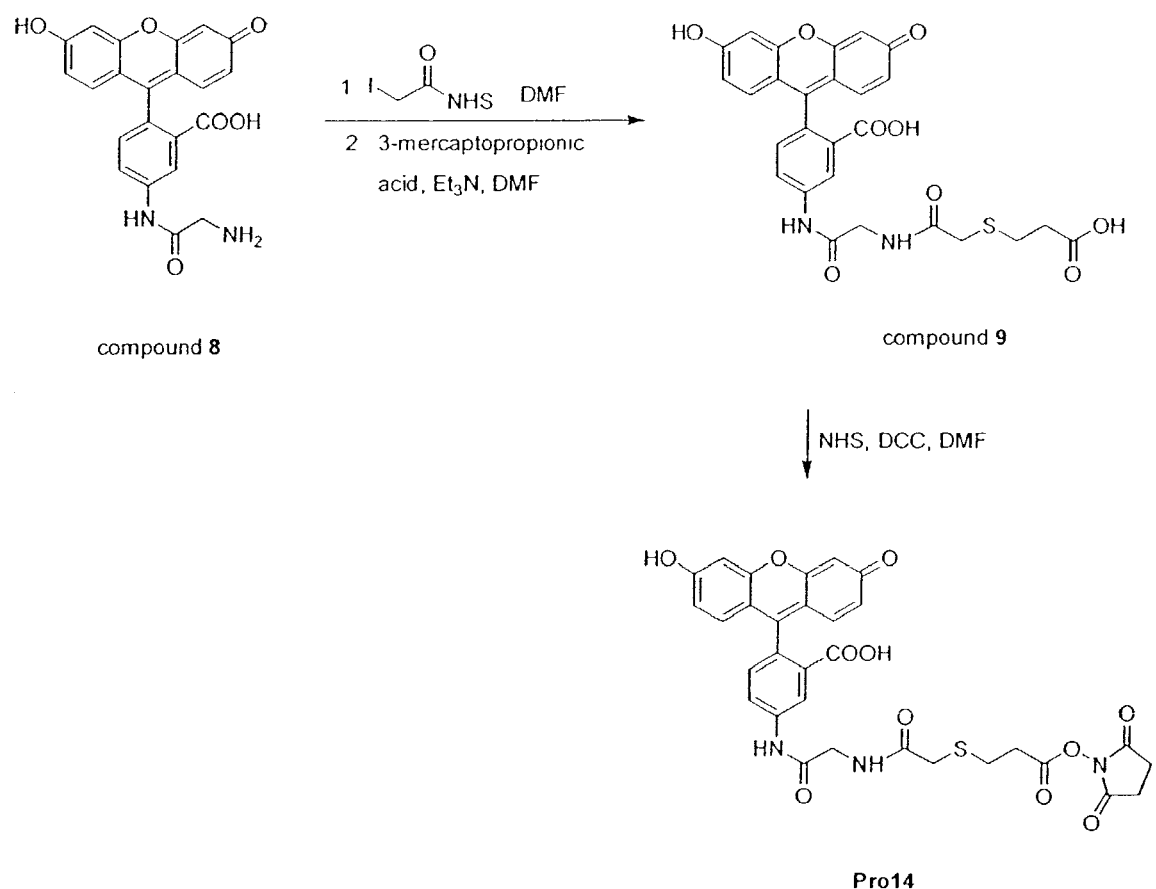
Figure 10F:
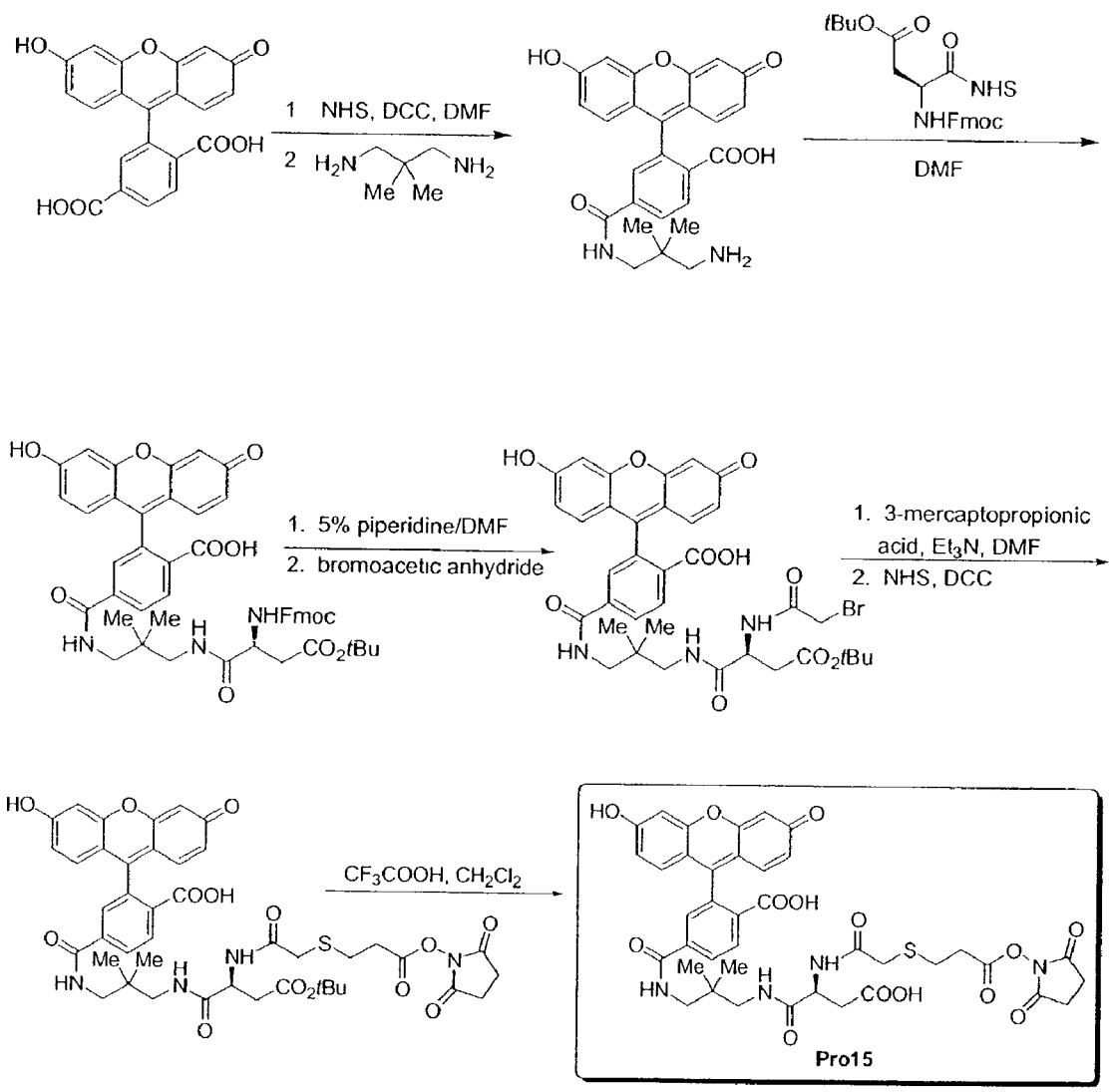
Figure 10G:
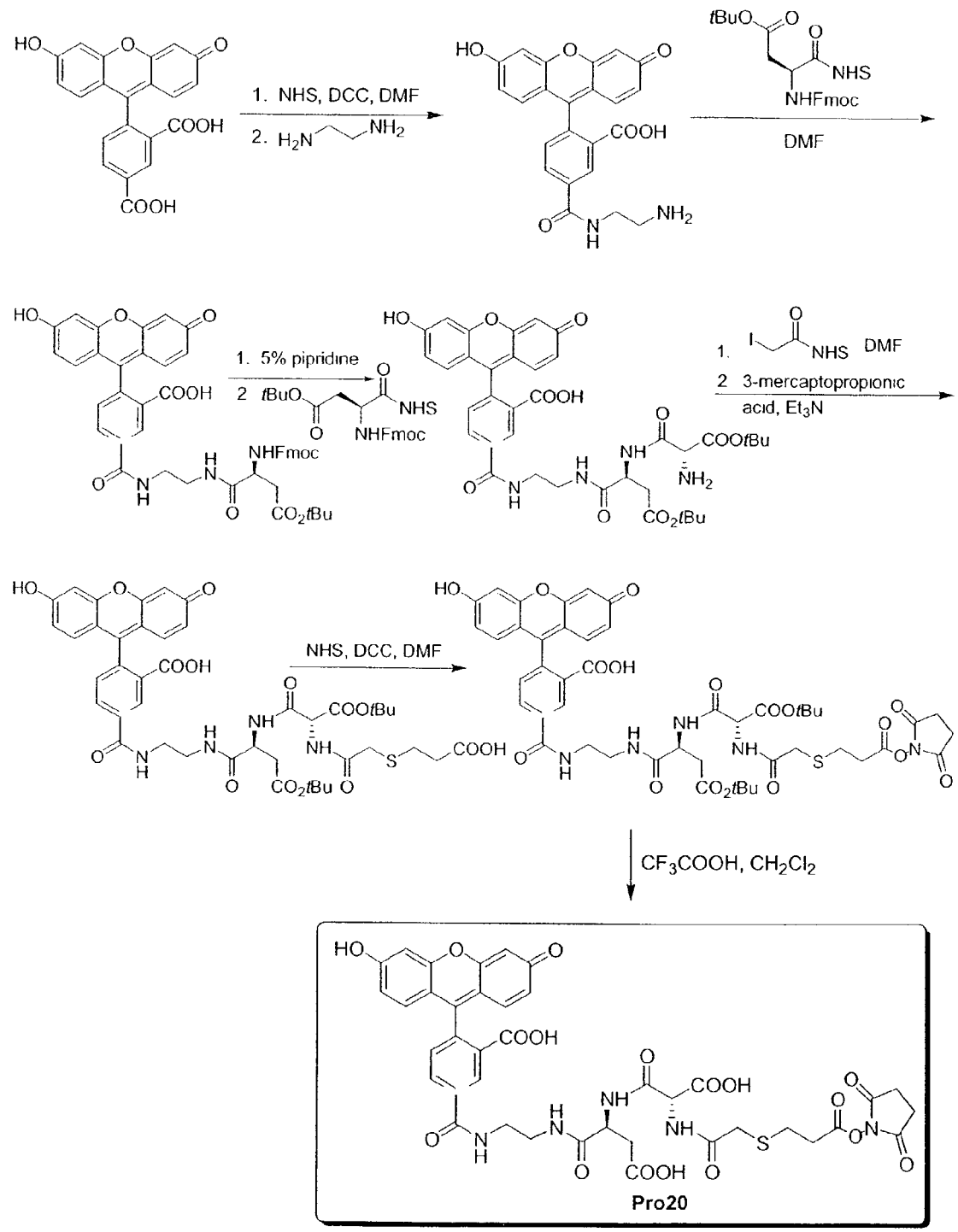
Figure 10H:
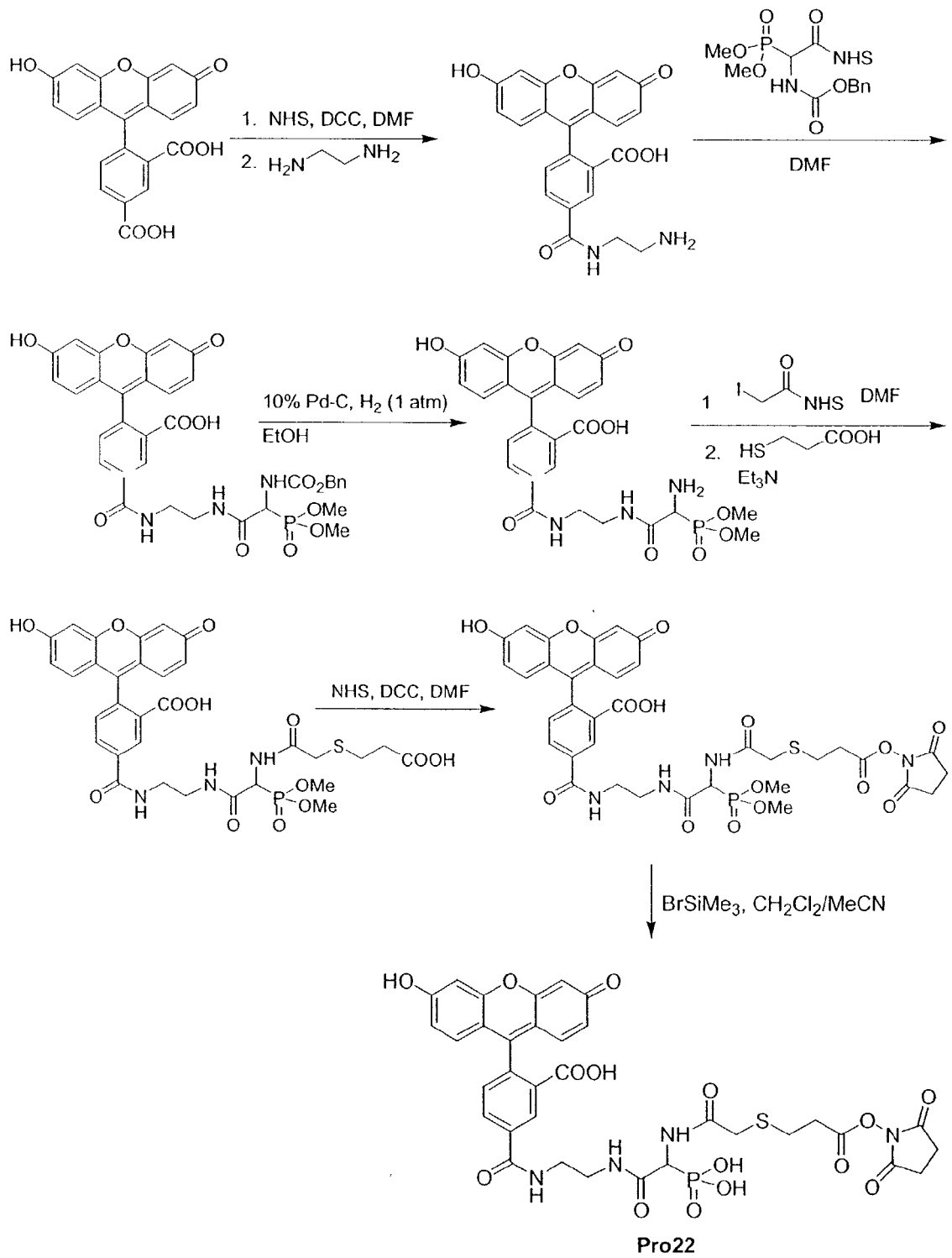
Figure 10I:
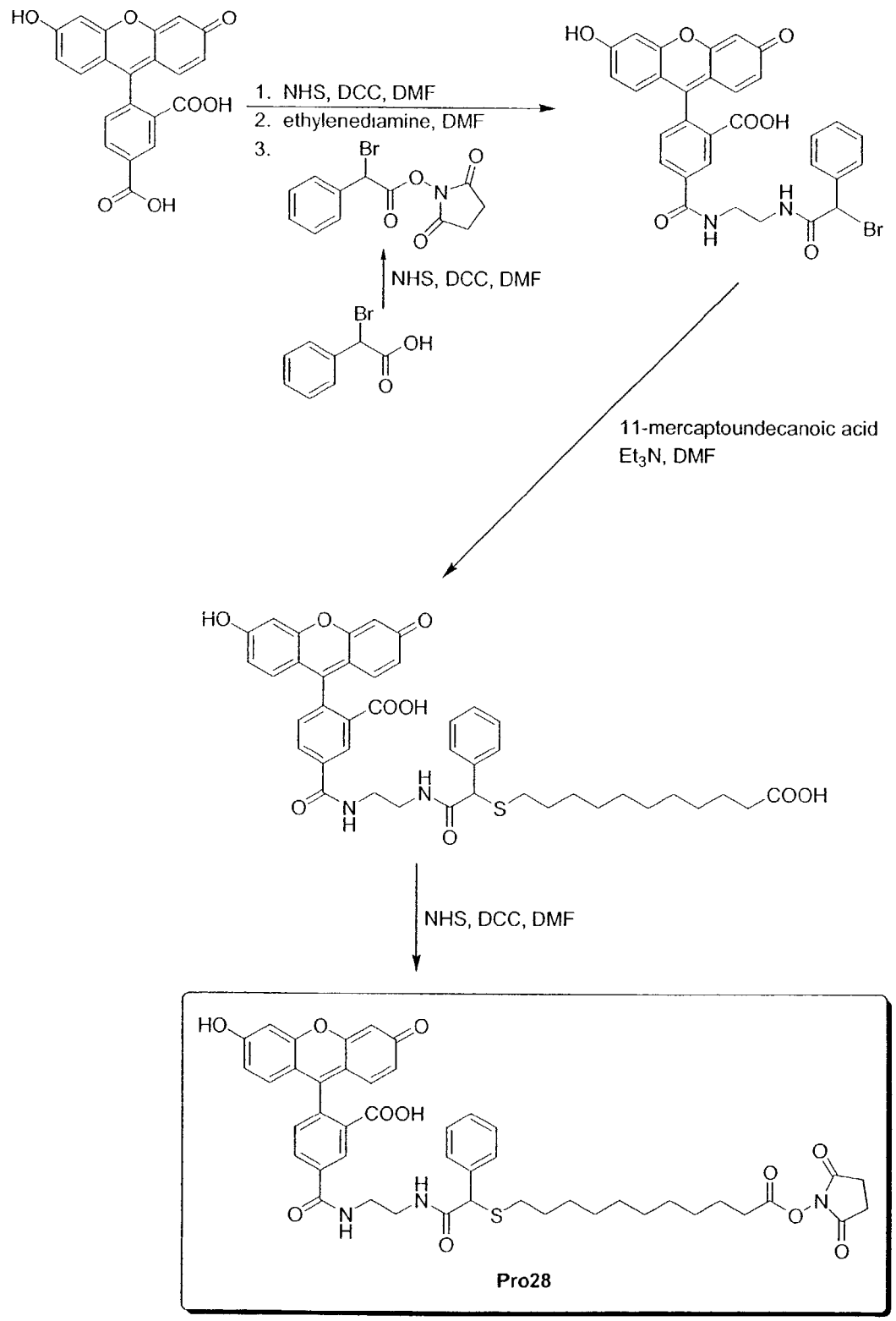

The compounds of this reaction are shown in FIG. 9E.

Synthesis of Compound 9

To 5-aminoacetamidofluorescein (compound 8) (49 mg, 0.121 mmol) were sequentially added dry DMF (4 mL) and N-succinimidyl iodoacetate (52 mg, 0.184). A clear solution resulted and TLC (40:9:1 CH$_2$Cl$_2$—MeOH—H$_2$O) indicated complete disappearance of the starting material.

The above reaction solution was then treated with triethylamine (30 µL, 0.215 mmol) and 3-mercaptopropionic acid (3 µL, 0.344 mmol). The resulting mixture was stirred for 2 h. Removal of the solvent under reduced pressure followed by flash chromatography using 20:1 and 15:1 CH$_2$Cl$_2$—MeOH as eluant gave the β-thioacid (compound 9) (41 mg, 62%). The structural assignment was made on the basis of $^1$NMR (300 MHz, DMSO-d$_6$).

Synthesis of Pro14

To a stirred solution of compound 9 (22 mg, 0.04 mmol) in dry DMF (2 mL) were added N-hydroxysuccinimide (9 mg, 0.078 mmol) and 1,3-dicylcohexylcarbodiimide (16 mg, 0.078 mmol). The resulting solution was stirred at room temperature under nitrogen for about 24 h. The reaction mixture was concentrated under reduced pressure and the residue purified by flash chromatography using 30:1 and 20:1 CH$_2$Cl$_2$—MeOH as eluant to give Pro14 (18 mg, 70%).

Synthesis of Pro15, Pro20, Pro22, and Pro28

The synthesis schemes for producing NHS esters of molecular tags Pro15, Pro20, Pro22, and Pro28 are shown in FIGS. 16F–I, respectively. All of the reagent and reaction conditions are conventional in the art and proceed similarly as the reactions described above.

Example 5

Attachment of Molecular Tags and Antibodies to Aminodextran Derivatized Microspheres In this example, Pro28-NHS and the heterobifunctional cross-linking agent SIAX are reacted with aminodextran-coated microspheres to give microspheres having molecular tags and sulfhydryl-reactive iodoacetyl moieties attached. Separately, antibodies having free sulfhydyl groups are prepared using the heterobifunctional cross-linking agent succinimidyl acetylthioacetate (SATA) in a conventional reaction that converts free amine groups of the antibodies to free sulfhydryls. In a second step, the SATA-modified antibodies are reacted with the microspheres to produce the desired composition.

Sixty five (65) mg of hydroxypropylaminodextran-coated microspheres (prepared as described above) are suspended in 5 mL 50 mM MOPS pH 7. A 10% (w/v) solution (SAIX:Pro28 in 1:2 molar ratio)("tag solution") is prepared in DMSO and 77 µL was added to the microsphere suspension while vortexing. The mixture is incubated at room temperature for an additional 90 minutes in the dark and then a second 77 µL aliquot of tag solution is added and the mixture is incubated for an additional 60 minutes. The suspension is centrifuged and the supernatant is discarded. The microsphere pellet is suspended in 6 mL water by sonication and the centrifugation repeated. The pellet is suspended in 6.5 mL water and stored at 4° C.

SATA-modified antibody is prepared as described in Hermanson (cited above), pgs. 467–469, and is purified by gel filtration on a Sephadex G-25 column, or like column. In preparation for antibody coupling the microspheres are centrifuged, the supernatant is discarded and 1.34 mL coupling buffer is added to the pellet. Coupling buffer consists of the following mixture: 900 µL 0.2 M borate, 2 mM EDTA pH 9 and 333 µL of 0.4 M borate pH 9.45 and 1000 µL of 2 M sodium sulfate. The mixture is degassed and saturated with argon and then 9 µL of 10% Tween 20 detergent is added. The antibody solution is added to the pelleted microspheres in coupling buffer and the mixture is sonicated to suspend the microspheres. The suspension is incubated at 37° C. for 23 hr. Residual iodo groups of the iodoaminodextran coat are capped by reaction with mercaptoacetic acid. After centrifugation, the pelleted microspheres are suspended by sonication in 5 mL of 10 mM mercaptoacetic acid in 0.4 M borate pH 9.45 and the mixture is incubated at 37° C. for 1 hr. After several washes, the derivatized microspheres may be combined with similarly prepared microspheres having different molecular tags and antibodies to form a composition of the invention.

What is claimed is:

1. A composition comprising:
    a mixture of more than one microparticle, each microparticle having a surface with at least one first binding moiety and one or more molecular tags attached, each first binding moiety being specific for a member of a plurality of analytes and the one or more molecular tags being attached to the surface by cleavable linkages, such that different pairs of molecular tags and binding moieties are attached to different microparticles, the molecular tags being selected from a plurality of molecular tags such that each molecular tag of the plurality has one or more physical and/or optical characteristics distinct from those of the other molecular tags of the plurality so that each molecular tag forms a distinguishable peak upon cleavage and upon separation based on such one or more physical and/or optical characteristics; and
    at least one second binding moiety specific for at least one of said one or more target analytes, each second binding moiety having a sensitizer for generating an active species within an effective proximity, wherein at least one second binding moiety is specifically bound to a target analyte so that the cleavable linkage of a molecular tag of a first binding moiety specifically bound to the same target analyte is within the effective proximity of the sensitizer of the second binding moiety.

2. The composition of claim 1 wherein said separation is electrophoretic separation or chromatographic separation, and wherein said molecular tag has a molecular weight in the range of from 100 to 2500 daltons.

3. The composition of claim 1 wherein said sensitizer is a photosensitizer and wherein said first and second binding moieties are both antibody binding compositions.

4. The composition of claim 1 wherein said sensitizer is a photosensitizer and wherein said first binding moiety is a ligand for a cell surface membrane receptor and said second binding moiety is a lipid.

5. The composition in accordance with claim 1, wherein each of said molecular tags attached to said microparticles are selected from a group defined by the formula:

-L-(M,D)

wherein:
    L is a cleavable linkage;
    D is a detection moiety; and
    M is a bond or a water soluble organic compound comprising from 1 to 100 atoms selected from the group consisting of carbon, oxygen, nitrogen, phosphorus, boron, and sulfur, wherein if M is a bond, D is attached to L with the bond M.

6. The composition of claim 5 wherein D is a fluorescent label, a chromogenic label, or an electrochemical label.

7. The composition of claim 5 wherein M is a polymer selected from any one of polyethers, polyesters, polypeptides, oligosaccharides, polyurethanes, polyamides, polysulfonamides, polysulfoxides, polyphosphonates, and block copolymers thereof.

8. The composition of claim 5 wherein D is fluorescein.

9. The composition in accordance with claim 6, 7, or 8 wherein (i) L is selected from the group consisting of olefins, thioethers, selenoethers, thiazoles, oxazoles, and imidazoles, (ii) said plurality of molecular tags is in the range of from 2 to 100, and (iii) said separation is electrophoretic separation.

10. The composition of claim 9 wherein said plurality of molecular tags is in the range of from 3 to 50.

11. A method for detecting more than one target analytes in a sample, the method comprising the steps of:
    contacting the sample with at least one microparticle for each target analyte, each microparticle having a surface with at least one first binding moiety and at least one molecular tags attached, each first binding moiety being specific for one of the more than one target analytes and the molecular tags being attached to the surface by cleavable linkages, such that different pairs of molecular tags and first binding moieties are attached to different microparticles, the molecular tags being selected from a plurality of molecular tags such that each molecular tag of the plurality has one or more physical and/or optical characteristics distinct from those of the other molecular tags of the plurality so that each molecular tag forms a distinguishable peak upon cleavage and separation based on such one or more physical and/or optical characteristics;
    contacting the sample with a second binding composition comprising at least one second binding moiety specific for each of the target analytes, each such second binding moiety having a sensitizer for generating an active species capable of cleaving the cleavable linkage such that in the presence of a target analyte a complex is formed between the target analyte and at least one first binding moiety and at least one second binding moiety specific therefor, and such that the sensitizer of the second binding moiety generates an active species that cleaves one or more cleavable linkages to release one or more molecular tags from at least one microparticle; and
    separating and identifying the released molecular tags by the one or more physical and/or optical characteristics to determine the target analytes in the sample.

12. The method of claim 11 wherein said separation is electrophoretic separation or chromatographic separation, and wherein said molecular tag has a molecular weight in the range of from 100 to 2500 daltons.

13. The method of claim 11 wherein said sensitizer is a photosensitizer, and wherein said first and second binding moieties are both antibody binding compositions.

14. The method in accordance with claim 11, 12, or 13 wherein each of said molecular tags attached to said microparticles are selected from a group defined by the formula:

-L-(M,D)

wherein:
    L is a cleavable linkage;
    D is a detection moiety; and
    M is a bond or a water soluble organic compound comprising from 1 to 100 atoms selected from the group consisting of carbon, oxygen, nitrogen, phosphorus, boron, and sulfur, wherein if M is a bond, D is attached to L with the bond M.

15. The method of claim 14 wherein D is a fluorescent label, a chromogenic label, or an electrochemical label.

16. The method of claim 14 wherein M is a polymer selected from any one of polyethers, polyesters, polypeptides, oligosaccharides, polyurethanes, polyamides, polysulfonamides, polysulfoxides, polyphosphonates, and block copolymers thereof.

17. The method of claim 14 wherein D is a fluorescein.

18. The method in accordance with claim 15, 16, or 17 wherein (i) L is selected from the group consisting of olefins, thioethers, selenoethers, thiazoles, oxazoles, and imidazoles, (ii) said plurality of molecular tags is in the range of from 2 to 100, and (iii) said separation is electrophoretic separation.

19. The method of claim 18 wherein said plurality of molecular tags is in the range of from 3 to 50.

* * * * *